(12) United States Patent
Azimi et al.

(10) Patent No.: US 8,398,938 B2
(45) Date of Patent: *Mar. 19, 2013

(54) MICROFLUIDIC THERMAL BEND ACTUATED PRESSURE PULSE VALVE

(75) Inventors: Mehdi Azimi, Rozelle (AU); Matthew Taylor Worsman, Rozelle (AU); Kia Silverbrook, Rozelle (AU)

(73) Assignee: Geneasys Pty Ltd, Balmain, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/150,201

(22) Filed: Jun. 1, 2011

(65) Prior Publication Data

US 2011/0311412 A1 Dec. 22, 2011

Related U.S. Application Data

(60) Provisional application No. 61/356,018, filed on Jun. 17, 2010, provisional application No. 61/437,686, filed on Jan. 30, 2011.

(51) Int. Cl.
*B01L 3/00* (2006.01)
*C12M 1/40* (2006.01)

(52) U.S. Cl. ........ 422/505; 422/502; 422/503; 422/504; 422/507; 422/513; 422/537; 422/538; 422/552; 506/16; 506/39; 435/286.5; 435/286.7; 435/287.2; 435/303.1; 137/7; 137/13; 137/51; 137/803; 137/806; 137/829; 251/12; 251/213; 251/231

(58) Field of Classification Search ................ 137/7, 13, 137/51, 829; 251/213, 231
See application file for complete search history.

(56) References Cited

U.S. PATENT DOCUMENTS

| 2003/0015425 A1* | 1/2003 | Bohm et al. | 204/453 |
|---|---|---|---|
| 2003/0080442 A1 | 5/2003 | Unger | |
| 2005/0264612 A1* | 12/2005 | Silverbrook | 347/56 |
| 2009/0318312 A1 | 12/2009 | McAvoy et al. | |

FOREIGN PATENT DOCUMENTS

| WO | WO 2009/066897 A1 | 5/2009 |
|---|---|---|
| WO | WO 2009/156045 A2 | 12/2009 |

* cited by examiner

*Primary Examiner* — In Suk Bullock
*Assistant Examiner* — Timothy G Kingan

(57) ABSTRACT

A microfluidic thermal bend actuated pressure pulse valve having an inlet for receiving a flow of liquid, an outlet for outputting the flow of liquid, a meniscus anchor between the inlet and the outlet such that the flow from the inlet towards the outlet stops at the meniscus anchor where the liquid forms a meniscus, a movable member for contacting the liquid, and, a thermal expansion actuator for displacing the movable member to generate a pulse in the liquid to dislodge the meniscus such that the liquid flow towards the outlet resumes.

15 Claims, 75 Drawing Sheets

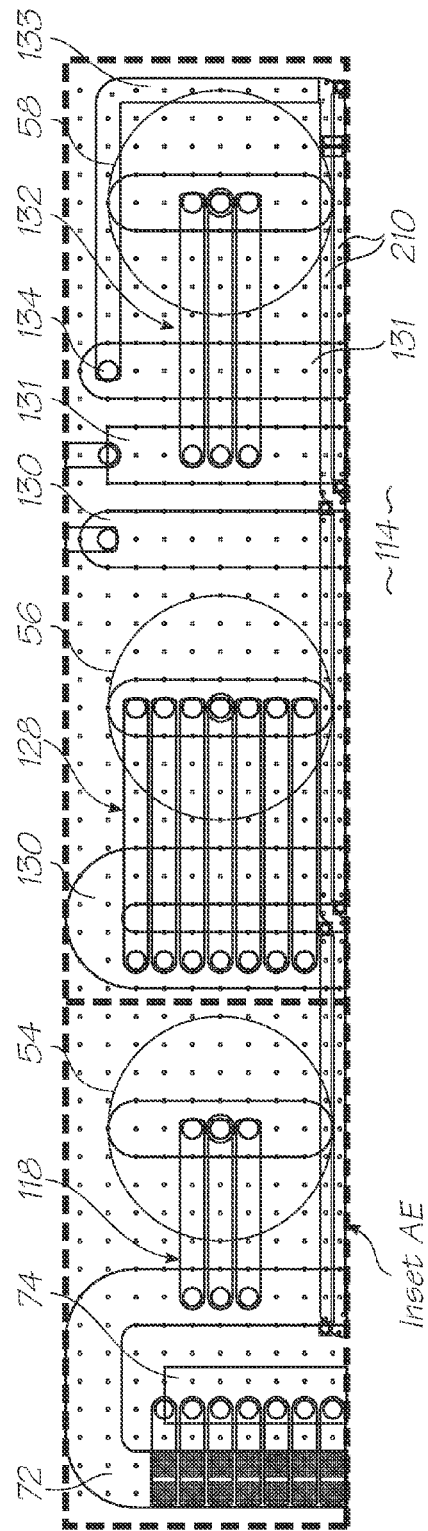
FIG. 13 (Inset AA)
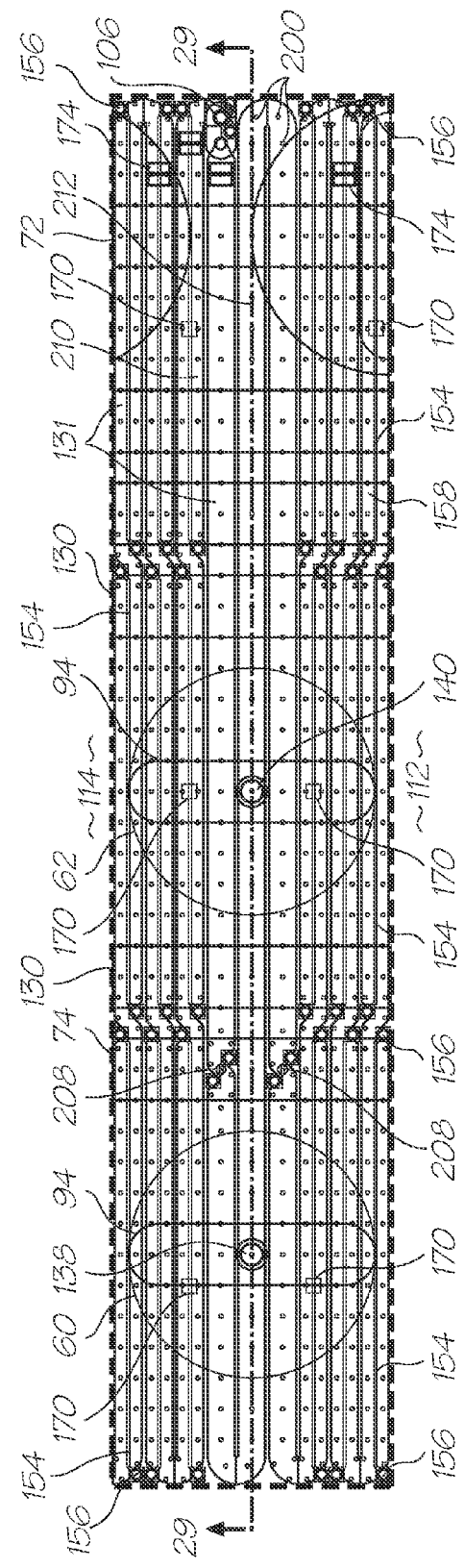
FIG. 14 (Inset AB)

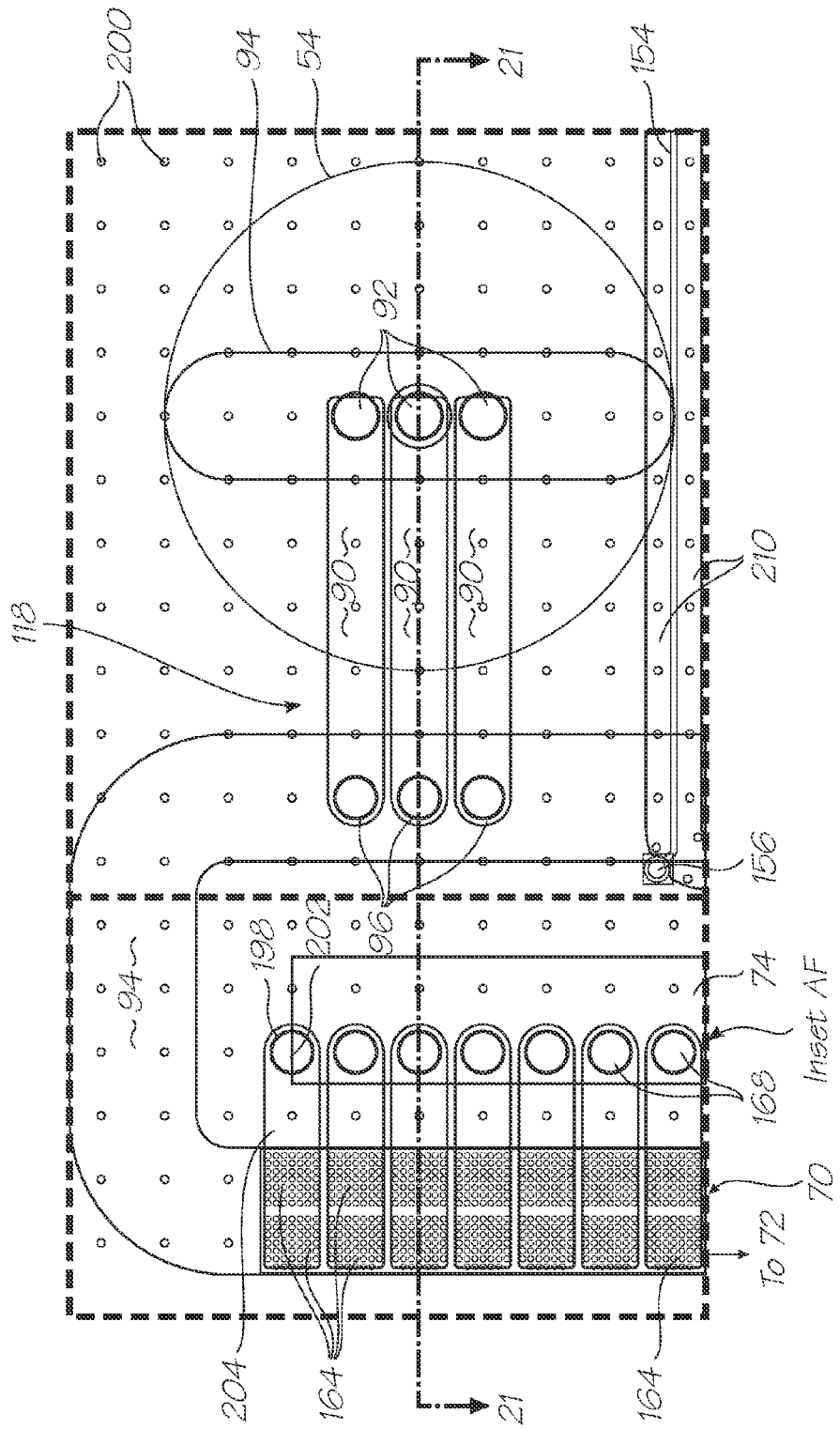
FIG. 15 (Inset AE)

(Inset AE)

(Inset AE)

(Inset AE)

(Inset AE)

(Inset AE)

(Inset AE)

(Inset AB)

(Inset AB)

(Inset AI)

(Inset AB)

(Inset AB)

(Inset AB)

(Inset AB)

FIG. 33 (Inset AF)

FIG. 35 (Inset AC)

(Inset AC)

(Inset AC)

(Inset AK)

(Inset AC)

(Inset AC)

(Inset AC)

(Inset AL)

(Inset AC)

(Inset AM)

(Inset AC)

(Inset AN)

(Inset AC)

(Inset AC)

(Inset AC)

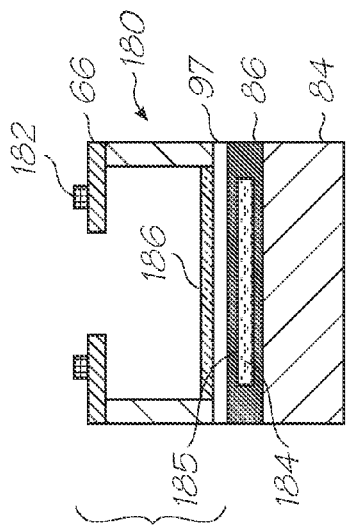
FIG. 54
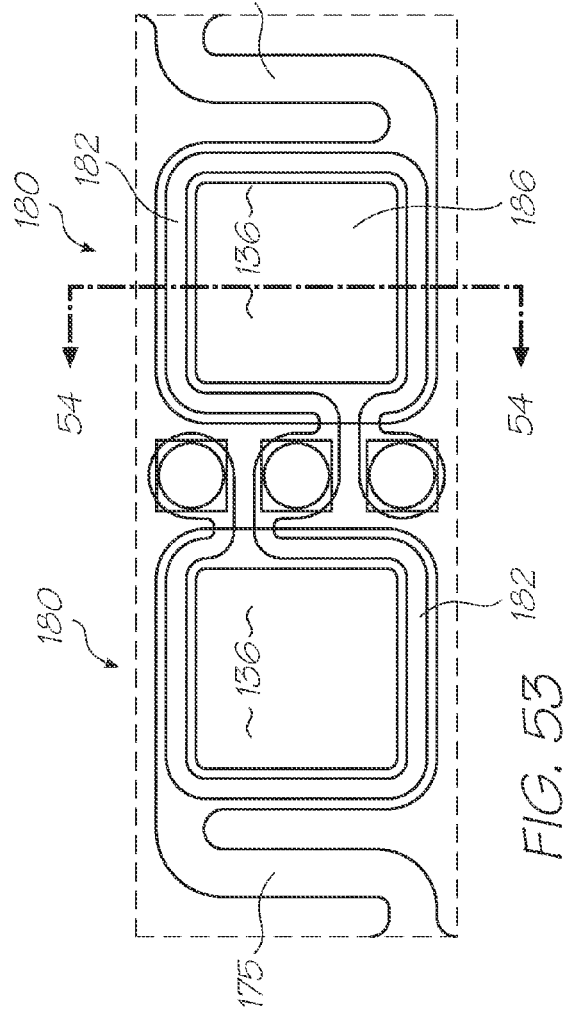
FIG. 53
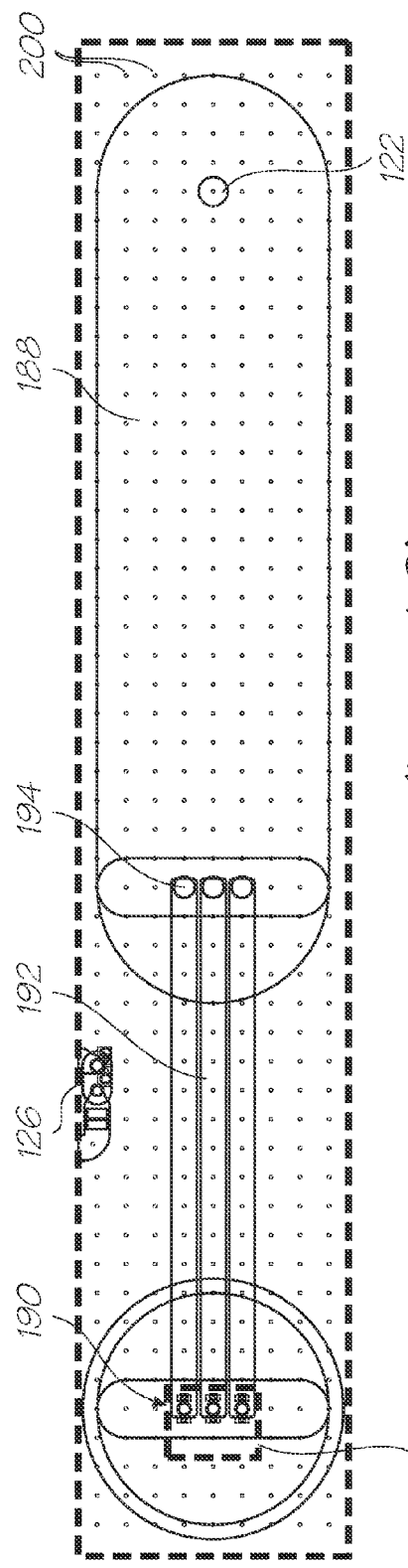
FIG. 55 (Inset AG)

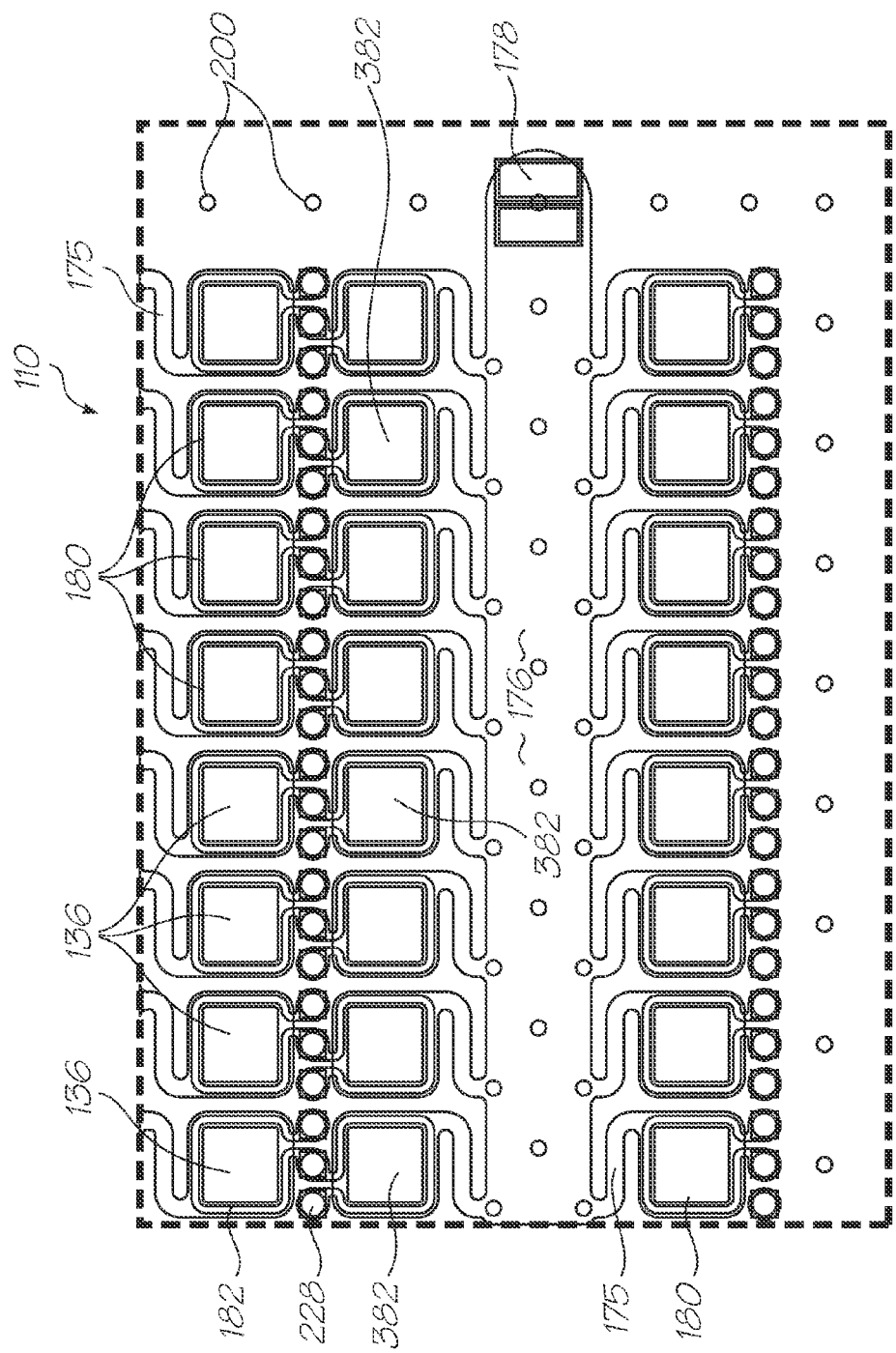
FIG. 56 (Inset AD)

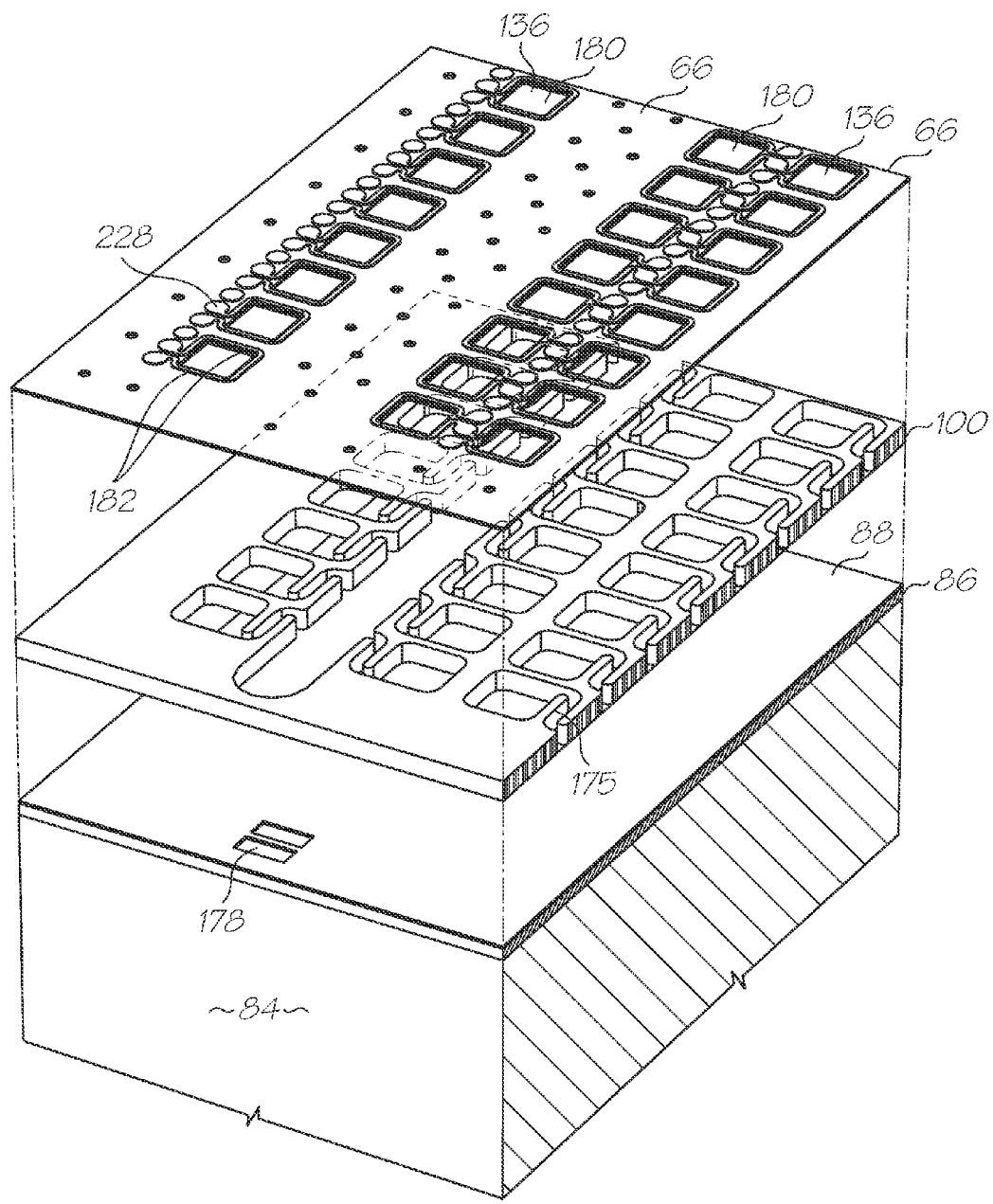
FIG. 57 (Inset AD)

(Inset AH)

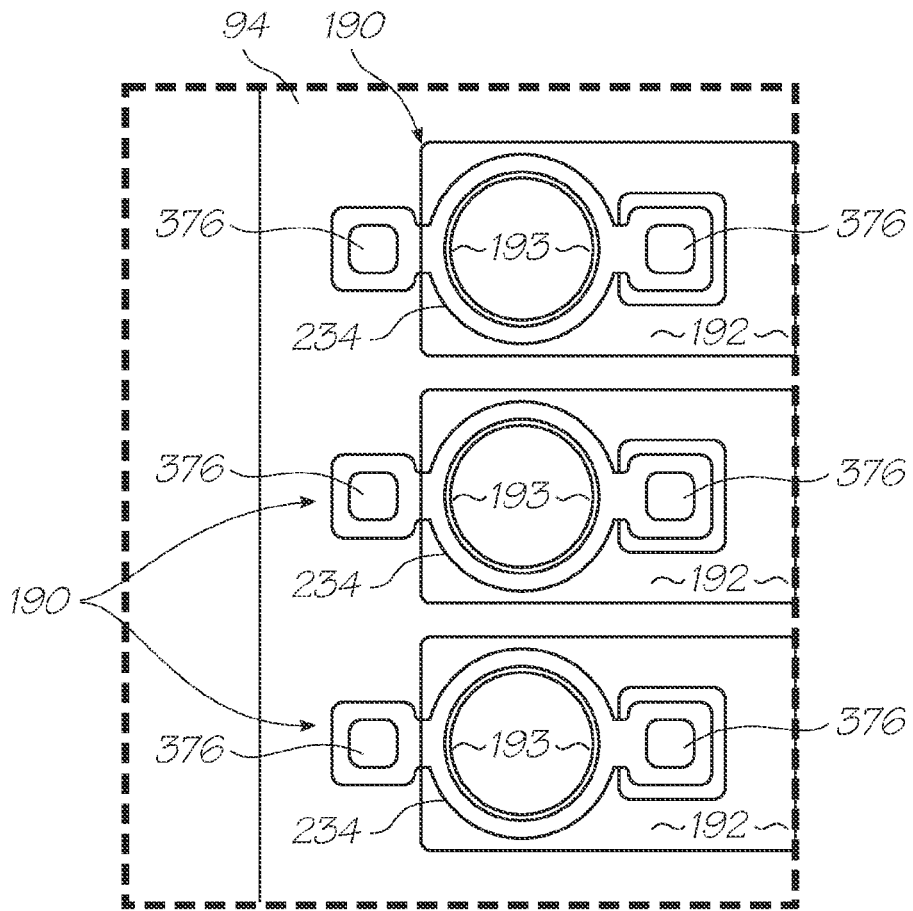
FIG. 74 (Inset AP)
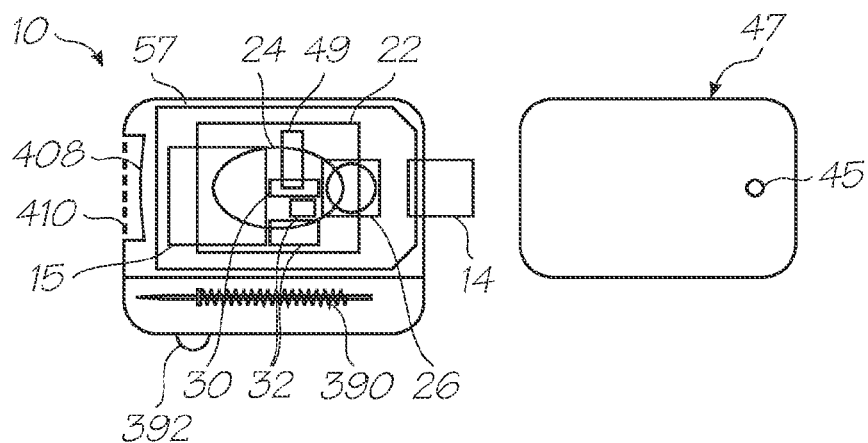
FIG. 77

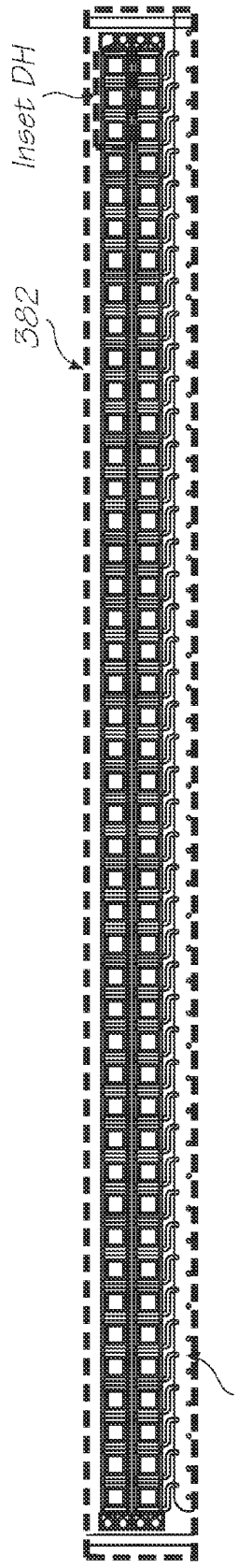
FIG. 93 (Inset DG)
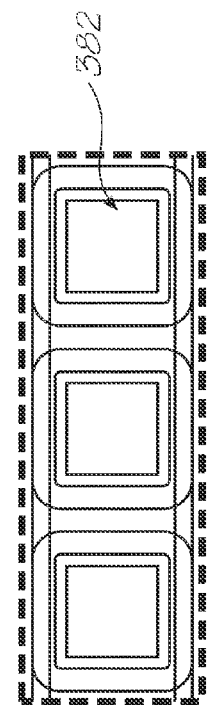
FIG. 94 (Inset DH)

MICROFLUIDIC THERMAL BEND ACTUATED PRESSURE PULSE VALVE

FIELD OF THE INVENTION

The present invention relates to diagnostic devices that use microsystems technologies (MST). In particular, the invention relates to microfluidic and biochemical processing and analysis for molecular diagnostics.

CO-PENDING APPLICATIONS

The following applications have been filed by the Applicant which relate to the present application:

| | | | | |
|---|---|---|---|---|
| 13,149,900 | 13,149,913 | 13,149,916 | 13,149,919 | 13,149,922 |
| 13,149,925 | 13,149,928 | 13,149,931 | 13,149,933 | 13,149,937 |
| 13,149,941 | 13,149,944 | 13,149,947 | 13,149,951 | 13,149,954 |
| 13,149,958 | 13,149,962 | 13,149,991 | 13,149,999 | 13,150,004 |
| 13,150,014 | 13,150,029 | 13,150,048 | 13,150,065 | 13,150,071 |
| 13,150,075 | 13,150,094 | 13,150,102 | 13,150,109 | 13,150,118 |
| 13,150,122 | 13,150,126 | 13,150,130 | 13,150,134 | 13,150,138 |
| 13,150,142 | 13,150,149 | 13,150,153 | 13,150,157 | 13,150,161 |
| 13,150,165 | 13,150,169 | 13,150,174 | 13,150,178 | 13,150,181 |
| 13,150,184 | 13,150,188 | 13,150,192 | 13,150,195 | 13,150,200 |
| 13,150,204 | 13,150,207 | 13,150,211 | 13,150,216 | 13,150,220 |
| 13,150,223 | 13,150,225 | 13,150,228 | 13,150,231 | 13,150,236 |
| 13,150,238 | 13,150,241 | 13,150,243 | 13,150,245 | 13,150,247 |
| 13,150,249 | 13,150,252 | 13,150,256 | 13,149,897 | 13,150,259 |
| 13,150,262 | 13,150,265 | 13,150,248 | 13,150,251 | 13,150,257 |
| 13,150,260 | 13,150,263 | 13,150,266 | 13,150,268 | 13,150,270 |
| 13,150,272 | 13,150,239 | 13,150,255 | 13,150,258 | 13,150,261 |
| 13,150,264 | 13,150,267 | 13,150,269 | 13,150,271 | 13,149,932 |
| 13,149,935 | 13,149,942 | 13,149,946 | 13,149,890 | 13,149,950 |
| 13,149,956 | 13,149,960 | 13,149,965 | 13,149,968 | 13,149,971 |
| 13,149,973 | 13,149,975 | 13,149,979 | 13,149,981 | 13,149,984 |
| 13,149,986 | 13,149,990 | 13,149,995 | 13,150,001 | 13,150,006 |
| 13,150,008 | 13,150,011 | 13,150,017 | 13,150,021 | 13,150,024 |
| 13,150,030 | 13,150,033 | 13,150,038 | 13,150,041 | 13,150,046 |
| 13,150,050 | 13,150,053 | 13,150,057 | 13,150,061 | 13,150,064 |
| 13,150,068 | 13,150,073 | 13,150,077 | 13,150,080 | 13,150,084 |
| 13,150,088 | 13,150,091 | 13,150,095 | 13,150,098 | 13,150,101 |
| 13,150,105 | 13,150,108 | 13,150,112 | 13,150,115 | 13,150,119 |
| 13,150,123 | 13,150,127 | 13,150,131 | 13,150,135 | 13,150,140 |
| 13,150,146 | 13,150,150 | 13,150,154 | 13,150,158 | 13,150,162 |
| 13,149,903 | 13,150,167 | 13,150,173 | 13,150,177 | 13,150,190 |
| 13,150,196 | 13,149,929 | 13,150,205 | 13,150,209 | 13,150,214 |
| 13,150,219 | 13,150,222 | 13,150,227 | 13,150,230 | 13,150,233 |
| 13,150,235 | 13,150,237 | 13,150,240 | 13,150,242 | 13,150,244 |
| 13,150,246 | 13,150,250 | 13,150,253 | 13,149,909 | 13,149,910 |
| 13,149,912 | 13,149,914 | 13,149,917 | 13,149,920 | 13,149,936 |
| 13,149,953 | 13,149,957 | 13,149,961 | 13,149,964 | 13,149,894 |
| 13,149,967 | 13,149,970 | 13,149,972 | 13,149,974 | 13,149,976 |
| 13,149,978 | 13,149,898 | 13,149,980 | 13,149,902 | 13,149,983 |
| 13,149,993 | 13,149,996 | 13,150,000 | 13,150,031 | 13,150,035 |
| 13,150,037 | 13,150,040 | 13,150,042 | 13,150,045 | 13,150,049 |
| 13,150,051 | 13,150,054 | 13,150,056 | 13,150,059 | 13,150,079 |
| 13,150,082 | 13,150,085 | 13,150,087 | 13,150,090 | 13,150,092 |
| 13,150,096 | 13,150,099 | 13,150,104 | 13,150,107 | 13,150,111 |
| 13,150,114 | 13,150,117 | 13,150,121 | 13,150,124 | 13,150,128 |
| 13,150,132 | 13,150,136 | 13,150,139 | 13,150,144 | 13,150,147 |
| 13,150,151 | 13,149,907 | 13,150,155 | 13,149,908 | 13,150,159 |
| 13,150,163 | 13,150,166 | 13,150,170 | 13,150,175 | 13,150,179 |
| 13,150,182 | 13,150,185 | 13,150,187 | 13,150,191 | 13,150,193 |
| 13,150,197 | 13,150,202 | 13,150,206 | 13,150,210 | 13,150,213 |
| 13,150,218 | 13,149,952 | 13,149,955 | 13,149,959 | 13,149,963 |
| 13,149,966 | 13,149,969 | 13,149,985 | 13,149,989 | 13,149,992 |
| 13,149,997 | 13,150,002 | 13,150,007 | 13,150,009 | 13,149,892 |
| 13,150,012 | 13,150,016 | 13,149,893 | 13,150,020 | 13,150,023 |
| 13,150,027 | 13,150,032 | 13,150,036 | 13,149,895 | 13,150,039 |
| 13,150,044 | 13,149,899 | 13,150,047 | 13,150,052 | 13,149,904 |
| 13,150,055 | 13,150,058 | 13,150,060 | 13,149,918 | 13,150,063 |
| 13,149,921 | 13,149,924 | 13,150,067 | 13,149,070 | 13,150,074 |
| 13,149,927 | 13,150,078 | 13,150,081 | 13,150,083 | 13,150,086 |
| 13,150,089 | 13,149,930 | 13,149,934 | 13,150,093 | 13,150,097 |
| 13,150,100 | 13,150,106 | 13,150,110 | 13,149,939 | 13,149,943 |
| 13,149,891 | 13,150,137 | 13,150,141 | 13,150,143 | 13,150,148 |
| 13,150,152 | 13,150,156 | 13,150,160 | 13,150,164 | 13,150,168 |
| 13,150,172 | 13,150,176 | 13,150,180 | 13,150,183 | 13,150,186 |
| 13,150,189 | 13,150,194 | 13,150,199 | 13,150,203 | 13,150,208 |
| 13,150,212 | 13,150,217 | 13,150,221 | 13,150,224 | 13,150,226 |
| 13,150,229 | 13,150,232 | 13,150,234 | 13,149,948 | |

BACKGROUND OF THE INVENTION

Molecular diagnostics has emerged as a field that offers the promise of early disease detection, potentially before symptoms have manifested. Molecular diagnostic testing is used to detect:

Inherited disorders
Acquired disorders
Infectious diseases
Genetic predisposition to health-related conditions.

With high accuracy and fast turnaround times, molecular diagnostic tests have the potential to reduce the occurrence of ineffective health care services, enhance patient outcomes, improve disease management and individualize patient care. Many of the techniques in molecular diagnostics are based on the detection and identification of specific nucleic acids, both deoxyribonucleic acid (DNA) and ribonucleic acid (RNA), extracted and amplified from a biological specimen (such as blood or saliva). The complementary nature of the nucleic acid bases allows short sequences of synthesized DNA (oligonucleotides) to bond (hybridize) to specific nucleic acid sequences for use in nucleic acid tests. If hybridization occurs, then the complementary sequence is present in the sample. This makes it possible, for example, to predict the disease a person will contract in the future, determine the identity and virulence of an infectious pathogen, or determine the response a person will have to a drug.

Nucleic Acid Based Molecular Diagnostic Test

A nucleic acid based test has four distinct steps:
1. Sample preparation
2. Nucleic acid extraction
3. Nucleic acid amplification (optional)
4. Detection Many sample types are used for genetic analysis, such as blood, urine, sputum and tissue samples. The diagnostic test determines the type of sample required as not all samples are representative of the disease process. These samples have a variety of constituents, but usually only one of these is of interest. For example, in blood, high concentrations of erythrocytes can inhibit the detection of a pathogenic organism. Therefore a purification and/or concentration step at the beginning of the nucleic acid test is often required.

Blood is one of the more commonly sought sample types. It has three major constituents: leukocytes (white blood cells), erythrocytes (red blood cells) and thrombocytes (platelets). The thrombocytes facilitate clotting and remain active in vitro. To inhibit coagulation, the specimen is mixed with an agent such as ethylenediaminetetraacetic acid (EDTA) prior to purification and concentration. Erythrocytes are usually removed from the sample in order to concentrate the target cells. In humans, erythrocytes account for approximately 99% of the cellular material but do not carry DNA as they have no nucleus. Furthermore, erythrocytes contain components such as haemoglobin that can interfere with the downstream nucleic acid amplification process (described below). Removal of erythrocytes can be achieved by differentially lysing the erythrocytes in a lysis solution, leaving remaining cellular material intact which can then be separated from the sample using centrifugation. This provides a concentration of the target cells from which the nucleic acids are extracted.

The exact protocol used to extract nucleic acids depends on the sample and the diagnostic assay to be performed. For example, the protocol for extracting viral RNA will vary considerably from the protocol to extract genomic DNA. However, extracting nucleic acids from target cells usually involves a cell lysis step followed by nucleic acid purification. The cell lysis step disrupts the cell and nuclear membranes, releasing the genetic material. This is often accomplished using a lysis detergent, such as sodium dodecyl sulfate, which also denatures the large amount of proteins present in the cells.

The nucleic acids are then purified with an alcohol precipitation step, usually ice-cold ethanol or isopropanol, or via a solid phase purification step, typically on a silica matrix in a column, resin or on paramagnetic beads in the presence of high concentrations of a chaotropic salt, prior to washing and then elution in a low ionic strength buffer. An optional step prior to nucleic acid precipitation is the addition of a protease which digests the proteins in order to further purify the sample.

Other lysis methods include mechanical lysis via ultrasonic vibration and thermal lysis where the sample is heated to 94° C. to disrupt cell membranes.

The target DNA or RNA may be present in the extracted material in very small amounts, particularly if the target is of pathogenic origin. Nucleic acid amplification provides the ability to selectively amplify (that is, replicate) specific targets present in low concentrations to detectable levels.

The most commonly used nucleic acid amplification technique is the polymerase chain reaction (PCR). PCR is well known in this field and comprehensive description of this type of reaction is provided in E. van Pelt-Verkuil et al., Principles and Technical Aspects of PCR Amplification, Springer, 2008.

PCR is a powerful technique that amplifies a target DNA sequence against a background of complex DNA. If RNA is to be amplified (by PCR), it must be first transcribed into cDNA (complementary DNA) using an enzyme called reverse transcriptase. Afterwards, the resulting cDNA is amplified by PCR.

PCR is an exponential process that proceeds as long as the conditions for sustaining the reaction are acceptable. The components of the reaction are:

1. pair of primers—short single strands of DNA with around 10-30 nucleotides complementary to the regions flanking the target sequence
2. DNA polymerase—a thermostable enzyme that synthesizes DNA
3. deoxyribonucleoside triphosphates (dNTPs)—provide the nucleotides that are incorporated into the newly synthesized DNA strand
4. buffer—to provide the optimal chemical environment for DNA synthesis PCR typically involves placing these reactants in a small tube (~10-50 microliters) containing the extracted nucleic acids. The tube is placed in a thermal cycler; an instrument that subjects the reaction to a series of different temperatures for varying amounts of time. The standard protocol for each thermal cycle involves a denaturation phase, an annealing phase, and an extension phase. The extension phase is sometimes referred to as the primer extension phase. In addition to such three-step protocols, two-step thermal protocols can be employed, in which the annealing and extension phases are combined. The denaturation phase typically involves raising the temperature of the reaction to 90-95° C. to denature the DNA strands; in the annealing phase, the temperature is lowered to ~50-60° C. for the primers to anneal; and then in the extension phase the temperature is raised to the optimal DNA polymerase activity temperature of 60-72° C. for primer extension. This process is repeated cyclically around 20-40 times, the end result being the creation of millions of copies of the target sequence between the primers.

There are a number of variants to the standard PCR protocol such as multiplex PCR, linker-primed PCR, direct PCR, tandem PCR, real-time PCR and reverse-transcriptase PCR, amongst others, which have been developed for molecular diagnostics.

Multiplex PCR uses multiple primer sets within a single PCR mixture to produce amplicons of varying sizes that are specific to different DNA sequences. By targeting multiple genes at once, additional information may be gained from a single test-run that otherwise would require several experiments. Optimization of multiplex PCR is more difficult though and requires selecting primers with similar annealing temperatures, and amplicons with similar lengths and base composition to ensure the amplification efficiency of each amplicon is equivalent.

Linker-primed PCR, also known as ligation adaptor PCR, is a method used to enable nucleic acid amplification of essentially all DNA sequences in a complex DNA mixture without the need for target-specific primers. The method firstly involves digesting the target DNA population with a suitable restriction endonuclease (enzyme). Double-stranded oligonucleotide linkers (also called adaptors) with a suitable overhanging end are then ligated to the ends of target DNA fragments using a ligase enzyme. Nucleic acid amplification is subsequently performed using oligonucleotide primers which are specific for the linker sequences. In this way, all fragments of the DNA source which are flanked by linker oligonucleotides can be amplified.

Direct PCR describes a system whereby PCR is performed directly on a sample without any, or with minimal, nucleic acid extraction. It has long been accepted that PCR reactions are inhibited by the presence of many components of unpurified biological samples, such as the haem component in blood. Traditionally, PCR has required extensive purification of the target nucleic acid prior to preparation of the reaction mixture. With appropriate changes to the chemistry and sample concentration, however, it is possible to perform PCR with minimal DNA purification, or direct PCR. Adjustments to the PCR chemistry for direct PCR include increased buffer strength, the use of polymerases which have high activity and processivity, and additives which chelate with potential polymerase inhibitors.

Tandem PCR utilises two distinct rounds of nucleic acid amplification to increase the probability that the correct amplicon is amplified. One form of tandem PCR is nested PCR in which two pairs of PCR primers are used to amplify a single locus in separate rounds of nucleic acid amplification. The first pair of primers hybridize to the nucleic acid sequence at regions external to the target nucleic acid sequence. The second pair of primers (nested primers) used in the second round of amplification bind within the first PCR product and produce a second PCR product containing the target nucleic acid, that will be shorter than the first one. The logic behind this strategy is that if the wrong locus were amplified by mistake during the first round of nucleic acid amplification, the probability is very low that it would also be amplified a second time by a second pair of primers and thus ensures specificity.

Real-time PCR, or quantitative PCR, is used to measure the quantity of a PCR product in real time. By using a fluorophore-containing probe or fluorescent dyes along with a set of standards in the reaction, it is possible to quantitate the starting amount of nucleic acid in the sample. This is particularly useful in molecular diagnostics where treatment options may differ depending on the pathogen load in the sample.

Reverse-transcriptase PCR (RT-PCR) is used to amplify DNA from RNA. Reverse transcriptase is an enzyme that reverse transcribes RNA into complementary DNA (cDNA), which is then amplified by PCR. RT-PCR is widely used in expression profiling, to determine the expression of a gene or to identify the sequence of an RNA transcript, including transcription start and termination sites. It is also used to amplify RNA viruses such as human immunodeficiency virus or hepatitis C virus.

Isothermal amplification is another form of nucleic acid amplification which does not rely on the thermal denaturation of the target DNA during the amplification reaction and hence does not require sophisticated machinery. Isothermal nucleic acid amplification methods can therefore be carried out in primitive sites or operated easily outside of a laboratory environment. A number of isothermal nucleic acid amplification methods have been described, including Strand Displacement Amplification, Transcription Mediated Amplification, Nucleic Acid Sequence Based Amplification, Recombinase Polymerase Amplification, Rolling Circle Amplification, Ramification Amplification, Helicase-Dependent Isothermal DNA Amplification and Loop-Mediated Isothermal Amplification.

Isothermal nucleic acid amplification methods do not rely on the continuing heat denaturation of the template DNA to produce single stranded molecules to serve as templates for further amplification, but instead rely on alternative methods such as enzymatic nicking of DNA molecules by specific restriction endonucleases, or the use of an enzyme to separate the DNA strands, at a constant temperature.

Strand Displacement Amplification (SDA) relies on the ability of certain restriction enzymes to nick the unmodified strand of hemi-modified DNA and the ability of a 5'-3' exonuclease-deficient polymerase to extend and displace the downstream strand. Exponential nucleic acid amplification is then achieved by coupling sense and antisense reactions in which strand displacement from the sense reaction serves as a template for the antisense reaction. The use of nickase enzymes which do not cut DNA in the traditional manner but produce a nick on one of the DNA strands, such as N. A1w1, N. BstNB1 and M1y1, are useful in this reaction. SDA has been improved by the use of a combination of a heat-stable restriction enzyme (Ava1) and heat-stable Exo-polymerase (Bst polymerase). This combination has been shown to increase amplification efficiency of the reaction from $10^8$ fold amplification to $10^{10}$ fold amplification so that it is possible using this technique to amplify unique single copy molecules.

Transcription Mediated Amplification (TMA) and Nucleic Acid Sequence Based Amplification (NASBA) use an RNA polymerase to copy RNA sequences but not corresponding genomic DNA. The technology uses two primers and two or three enzymes, RNA polymerase, reverse transcriptase and optionally RNase H (if the reverse transcriptase does not have RNase activity). One primer contains a promoter sequence for RNA polymerase. In the first step of nucleic acid amplification, this primer hybridizes to the target ribosomal RNA (rRNA) at a defined site. Reverse transcriptase creates a DNA copy of the target rRNA by extension from the 3' end of the promoter primer. The RNA in the resulting RNA:DNA duplex is degraded by the RNase activity of the reverse transcriptase if present or the additional RNase H. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons re-enters the process and serves as a template for a new round of replication.

In Recombinase Polymerase Amplification (RPA), the isothermal amplification of specific DNA fragments is achieved by the binding of opposing oligonucleotide primers to template DNA and their extension by a DNA polymerase. Heat is not required to denature the double-stranded DNA (dsDNA) template. Instead, RPA employs recombinase-primer complexes to scan dsDNA and facilitate strand exchange at cognate sites. The resulting structures are stabilised by single-stranded DNA binding proteins interacting with the displaced template strand, thus preventing the ejection of the primer by branch migration. Recombinase disassembly leaves the 3' end of the oligonucleotide accessible to a strand displacing DNA polymerase, such as the large fragment of Bacillus subtilis Pol I (Bsu), and primer extension ensues. Exponential nucleic acid amplification is accomplished by the cyclic repetition of this process.

Helicase-dependent amplification (HDA) mimics the in vivo system in that it uses a DNA helicase enzyme to generate single-stranded templates for primer hybridization and subsequent primer extension by a DNA polymerase. In the first step of the HDA reaction, the helicase enzyme traverses along the target DNA, disrupting the hydrogen bonds linking the two strands which are then bound by single-stranded binding proteins. Exposure of the single-stranded target region by the helicase allows primers to anneal. The DNA polymerase then extends the 3' ends of each primer using free deoxyribonucleoside triphosphates (dNTPs) to produce two DNA replicates. The two replicated dsDNA strands independently enter the next cycle of HDA, resulting in exponential nucleic acid amplification of the target sequence.

Other DNA-based isothermal techniques include Rolling Circle Amplification (RCA) in which a DNA polymerase extends a primer continuously around a circular DNA template, generating a long DNA product that consists of many repeated copies of the circle. By the end of the reaction, the polymerase generates many thousands of copies of the circular template, with the chain of copies tethered to the original target DNA. This allows for spatial resolution of target and rapid nucleic acid amplification of the signal. Up to $10^{12}$ copies of template can be generated in 1 hour. Ramification amplification is a variation of RCA and utilizes a closed circular probe (C-probe) or padlock probe and a DNA polymerase with a high processivity to exponentially amplify the C-probe under isothermal conditions.

Loop-mediated isothermal amplification (LAMP), offers high selectivity and employs a DNA polymerase and a set of four specially designed primers that recognize a total of six distinct sequences on the target DNA. An inner primer containing sequences of the sense and antisense strands of the target DNA initiates LAMP. The following strand displacement DNA synthesis primed by an outer primer releases a single-stranded DNA. This serves as template for DNA synthesis primed by the second inner and outer primers that hybridize to the other end of the target, which produces a stem-loop DNA structure. In subsequent LAMP cycling one inner primer hybridizes to the loop on the product and initiates displacement DNA synthesis, yielding the original stem-loop DNA and a new stem-loop DNA with a stem twice as long. The cycling reaction continues with accumulation of $10^9$ copies of target in less than an hour. The final products are stem-loop DNAs with several inverted repeats of the target and cauliflower-like structures with multiple loops formed by annealing between alternately inverted repeats of the target in the same strand.

After completion of the nucleic acid amplification, the amplified product must be analysed to determine whether the anticipated amplicon (the amplified quantity of target nucleic acids) was generated. The methods of analyzing the product range from simply determining the size of the amplicon through gel electrophoresis, to identifying the nucleotide composition of the amplicon using DNA hybridization.

Gel electrophoresis is one of the simplest ways to check whether the nucleic acid amplification process generated the anticipated amplicon. Gel electrophoresis uses an electric field applied to a gel matrix to separate DNA fragments. The negatively charged DNA fragments will move through the matrix at different rates, determined largely by their size. After the electrophoresis is complete, the fragments in the gel can be stained to make them visible. Ethidium bromide is a commonly used stain which fluoresces under UV light.

The size of the fragments is determined by comparison with a DNA size marker (a DNA ladder), which contains DNA fragments of known sizes, run on the gel alongside the amplicon. Because the oligonucleotide primers bind to specific sites flanking the target DNA, the size of the amplified product can be anticipated and detected as a band of known size on the gel. To be certain of the identity of the amplicon, or if several amplicons have been generated, DNA probe hybridization to the amplicon is commonly employed.

DNA hybridization refers to the formation of double-stranded DNA by complementary base pairing. DNA hybridization for positive identification of a specific amplification product requires the use of a DNA probe around 20 nucleotides in length. If the probe has a sequence that is complementary to the amplicon (target) DNA sequence, hybridization will occur under favourable conditions of temperature, pH and ionic concentration. If hybridization occurs, then the gene or DNA sequence of interest was present in the original sample.

Optical detection is the most common method to detect hybridization. Either the amplicons or the probes are labelled to emit light through fluorescence or electrochemiluminescence. These processes differ in the means of producing excited states of the light-producing moieties, but both enable covalent labelling of nucleotide strands. In electrochemiluminescence (ECL), light is produced by luminophore molecules or complexes upon stimulation with an electric current. In fluorescence, it is illumination with excitation light which leads to emission.

Fluorescence is detected using an illumination source which provides excitation light at a wavelength absorbed by the fluorescent molecule, and a detection unit. The detection unit comprises a photosensor (such as a photomultiplier tube or charge-coupled device (CCD) array) to detect the emitted signal, and a mechanism (such as a wavelength-selective filter) to prevent the excitation light from being included in the photosensor output. The fluorescent molecules emit Stokes-shifted light in response to the excitation light, and this emitted light is collected by the detection unit. Stokes shift is the frequency difference or wavelength difference between emitted light and absorbed excitation light.

ECL emission is detected using a photosensor which is sensitive to the emission wavelength of the ECL species being employed. For example, transition metal-ligand complexes emit light at visible wavelengths, so conventional photodiodes and CCDs are employed as photosensors. An advantage of ECL is that, if ambient light is excluded, the ECL emission can be the only light present in the detection system, which improves sensitivity.

Microarrays allow for hundreds of thousands of DNA hybridization experiments to be performed simultaneously. Microarrays are powerful tools for molecular diagnostics with the potential to screen for thousands of genetic diseases or detect the presence of numerous infectious pathogens in a single test. A microarray consists of many different DNA probes immobilized as spots on a substrate. The target DNA (amplicon) is first labelled with a fluorescent or luminescent molecule (either during or after nucleic acid amplification) and then applied to the array of probes. The microarray is incubated in a temperature controlled, humid environment for a number of hours or days while hybridization between the probe and amplicon takes place. Following incubation, the microarray must be washed in a series of buffers to remove unbound strands. Once washed, the microarray surface is dried using a stream of air (often nitrogen). The stringency of the hybridization and washes is critical. Insufficient stringency can result in a high degree of nonspecific binding. Excessive stringency can lead to a failure of appropriate binding, which results in diminished sensitivity. Hybridization is recognized by detecting light emission from the labelled amplicons which have formed a hybrid with complementary probes.

Fluorescence from microarrays is detected using a microarray scanner which is generally a computer controlled inverted scanning fluorescence confocal microscope which typically uses a laser for excitation of the fluorescent dye and a photosensor (such as a photomultiplier tube or CCD) to detect the emitted signal. The fluorescent molecules emit Stokes-shifted light (described above) which is collected by the detection unit.

The emitted fluorescence must be collected, separated from the unabsorbed excitation wavelength, and transported to the detector. In microarray scanners, a confocal arrangement is commonly used to eliminate out-of-focus information by means of a confocal pinhole situated at an image plane. This allows only the in-focus portion of the light to be detected. Light from above and below the plane of focus of the object is prevented from entering the detector, thereby increasing the signal to noise ratio. The detected fluorescent photons are converted into electrical energy by the detector which is subsequently converted to a digital signal. This digital signal translates to a number representing the intensity of fluorescence from a given pixel. Each feature of the array is made up of one or more such pixels. The final result of a scan is an image of the array surface. The exact sequence and position of every probe on the microarray is known, and so the hybridized target sequences can be identified and analysed simultaneously.

More information regarding fluorescent probes can be found at: http://www.premierbiosoft.com/tech_notes/FRET_probe.html and http://www.invitrogen.com/site/us/en/home/References/Molecular-Probes-The-Handbook/Technical-Notes-and-Product-Highlights/Fluorescence-Resonance-Energy-Transfer-FRET.html Point-of-Care Molecular Diagnostics Despite the advantages that molecular diagnostic tests offer, the growth of this type of testing in the clinical laboratory has been slower than expected and remains a minor part of the practice of laboratory medicine. This is primarily due to the complexity and costs associated with nucleic acid testing compared with tests based on methods not involving nucleic acids. The widespread adaptation of molecular diagnostics testing to the clinical setting is intimately tied to the development of instrumentation that significantly reduces the cost, provides a rapid and automated assay from start (specimen processing) to finish (generating a result) and operates without major intervention by personnel.

A point-of-care technology serving the physician's office, the hospital bedside or even consumer-based, at home, would offer many advantages including:
  rapid availability of results enabling immediate facilitation of treatment and improved quality of care.
  ability to obtain laboratory values from testing very small samples.
  reduced clinical workload.
  reduced laboratory workload and improved office efficiency by reducing administrative work.
  improved cost per patient through reduced length of stay of hospitalization, conclusion of outpatient consultation at the first visit, and reduced handling, storing and shipping of specimens.
  facilitation of clinical management decisions such as infection control and antibiotic use.

Lab-on-a-Chip (LOC) Based Molecular Diagnostics

Molecular diagnostic systems based on microfluidic technologies provide the means to automate and speed up molecular diagnostic assays. The quicker detection times are primarily due to the extremely low volumes involved, automation, and the low-overhead inbuilt cascading of the diagnostic process steps within a microfluidic device. Volumes in the nanoliter and microliter scale also reduce reagent consumption and cost. Lab-on-a-chip (LOC) devices are a common form of microfluidic device. LOC devices have MST structures within a MST layer for fluid processing integrated onto a single supporting substrate (usually silicon). Fabrication using the VLSI (very large scale integrated) lithographic techniques of the semiconductor industry keeps the unit cost of each LOC device very low. However, controlling fluid flow through the LOC device, adding reagents, controlling reaction conditions and so on necessitate bulky external plumbing and electronics. Connecting a LOC device to these external devices effectively restricts the use of LOC devices for molecular diagnostics to the laboratory setting. The cost of the external equipment and complexity of its operation precludes LOC-based molecular diagnostics as a practical option for point-of-care settings.

In view of the above, there is a need for a molecular diagnostic system based on a LOC device for use at point-of-care.

SUMMARY OF THE INVENTION

Accordingly, the present invention provides a microfluidic thermal bend actuated pressure pulse valve comprising:
  an inlet for receiving a flow of liquid;
  an outlet for outputting the flow of liquid;
  a meniscus anchor between the inlet and the outlet such that the flow from the inlet towards the outlet stops at the meniscus anchor where the liquid forms a meniscus;
  a movable member for contacting the liquid; and,
  a thermal expansion actuator for displacing the movable member to generate a pulse in the liquid to dislodge the meniscus such that the liquid flow towards the outlet resumes.

Preferably, during use, the liquid flow from the inlet to the meniscus anchor is via capillary action and the liquid flow immediately downstream of the meniscus anchor to the outlet is via capillary action.

Preferably, the movable member is configured for movement between a quiescent position and an actuated position displaced from the quiescent position and the meniscus anchor is an aperture configured to arrest the liquid flow by pinning the meniscus at the aperture.

Preferably, the movable member at least partially defines the aperture.

Preferably, the thermal actuator has a resistive element for causing differential thermal expansion to move the movable member.

Preferably, the microfluidic valve also has a single flow-path from the inlet to the outlet wherein the actuator reciprocates the movable member between the quiescent and displaced positions until the flow-path immediately downstream of the aperture is filled enough for capillary action to re-establish the liquid flow in the flow direction.

Preferably, the microfluidic valve also has;
  a channel formed in a supporting substrate for at least partially defining the flow-path;
  CMOS circuitry positioned between the channel and the supporting substrate for operatively controlling the actuator valve; and,
  at least one sensor responsive to the liquid flow wherein the at least one sensor provides feedback to the CMOS circuitry for use in the operative control of the actuator valve; wherein,
  the at least one sensor is a liquid sensor for sensing the presence or absence of liquid at a position in the channel.

Preferably, the aperture is a nozzle in the movable member.

Preferably, the movable member is a cantilevered structure with the nozzle at the free end and the resistive element between the nozzle and the fixed end.

Preferably, the movable member is formed in one wall of the channel such that in the quiescent position, an interior surface of the movable member is coplanar with an interior surface of the wall.

Preferably, the channel is overlaid with a cap defining a cap channel, the cap channel defining the flow-path immediately downstream of the aperture in the movable member such that reciprocation of the movable member fills the cap channel until capillary driven flow to the outlet resumes.

Preferably, the channel has a cross sectional area transverse to the flow direction less than 400 square microns.

Preferably, the thermal expansion actuator comprises at least two dissimilar materials.

Preferably, one of the at least two dissimilar materials is an electrical insulator.

Preferably, the resistive element is a layer of titanium nitride.

Preferably, the thermal actuator has a layer of silicon dioxide adjacent the titanium nitride layer.

The thermal bend actuated pressure pulse valves reliably and manufacturably provide microfluidic valving action, exploiting the intrinsic positive qualities of microfluidic device technologies and avoiding problematic aspects of such technologies.

BRIEF DESCRIPTION OF THE DRAWINGS

Preferred embodiments of the present invention will now be described by way of example only with reference to the accompanying drawings, in which.

FIG. 13 is an enlarged view of Inset AA shown in FIG. 6;

FIG. 14 is an enlarged view of Inset AB shown in FIG. 6;

FIG. 15 is an enlarged view of Inset AE shown in FIG. 13;

FIG. 53 is a further enlarged plan view of two hybridization chambers in isolation;

FIG. 54 is schematic section view of a single hybridization chamber;

FIG. 55 is an enlarged view of the humidifier illustrated in Inset AG shown in FIG. 6;

FIG. 56 is an enlarged view of Inset AD shown in FIG. 52;

FIG. 57 is an exploded perspective view of the LOC device within Inset AD;

FIG. 74 is an enlarged view of the evaporator shown in Inset AP of FIG. 55;

FIG. 77 is a schematic representation of a test module with a lancet;

FIG. 93 is an enlarged view of Inset DG shown in FIG. 92;

FIG. 94 is an enlarged view of Inset DH shown in FIG. 92;

DETAILED DESCRIPTION OF THE PREFERRED EMBODIMENTS

Overview

Figure 1:
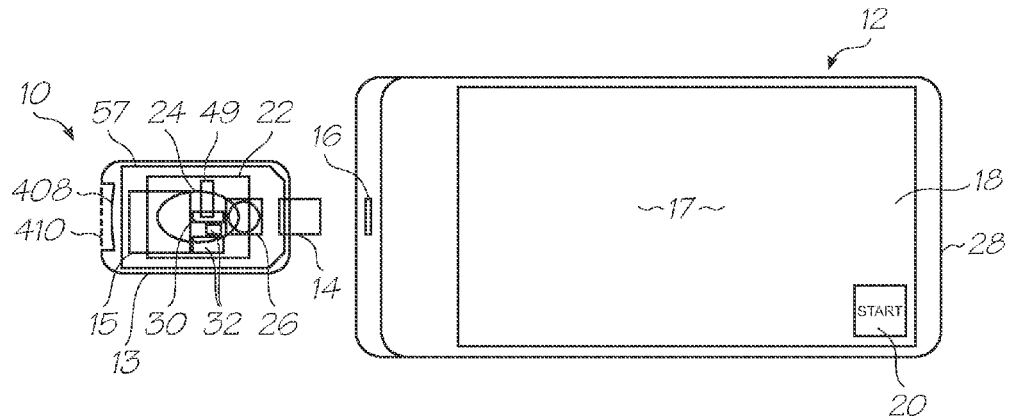
FIG. 1 shows a test module and test module reader configured for fluorescence detection.

This overview identifies the main components of a molecular diagnostic system that incorporates embodiments of the present invention. Comprehensive details of the system architecture and operation are set out later in the specification.

Referring to FIGS. 1, 2, 3, 103 and 104, the system has the following top level components:

Test modules 10 and 11 are the size of a typical USB memory key and very cheap to produce. Test modules 10 and 11 each contain a microfluidic device, typically in the form of a lab-on-a-chip (LOC) device 30 preloaded with reagents and typically more than 1000 probes for the molecular diagnostic assay (see FIGS. 1 and 103). Test module 10 schematically shown in FIG. 1 uses a fluorescence-based detection technique to identify target molecules, while test module 11 in FIG. 103 uses an electrochemiluminescence-based detection technique. The LOC device 30 has an integrated photosensor 44 for fluorescence or electrochemiluminescence detection (described in detail below). Both test modules 10 and 11 use a standard Micro-USB plug 14 for power, data and control, both have a printed circuit board (PCB) 57, and both have external power supply capacitors 32 and an inductor 15. The test modules 10 and 11 are both single-use only for mass production and distribution in sterile packaging ready for use.

The outer casing 13 has a macroreceptacle 24 for receiving the biological sample and a removable sterile sealing tape 22, preferably with a low tack adhesive, to cover the macroreceptacle prior to use. A membrane seal 408 with a membrane guard 410 forms part of the outer casing 13 to reduce dehumidification within the test module while providing pressure relief from small air pressure fluctuations. The membrane guard 410 protects the membrane seal 408 from damage.

Figure 3:
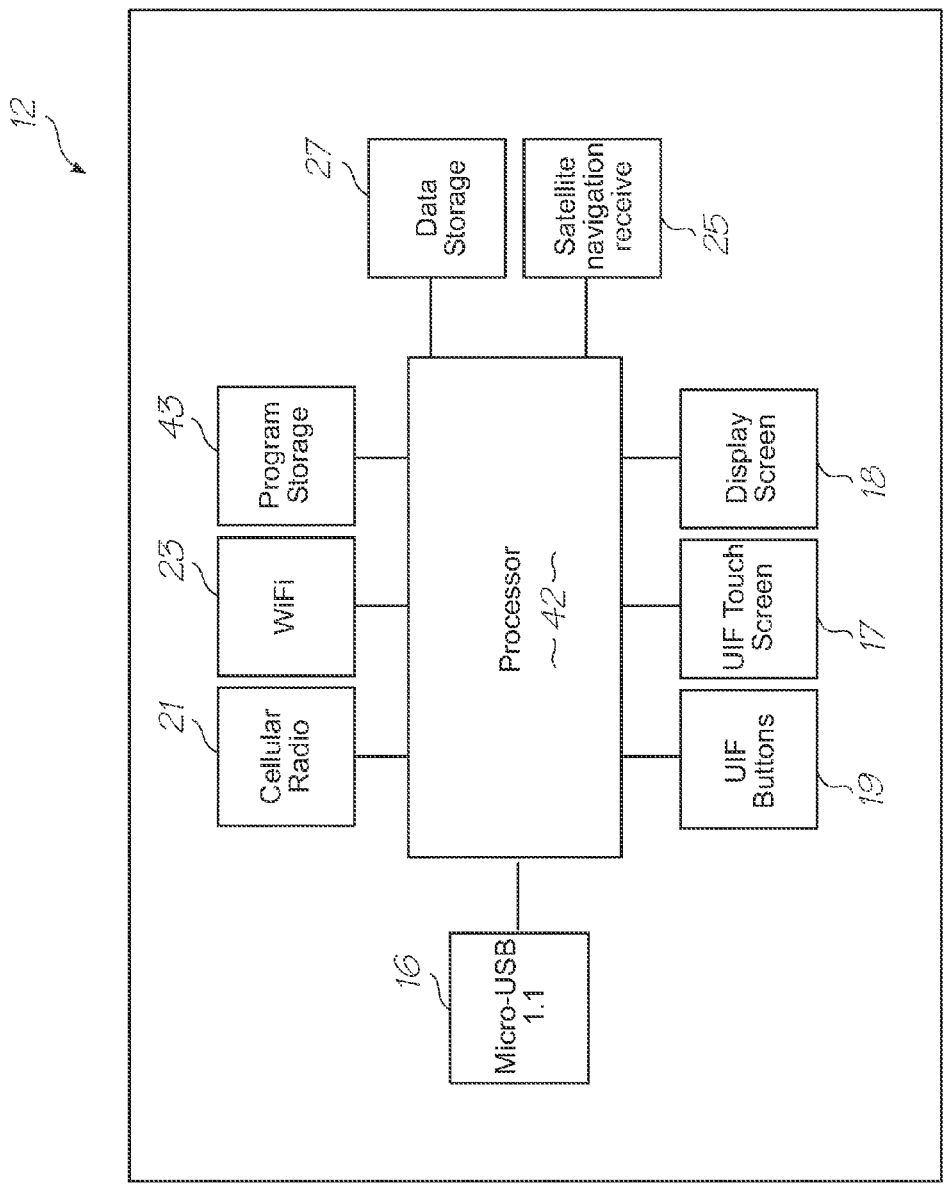
FIG. 3 is a schematic overview of the electronic components in the test module reader.
Figure 103:
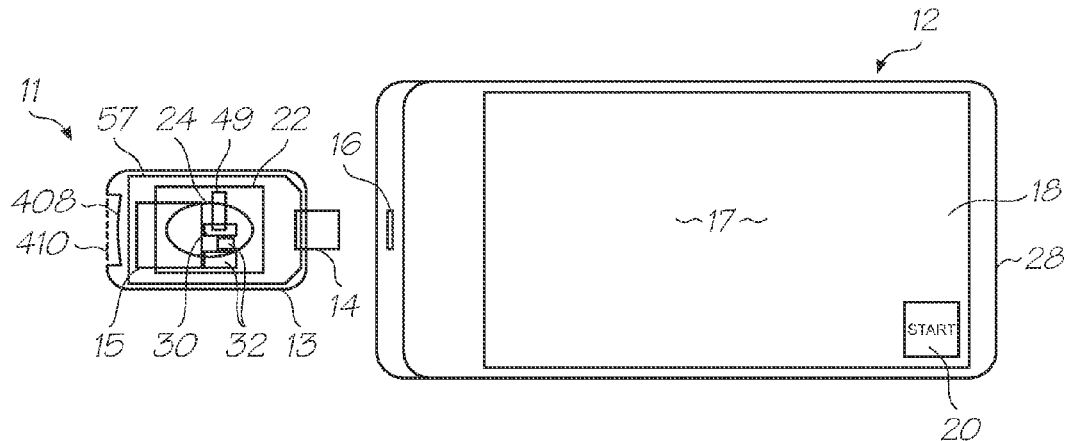
FIG. 103 shows a test module and test module reader configured for use with ECL detection.

Test module reader 12 powers the test module 10 or 11 via Micro-USB port 16. The test module reader 12 can adopt many different forms and a selection of these are described later. The version of the reader 12 shown in FIGS. 1, 3 and 103 is a smart phone embodiment. A block diagram of this reader 12 is shown in FIG. 3. Processor 42 runs application software from program storage 43. The processor 42 also interfaces with the display screen 18 and user interface (UI) touch screen 17 and buttons 19, a cellular radio 21, wireless network connection 23, and a satellite navigation system 25. The cellular radio 21 and wireless network connection 23 are used for communications. Satellite navigation system 25 is used for updating epidemiological databases with location data. The location data can, alternatively, be entered manually via the touch screen 17 or buttons 19. Data storage 27 holds genetic and diagnostic information, test results, patient information, assay and probe data for identifying each probe and its array position. Data storage 27 and program storage 43 may be shared in a common memory facility. Application software installed on the test module reader 12 provides analysis of results, along with additional test and diagnostic information.

To conduct a diagnostic test, the test module 10 (or test module 11) is inserted into the Micro-USB port 16 on the test module reader 12. The sterile sealing tape 22 is peeled back and the biological sample (in a liquid form) is loaded into the sample macroreceptacle 24. Pressing start button 20 initiates testing via the application software. The sample flows into the LOC device 30 and the on-board assay extracts, incubates, amplifies and hybridizes the sample nucleic acids (the target)

with presynthesized hybridization-responsive oligonucleotide probes. In the case of test module 10 (which uses fluorescence-based detection), the probes are fluorescently labelled and the LED 26 housed in the casing 13 provides the necessary excitation light to induce fluorescence emission from the hybridized probes (see FIGS. 1 and 2). In test module 11 (which uses electrochemiluminescence (ECL) detection), the LOC device 30 is loaded with ECL probes (discussed above) and the LED 26 is not necessary for generating the luminescent emission. Instead, electrodes 860 and 870 provide the excitation electrical current (see FIG. 104). The emission (fluorescent or luminescent) is detected using a photosensor 44 integrated into CMOS circuitry of each LOC device. The detected signal is amplified and converted to a digital output which is analyzed by the test module reader 12. The reader then displays the results.

The data may be saved locally and/or uploaded to a network server containing patient records. The test module 10 or 11 is removed from the test module reader 12 and disposed of appropriately.

Figure 105:
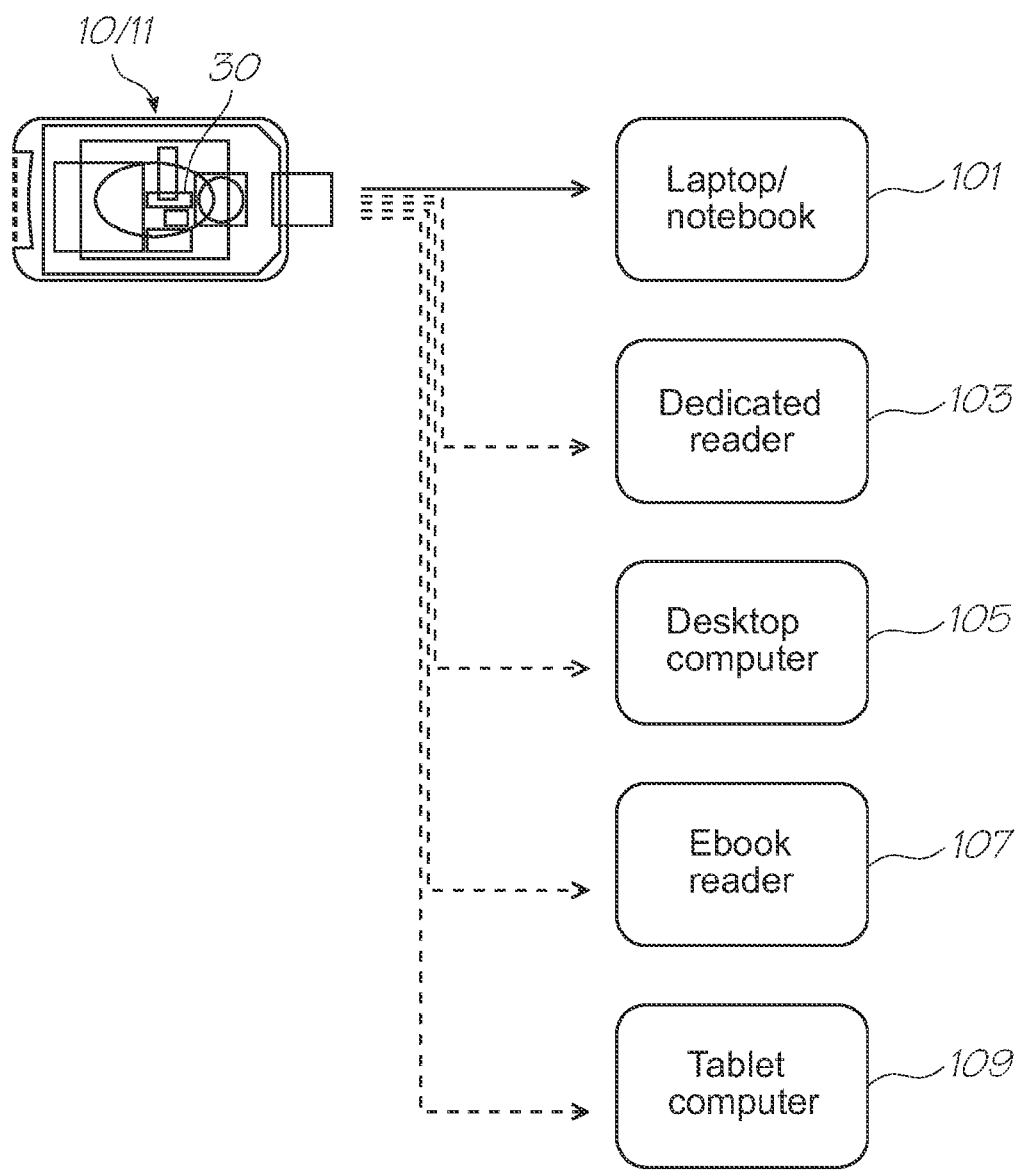
FIG. 105 shows a test module and alternative test module readers.

FIGS. 1, 3 and 103 show the test module reader 12 configured as a mobile phone/smart phone 28. In other forms, the test module reader is a laptop/notebook 101, a dedicated reader 103, an ebook reader 107, a tablet computer 109 or desktop computer 105 for use in hospitals, private practices or laboratories (see FIG. 105). The reader can interface with a range of additional applications such as patient records, billing, online databases and multi-user environments. It can also be interfaced with a range of local or remote peripherals such as printers and patient smart cards.

Figure 106:
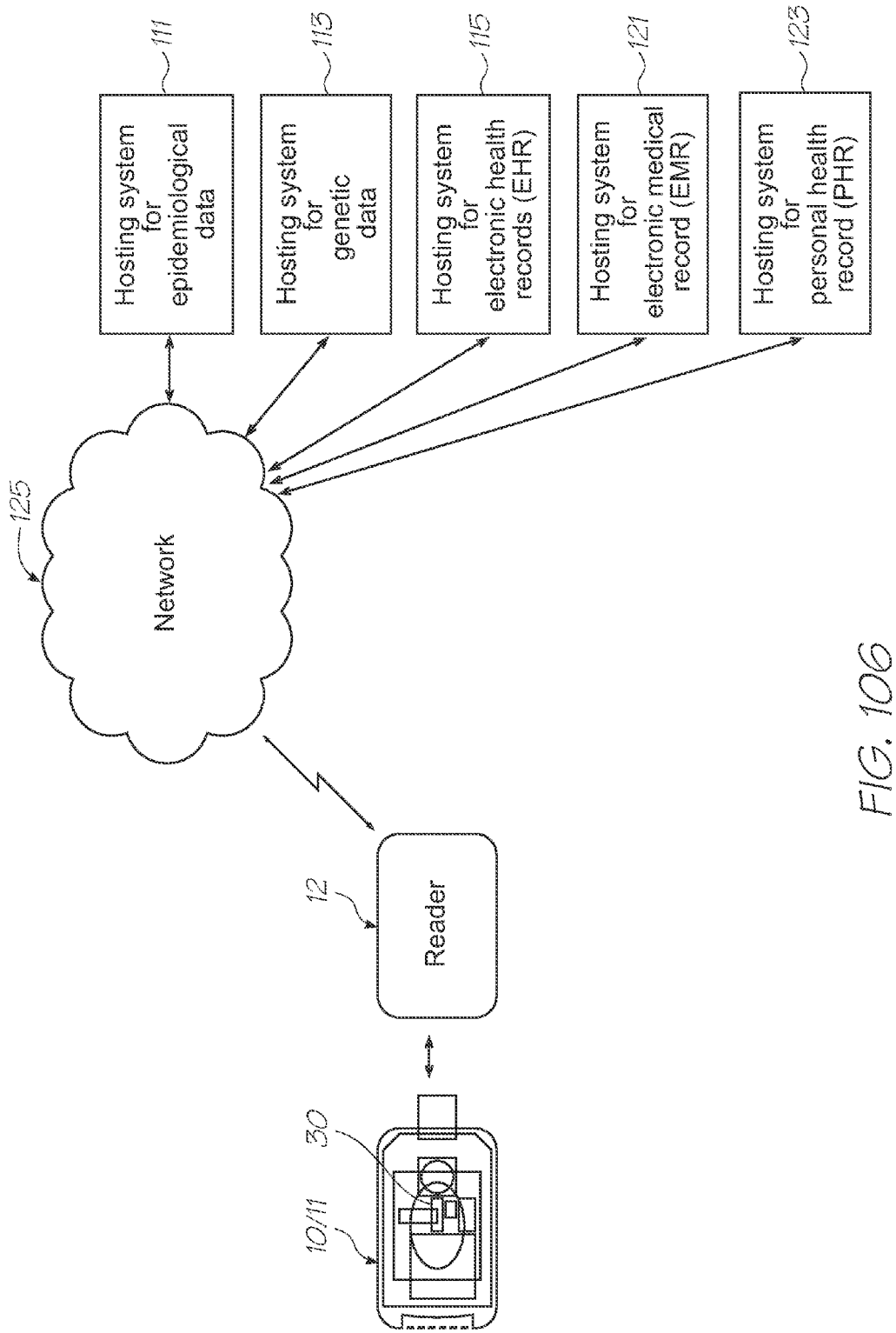
FIG. 106 shows a test module and test module reader along with the hosting system housing various databases.

Referring to FIG. 106, the data generated by the test module 10 can be used to update, via the reader 12 and network 125, the epidemiological databases hosted on the hosting system for epidemiological data 111, the genetic databases hosted on the hosting system for genetic data 113, the electronic health records hosted on the hosting system for electronic health records (EHR) 115, the electronic medical records hosted on the hosting system for electronic medical records (EMR) 121, and the personal health records hosted on the hosting system for personal health records (PHR) 123. Conversely, the epidemiological data hosted on the hosting system for epidemiological data 111, the genetic data hosted on the hosting system for genetic data 113, the electronic health records hosted on the hosting system for electronic health records (EHR) 115, the electronic medical records hosted on the hosting system for electronic medical records (EMR) 121, and the personal health records hosted on the hosting system for personal health records (PHR) 123, can be used to update, via network 125 and the reader 12, the digital memory in the LOC 30 of the test module 10.

Referring back to FIGS. 1, 2, 103 and 104 the reader 12 uses battery power in the mobile phone configuration. The mobile phone reader contains all test and diagnostic information preloaded. Data can also be loaded or updated via a number of wireless or contact interfaces to enable communications with peripheral devices, computers or online servers. A Micro-USB port 16 is provided for connection to a computer or mains power supply for battery recharge.

FIG. 77 shows an embodiment of the test module 10 used for tests that only require a positive or negative result for a particular target, such as testing whether a person is infected with, for example, H1N1 Influenza A virus. Only a purpose built USB power/indicator-only module 47 is adequate. No other reader or application software is necessary. An indicator 45 on the USB power/indicator-only module 47 signals positive or negative results. This configuration is well suited to mass screening.

Additional items supplied with the system may include a test tube containing reagents for pre-treatment of certain samples, along with spatula and lancet for sample collection. FIG. 77 shows an embodiment of the test module incorporating a spring-loaded, retractable lancet 390 and lancet release button 392 for convenience. A satellite phone can be used in remote areas.

Test Module Electronics

Figure 2:
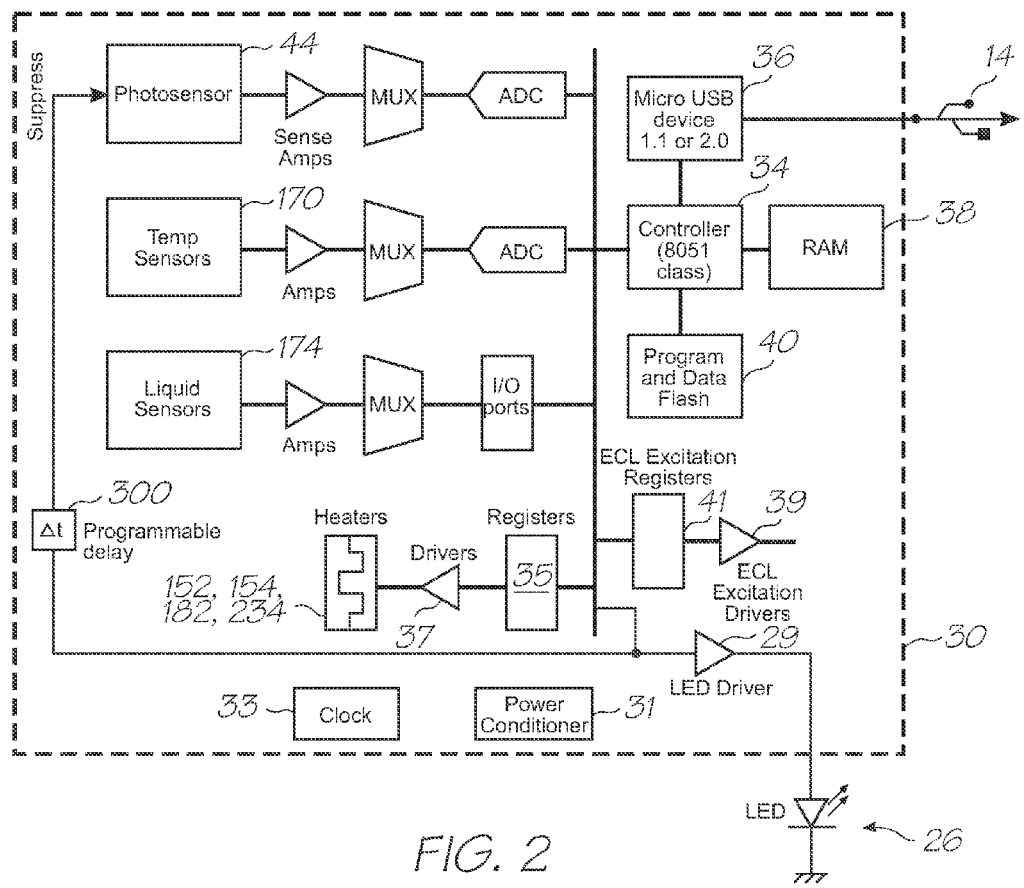
FIG. 2 is a schematic overview of the electronic components in the test module configured for fluorescence detection.
Figure 104:
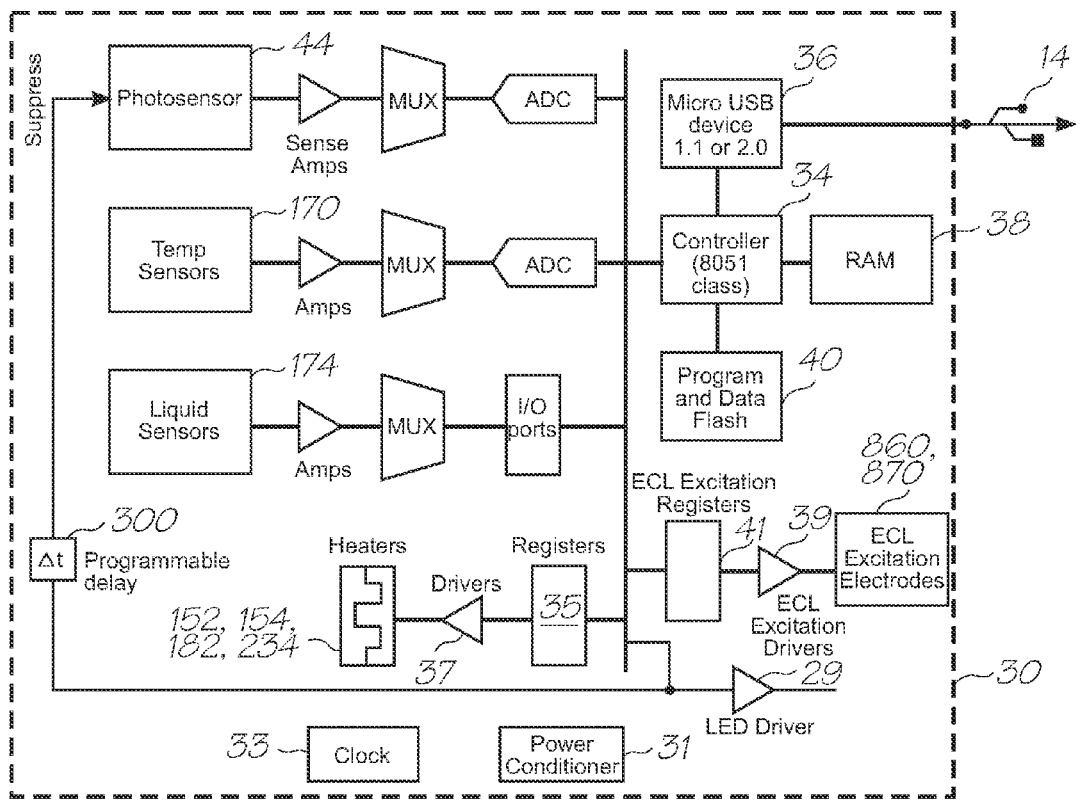
FIG. 104 is a schematic overview of the electronic components in the test module configured for use with ECL detection.

FIGS. 2 and 104 are block diagrams of the electronic components in the test modules 10 and 11, respectively. The CMOS circuitry integrated in the LOC device 30 has a USB device driver 36, a controller 34, a USB-compatible LED driver 29, clock 33, power conditioner 31, RAM 38 and program and data flash memory 40. These provide the control and memory for the entire test module 10 or 11 including the photosensor 44, the temperature sensors 170, the liquid sensors 174, and the various heaters 152, 154, 182, 234, together with associated drivers 37 and 39 and registers 35 and 41. Only the LED 26 (in the case of test module 10), external power supply capacitors 32 and the Micro-USB plug 14 are external to the LOC device 30. The LOC devices 30 include bond-pads for making connections to these external components. The RAM 38 and the program and data flash memory 40 have the application software and the diagnostic and test information (Flash/Secure storage, e.g. via encryption) for over 1000 probes. In the case of test module 11 configured for ECL detection, there is no LED 26 (see FIGS. 103 and 104). Data is encrypted by the LOC device 30 for secure storage and secure communication with an external device. The LOC devices 30 are loaded with electrochemiluminescent probes and the hybridization chambers each have a pair of ECL excitation electrodes 860 and 870.

Many types of test modules 10 are manufactured in a number of test forms, ready for off-the-shelf use. The differences between the test forms lie in the on board assay of reagents and probes.

Some examples of infectious diseases rapidly identified with this system include:

Influenza—Influenza virus A, B, C, Isavirus, Thogotovirus
Pneumonia—respiratory syncytial virus (RSV), adenovirus, metapneumovirus, *Streptococcus pneumoniae, Staphylococcus aureus*
Tuberculosis—*Mycobacterium tuberculosis, bovis, africanum, canetti*, and *microti*
*Plasmodium falciparum, Toxoplasma gondii* and other protozoan parasites
Typhoid—*Salmonella enterica* serovar *typhi*
Ebola virus
Human immunodeficiency virus (HIV)
Dengue Fever—Flavivirus
Hepatitis (A through E)
Hospital acquired infections—for example *Clostridium difficile*, Vancomycin resistant *Enterococcus*, and Methicillin resistant *Staphylococcus aureus*
Herpes simplex virus (HSV)
Cytomegalovirus (CMV)
Epstein-Ban virus (EBV)
Encephalitis—Japanese Encephalitis virus, Chandipura virus
Whooping cough—*Bordetella pertussis*
Measles—paramyxovirus
Meningitis—*Streptococcus pneumoniae* and *Neisseria meningitidis*
Anthrax—*Bacillus anthracis*

Some examples of genetic disorders identified with this system include:
Cystic fibrosis
Haemophilia
Sickle cell disease
Tay-Sachs disease
Haemochromatosis
Cerebral arteriopathy
Crohn's disease
Polycistic kidney disease
Congential heart disease
Rett syndrome A small selection of cancers identified by the diagnostic system include:
Ovarian
Colon carcinoma
Multiple endocrine neoplasia
Retinoblastoma
Turcot syndrome The above lists are not exhaustive and the diagnostic system can be configured to detect a much greater variety of diseases and conditions using nucleic acid and proteomic analysis.

DETAILED ARCHITECTURE OF SYSTEM COMPONENTS

LOC Device

The LOC device 30 is central to the diagnostic system. It rapidly performs the four major steps of a nucleic acid based molecular diagnostic assay, i.e. sample preparation, nucleic acid extraction, nucleic acid amplification, and detection, using a microfluidic platform. The LOC device also has alternative uses, and these are detailed later. As discussed above, test modules 10 and 11 can adopt many different configurations to detect different targets. Likewise, the LOC device 30 has numerous different embodiments tailored to the target(s) of interest. One form of the LOC device 30 is LOC device 301 for fluorescent detection of target nucleic acid sequences in the pathogens of a whole blood sample. For the purposes of illustration, the structure and operation of LOC device 301 is now described in detail with reference to FIGS. 4 to 26 and 27 to 57.

Figure 4:
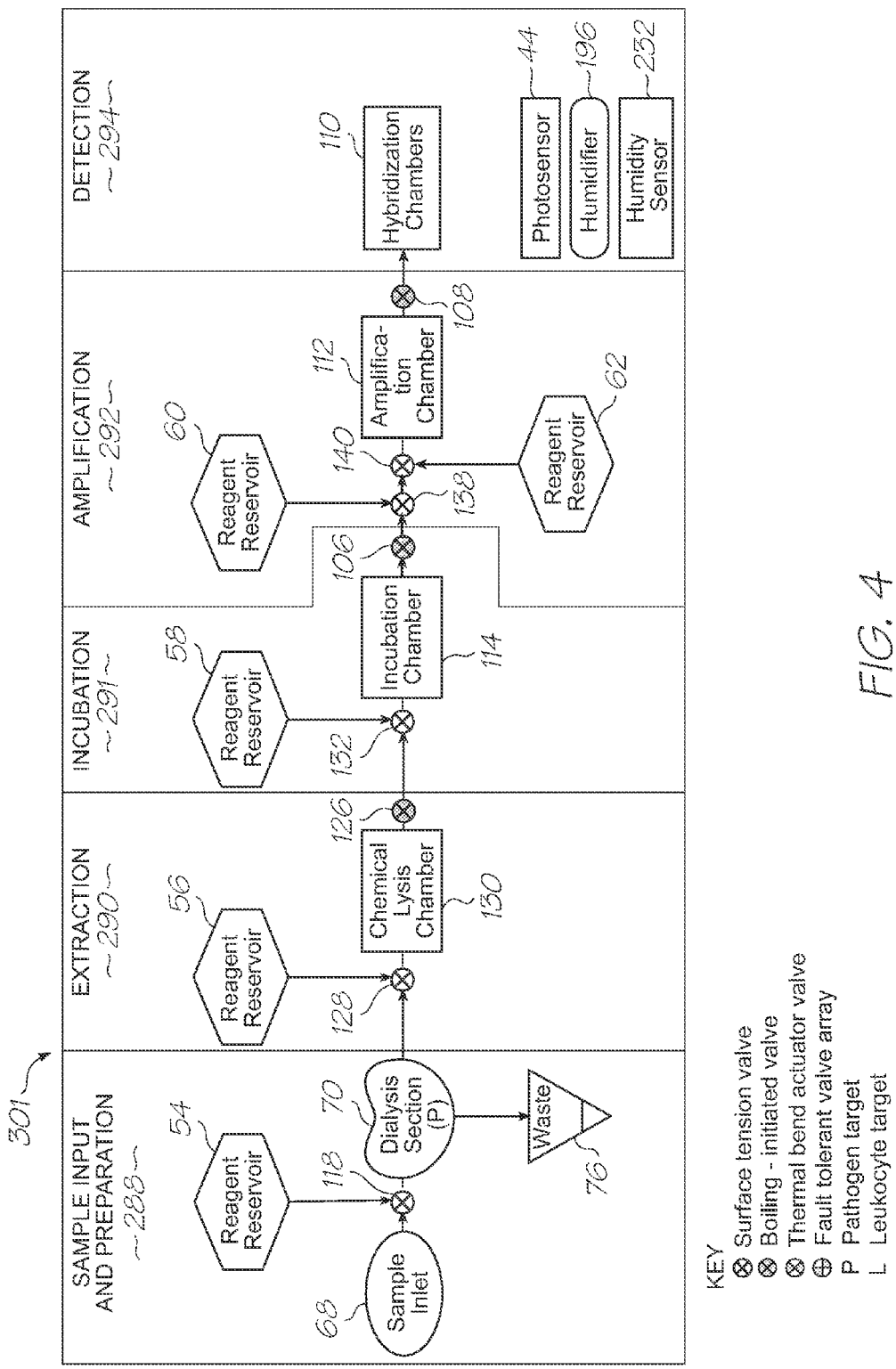
FIG. 4 is a schematic representation of the architecture of the LOC device.

FIG. 4 is a schematic representation of the architecture of the LOC device 301. For convenience, process stages shown in FIG. 4 are indicated with the reference numeral corresponding to the functional sections of the LOC device 301 that perform that process stage. The process stages associated with each of the major steps of a nucleic acid based molecular diagnostic assay are also indicated: sample input and preparation 288, extraction 290, incubation 291, amplification 292 and detection 294. The various reservoirs, chambers, valves and other components of the LOC device 301 will be described in more detail later.

Figure 5:
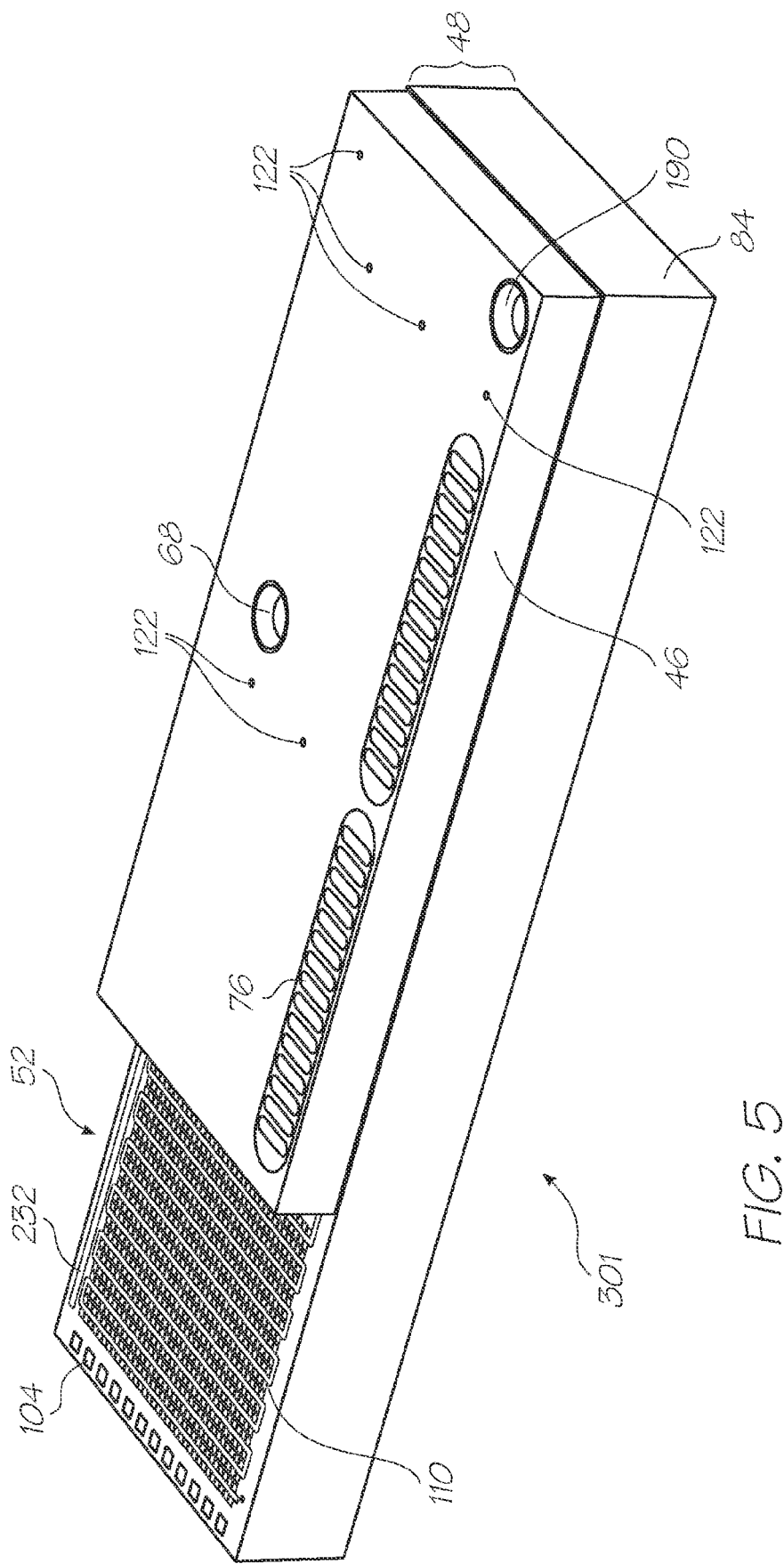
FIG. 5 is a perspective of the LOC device.

FIG. 5 is a perspective view of the LOC device 301. It is fabricated using high volume CMOS and MST (microsystems technology) manufacturing techniques. The laminar structure of the LOC device 301 is illustrated in the schematic (not to scale) partial section view of FIG. 12. The LOC device 301 has a silicon substrate 84 which supports the CMOS+ MST chip 48, comprising CMOS circuitry 86 and an MST layer 87, with a cap 46 overlaying the MST layer 87. For the purposes of this patent specification, the term 'MST layer' is a reference to a collection of structures and layers that process the sample with various reagents. Accordingly, these structures and components are configured to define flow-paths with characteristic dimensions that will support capillary driven flow of liquids with physical characteristics similar to those of the sample during processing. In light of this, the MST layer and components are typically fabricated using surface micromachining techniques and/or bulk micromachining techniques. However, other fabrication methods can also produce structures and components dimensioned for capillary driven flows and processing very small volumes. The specific embodiments described in this specification show the MST layer as the structures and active components supported on the CMOS circuitry 86, but excluding the features of the cap 46. However, the skilled addressee will appreciate that the MST layer need not have underlying CMOS or indeed an overlying cap in order for it to process the sample.

The overall dimensions of the LOC device shown in the following figures are 1760 µm×5824 µm. Of course, LOC devices fabricated for different applications may have different dimensions.

Figure 6:
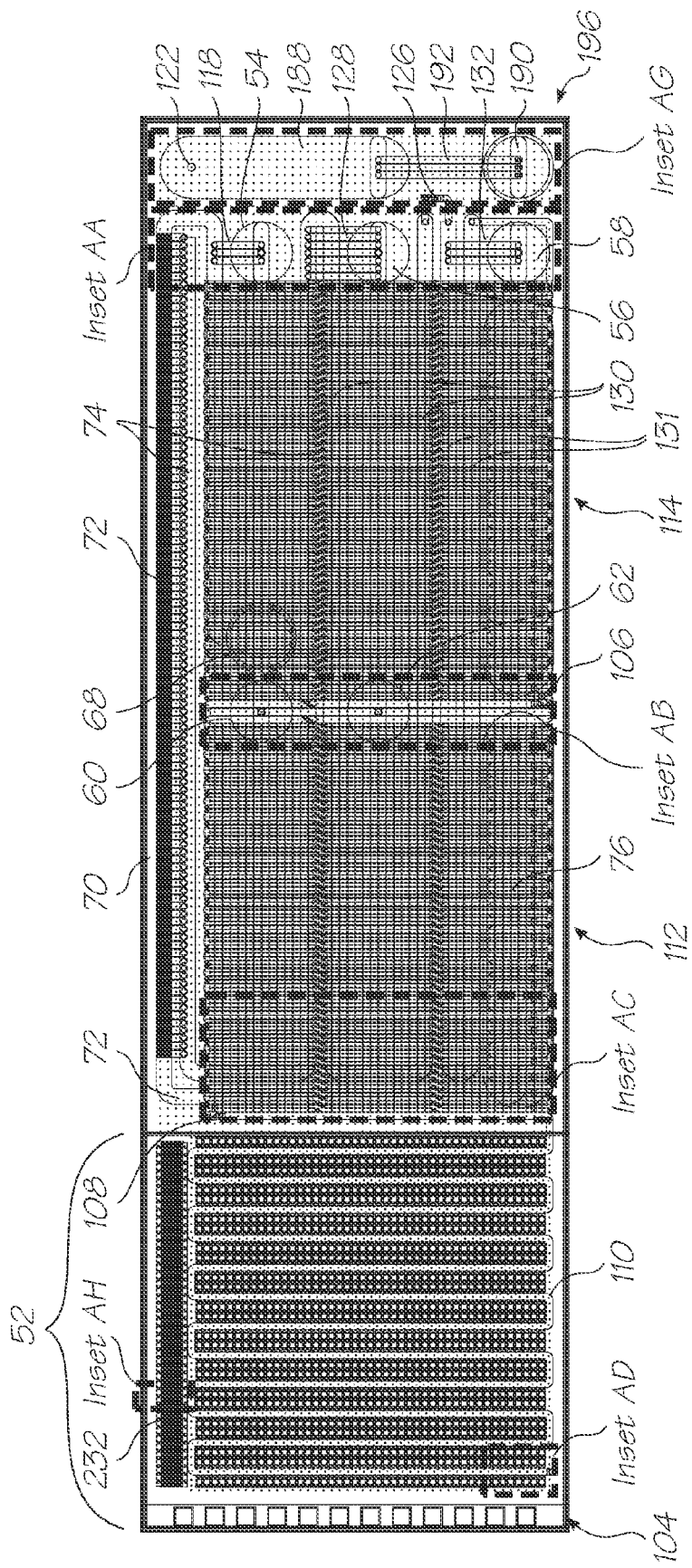
FIG. 6 is a plan view of the LOC device with features and structures from all layers superimposed on each other.
Figure 11:
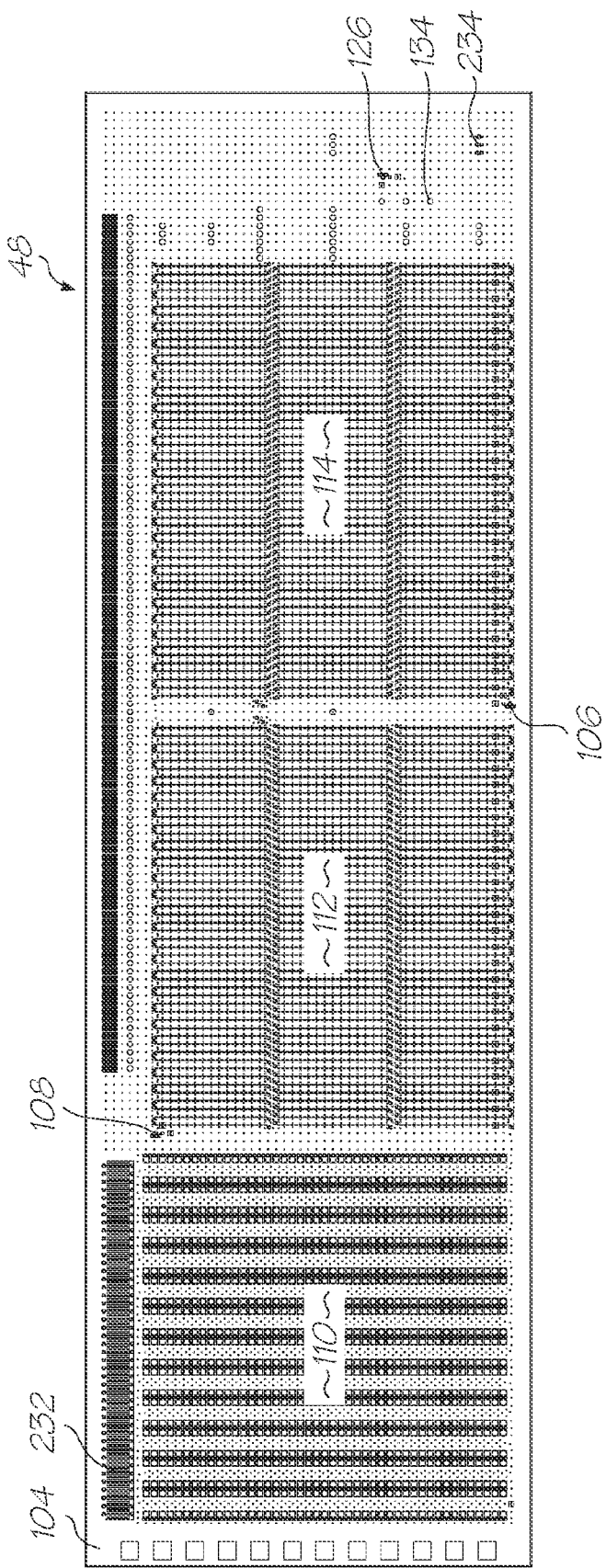
FIG. 11 is a plan view of the LOC device showing the structures of the CMOS+MST device in isolation.

FIG. 6 shows the features of the MST layer 87 superimposed with the features of the cap. Insets AA to AD, AG and AH shown in FIG. 6 are enlarged in FIGS. 13, 14, 35, 56, 55 and 63, respectively, and described in detail below for a comprehensive understanding of each structure within the LOC device 301. FIGS. 7 to 10 show the features of the cap 46 in isolation while FIG. 11 shows the CMOS+MST device 48 structures in isolation.

Laminar Structure

Figure 12:
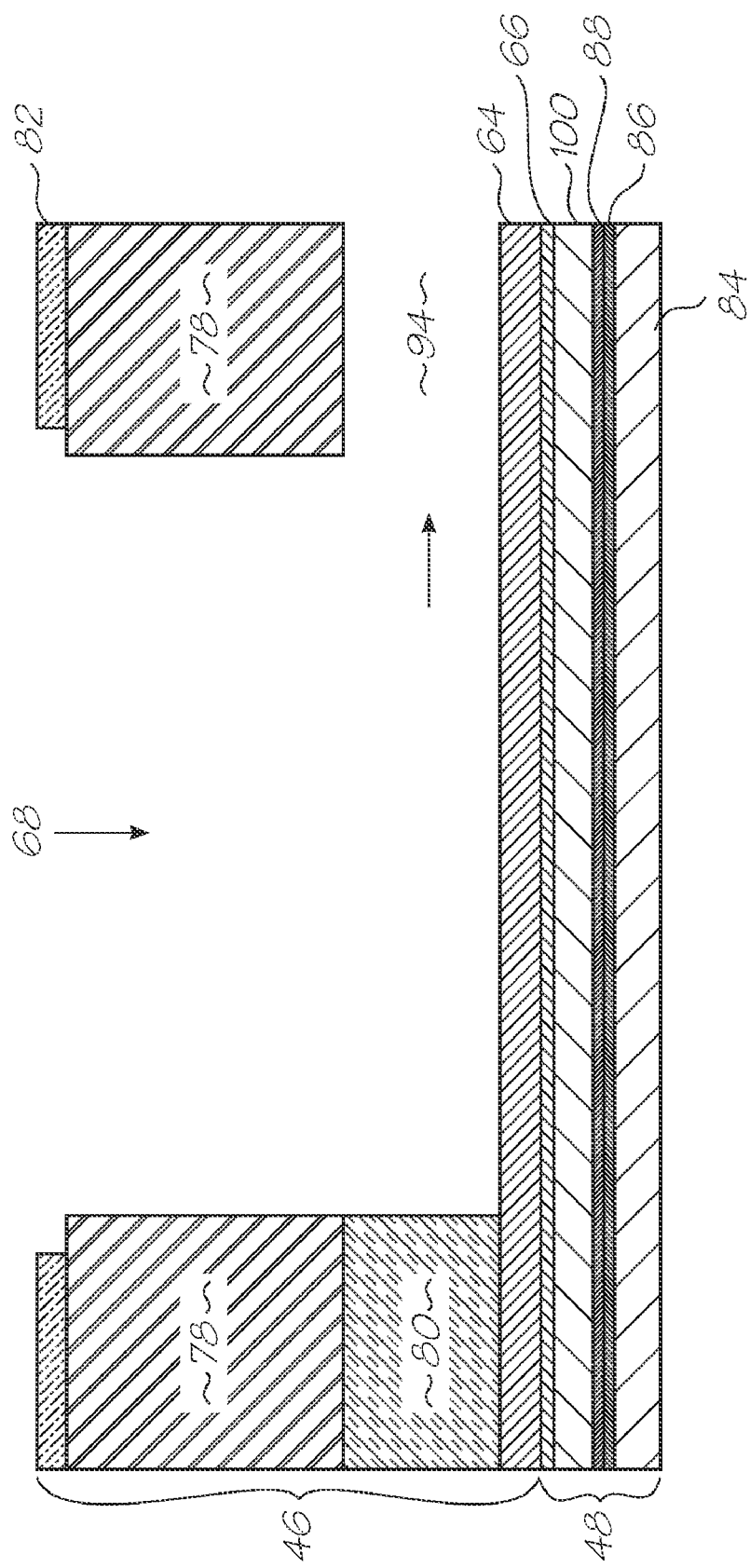
FIG. 12 is a schematic section view of the LOC device at the sample inlet.
Figure 22:
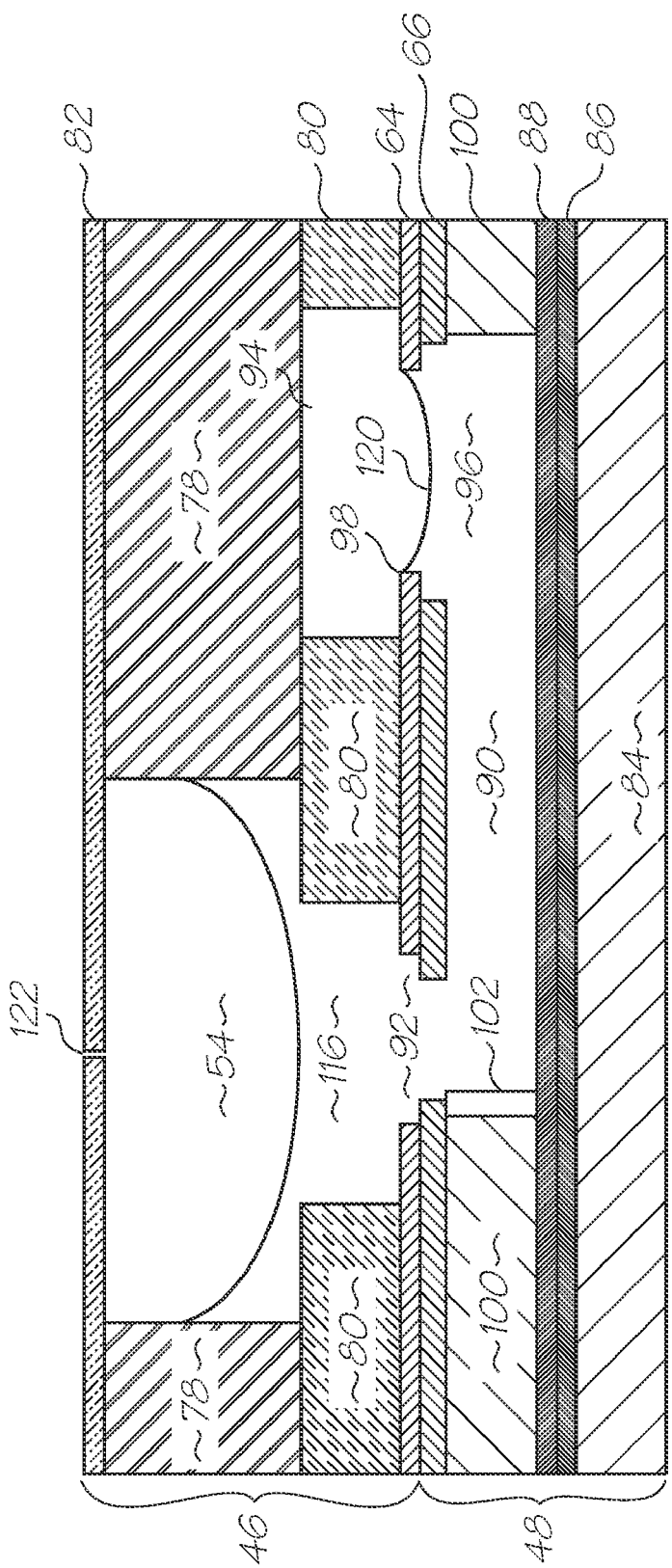
FIG. 22 is schematic section view of the lysis reagent reservoir shown in FIG. 21.

FIGS. 12 and 22 are sketches that diagrammatically show the laminar structure of the CMOS+MST device 48, the cap 46 and the fluidic interaction between the two. The figures are not to scale for the purposes of illustration. FIG. 12 is a schematic section view through the sample inlet 68 and FIG. 22 is a schematic section through the reservoir 54. As best shown in FIG. 12, the CMOS+MST device 48 has a silicon substrate 84 which supports the CMOS circuitry 86 that operates the active elements within the MST layer 87 above. A passivation layer 88 seals and protects the CMOS layer 86 from the fluid flows through the MST layer 87.

Fluid flows through both the cap channels 94 and the MST channels 90 (see for example FIGS. 7 and 16) in the cap layer 46 and MST channel layer 100, respectively. Cell transport occurs in the larger channels 94 fabricated in the cap 46, while biochemical processes are carried out in the smaller MST channels 90. Cell transport channels are sized so as to be able to transport cells in the sample to predetermined sites in the MST channels 90. Transportation of cells with sizes greater than 20 microns (for example, certain leukocytes) requires channel dimensions greater than 20 microns, and therefore a cross sectional area transverse to the flow of greater than 400 square microns. MST channels, particularly at locations in the LOC where transport of cells is not required, can be significantly smaller.

It will be appreciated that cap channel 94 and MST channel 90 are generic references and particular MST channels 90 may also be referred to as (for example) heated microchannels or dialysis MST channels in light of their particular function. MST channels 90 are formed by etching through a MST channel layer 100 deposited on the passivation layer 88 and patterned with photoresist. The MST channels 90 are enclosed by a roof layer 66 which forms the top (with respect to the orientation shown in the figures) of the CMOS+MST device 48.

Despite sometimes being shown as separate layers, the cap channel layer 80 and the reservoir layer 78 are formed from a unitary piece of material. Of course, the piece of material may also be non-unitary. This piece of material is etched from both sides in order to form a cap channel layer 80 in which the cap channels 94 are etched and the reservoir layer 78 in which the reservoirs 54, 56, 58, 60 and 62 are etched. Alternatively, the reservoirs and the cap channels are formed by a micromolding process. Both etching and micromolding techniques are used to produce channels with cross sectional areas transverse to the flow as large as 20,000 square microns, and as small as 8 square microns.

At different locations in the LOC device, there can be a range of appropriate choices for the cross sectional area of the channel transverse to the flow. Where large quantities of sample, or samples with large constituents, are contained in the channel, a cross-sectional area of up to 20,000 square microns (for example, a 200 micron wide channel in a 100 micron thick layer) is suitable. Where small quantities of liquid, or mixtures without large cells present, are contained in the channel, a very small cross sectional area transverse to the flow is preferable.

A lower seal 64 encloses the cap channels 94 and the upper seal layer 82 encloses the reservoirs 54, 56, 58, 60 and 62.

Figure 76:
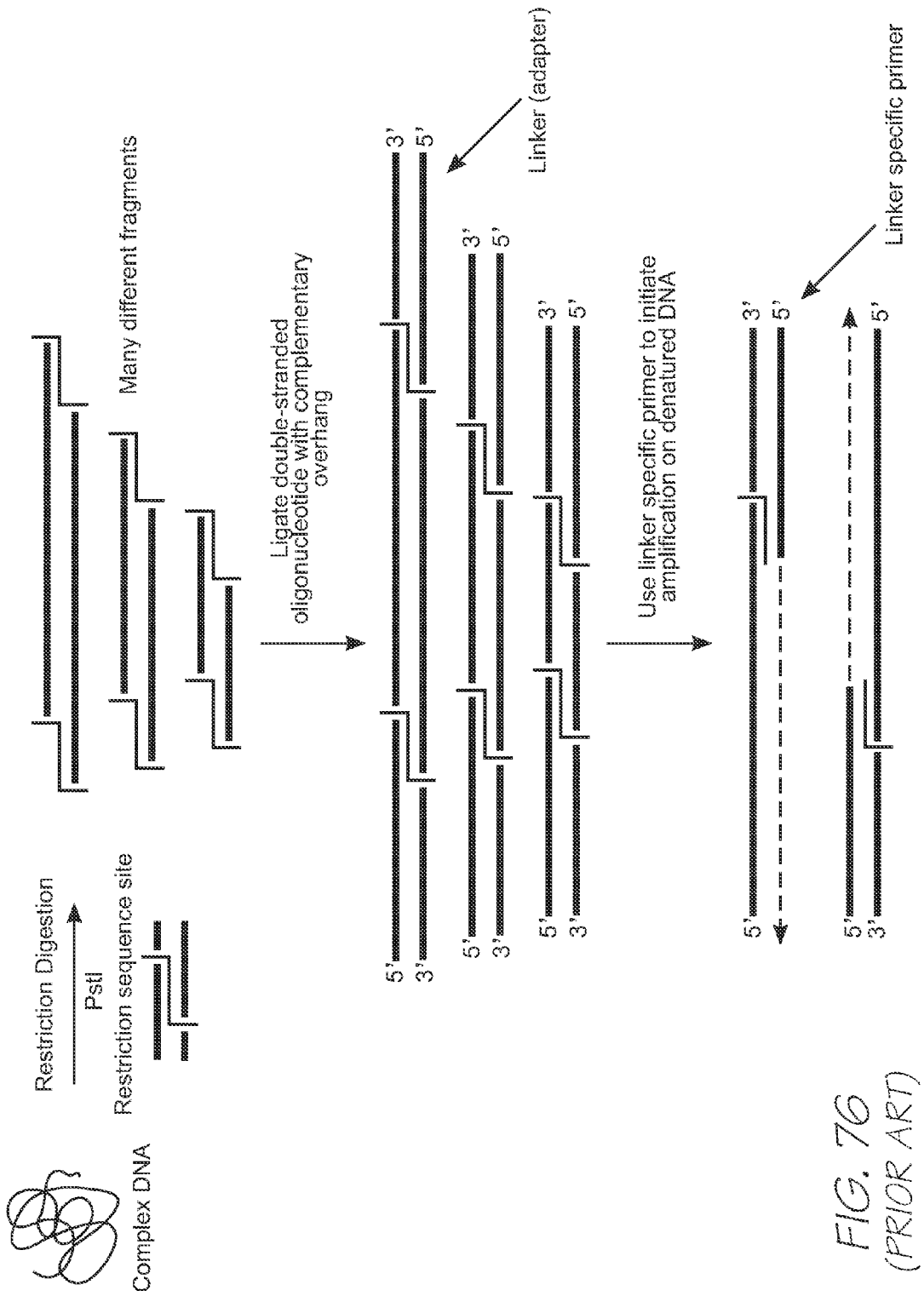
FIG. 76 is a diagram of linker-primed PCR.

The five reservoirs 54, 56, 58, 60 and 62 are preloaded with assay-specific reagents. In the embodiment described here, the reservoirs are preloaded with the following reagents, but other reagents can easily be substituted:
  reservoir 54: anticoagulant with option to include erythrocyte lysis buffer
  reservoir 56: lysis reagent
  reservoir 58: restriction enzymes, ligase and linkers (for linker-primed PCR (see FIG. 76, extracted from T. Stachan et al., Human Molecular Genetics 2, Garland Science, N.Y. and London, 1999))
  reservoir 60: amplification mix (dNTPs, primers, buffer) and
  reservoir 62: DNA polymerase.

The cap 46 and the CMOS+MST layers 48 are in fluid communication via corresponding openings in the lower seal 64 and the roof layer 66. These openings are referred to as uptakes 96 and downtakes 92 depending on whether fluid is flowing from the MST channels 90 to the cap channels 94 or vice versa.

LOC Device Operation

The operation of the LOC device 301 is described below in a step-wise fashion with reference to analysing pathogenic DNA in a blood sample. Of course, other types of biological or non-biological fluid are also analysed using an appropriate set, or combination, of reagents, test protocols, LOC variants and detection systems. Referring back to FIG. 4, there are five major steps involved in analysing a biological sample, comprising sample input and preparation 288, nucleic acid extraction 290, nucleic acid incubation 291, nucleic acid amplification 292 and detection and analysis 294.

Figure 7:
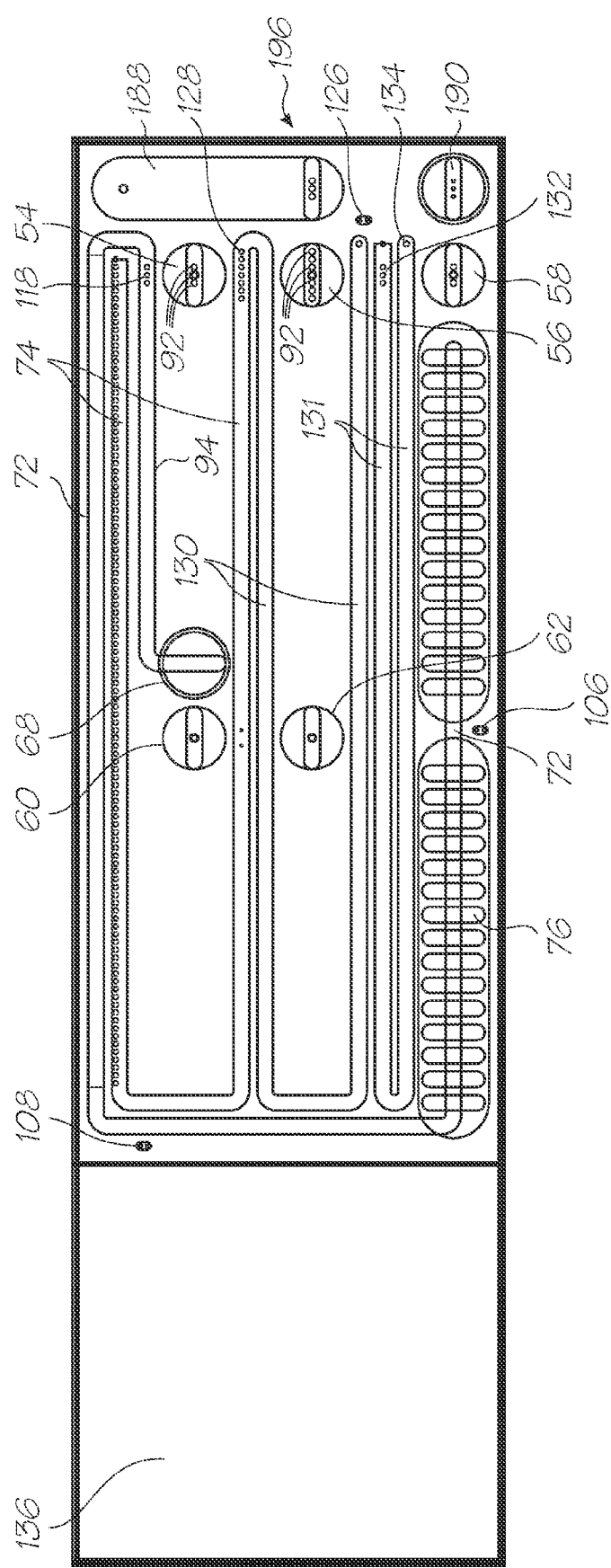
FIG. 7 is a plan view of the LOC device with the structures of the cap shown in isolation.
Figure 8:
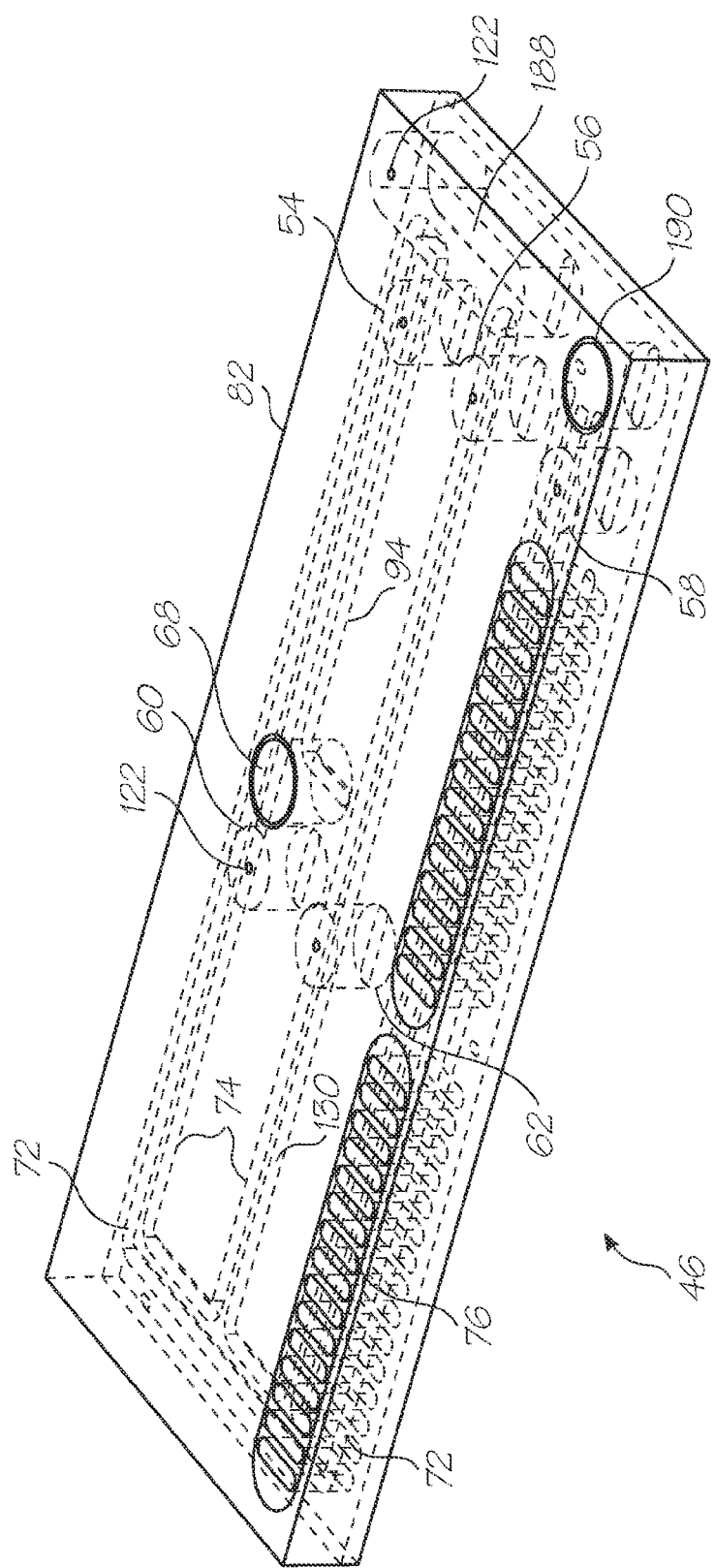
FIG. 8 is a top perspective of the cap with internal channels and reservoirs shown in dotted line.
Figure 9:
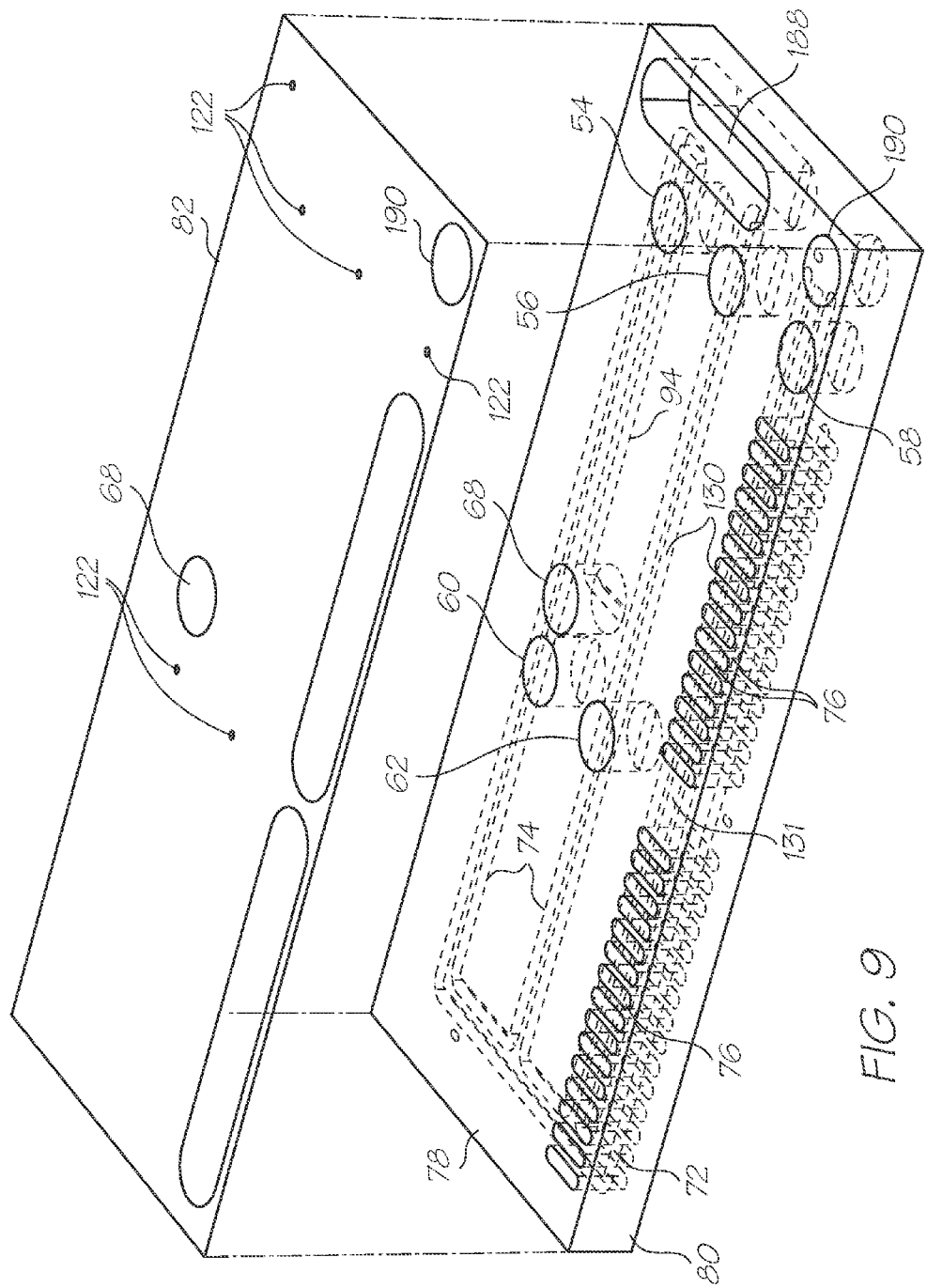
FIG. 9 is an exploded top perspective of the cap with internal channels and reservoirs shown in dotted line.
Figure 10:
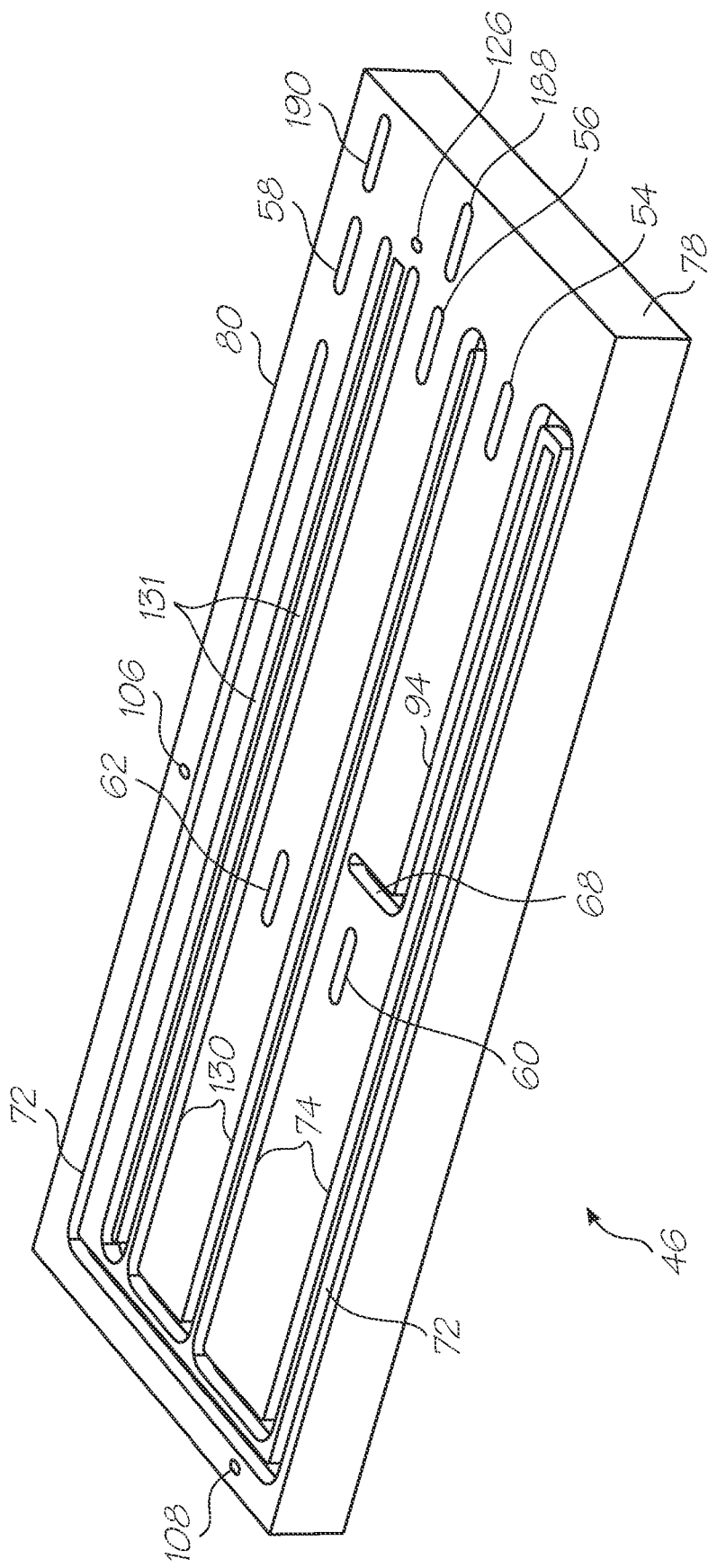
FIG. 10 is a bottom perspective of the cap showing the configuration of the top channels.

The sample input and preparation step 288 involves mixing the blood with an anticoagulant 116 and then separating pathogens from the leukocytes and erythrocytes with the pathogen dialysis section 70. As best shown in FIGS. 7 and 12, the blood sample enters the device via the sample inlet 68. Capillary action draws the blood sample along the cap channel 94 to the reservoir 54. Anticoagulant is released from the reservoir 54 as the sample blood flow opens its surface tension valve 118 (see FIGS. 15 and 22). The anticoagulant prevents the formation of clots which would block the flow.

As best shown in FIG. 22, the anticoagulant 116 is drawn out of the reservoir 54 by capillary action and into the MST channel 90 via the downtake 92. The downtake 92 has a capillary initiation feature (CIF) 102 to shape the geometry of the meniscus such that it does not anchor to the rim of the downtake 92. Vent holes 122 in the upper seal 82 allows air to replace the anticoagulant 116 as it is drawn out of the reservoir 54.

The MST channel 90 shown in FIG. 22 is part of a surface tension valve 118. The anticoagulant 116 fills the surface tension valve 118 and pins a meniscus 120 to the uptake 96 to a meniscus anchor 98. Prior to use, the meniscus 120 remains pinned at the uptake 96 so the anticoagulant does not flow into the cap channel 94. When the blood flows through the cap channel 94 to the uptake 96, the meniscus 120 is removed and the anticoagulant is drawn into the flow.

Figure 16:
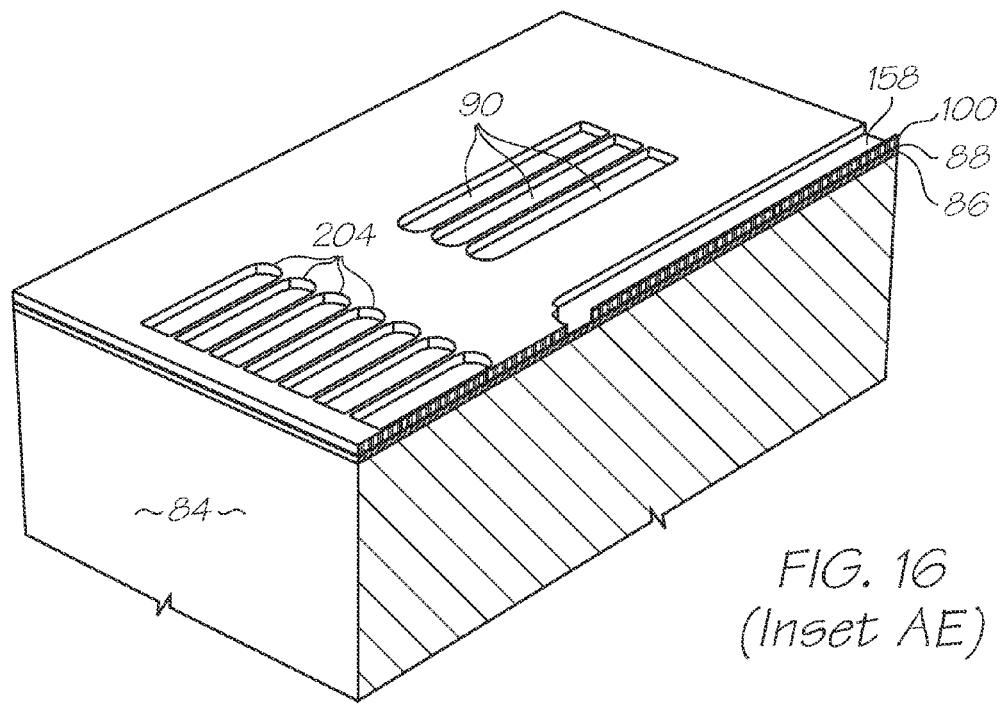
FIG. 16 is a partial perspective illustrating the laminar structure of the LOC device within Inset AE.
Figure 17:
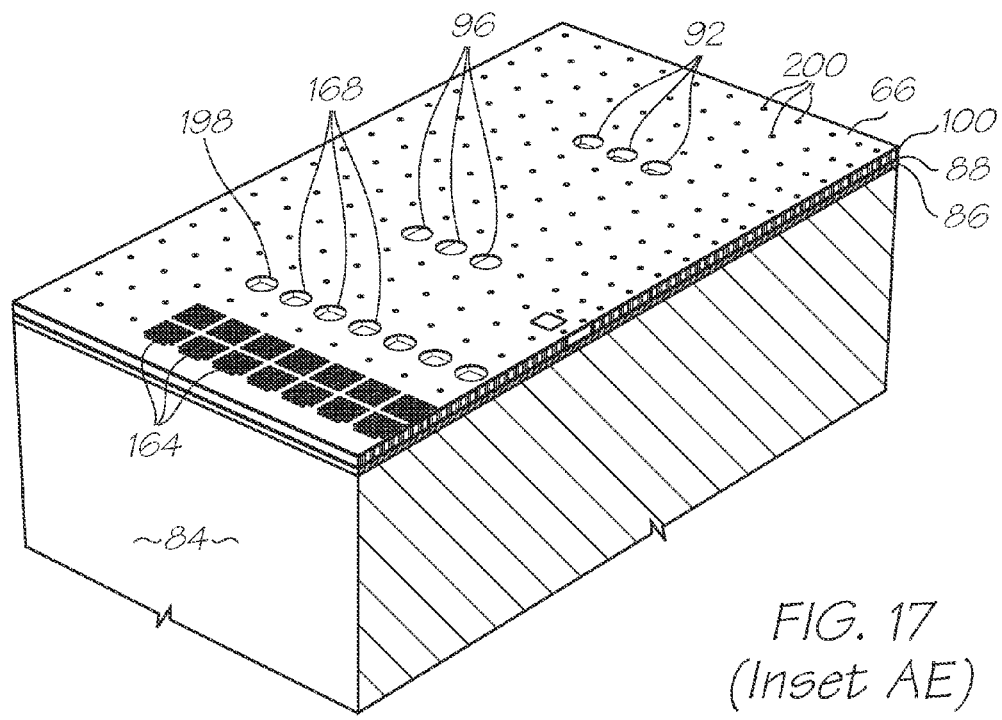
FIG. 17 is a partial perspective illustrating the laminar structure of the LOC device within Inset AE.
Figure 18:
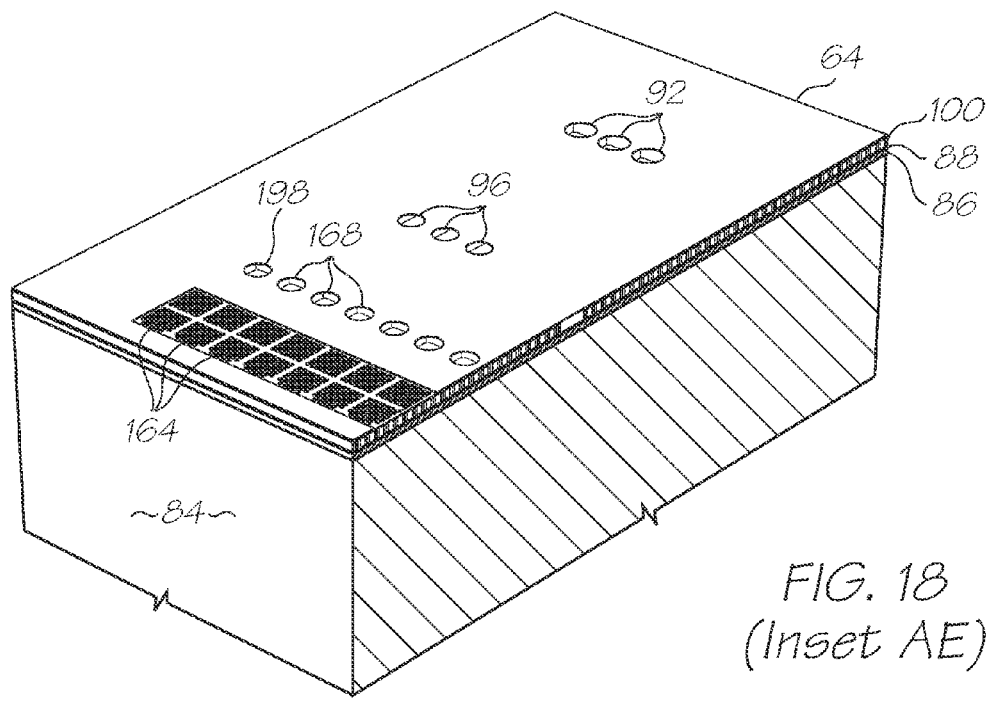
FIG. 18 is a partial perspective illustrating the laminar structure of the LOC device within Inset AE.
Figure 19:
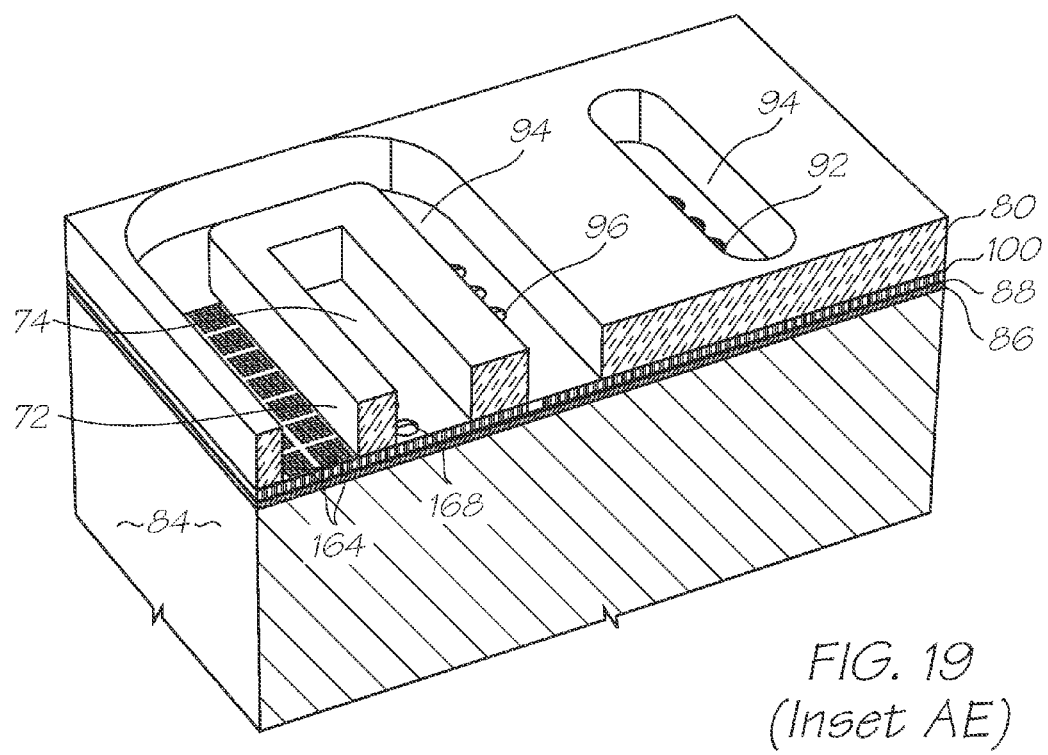
FIG. 19 is a partial perspective illustrating the laminar structure of the LOC device within Inset AE.
Figure 20:
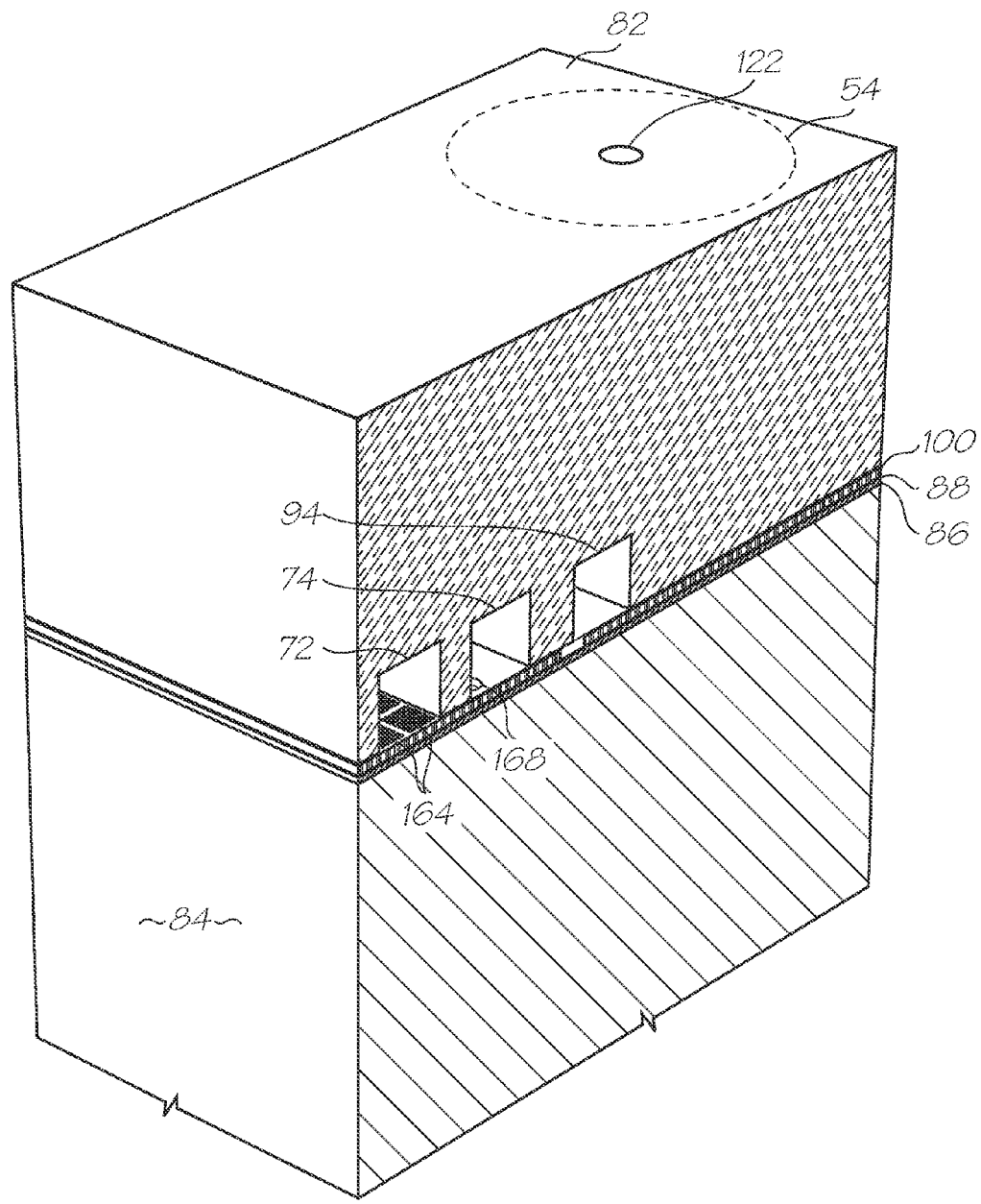
FIG. 20 is a partial perspective illustrating the laminar structure of the LOC device within Inset AE.
Figure 21:
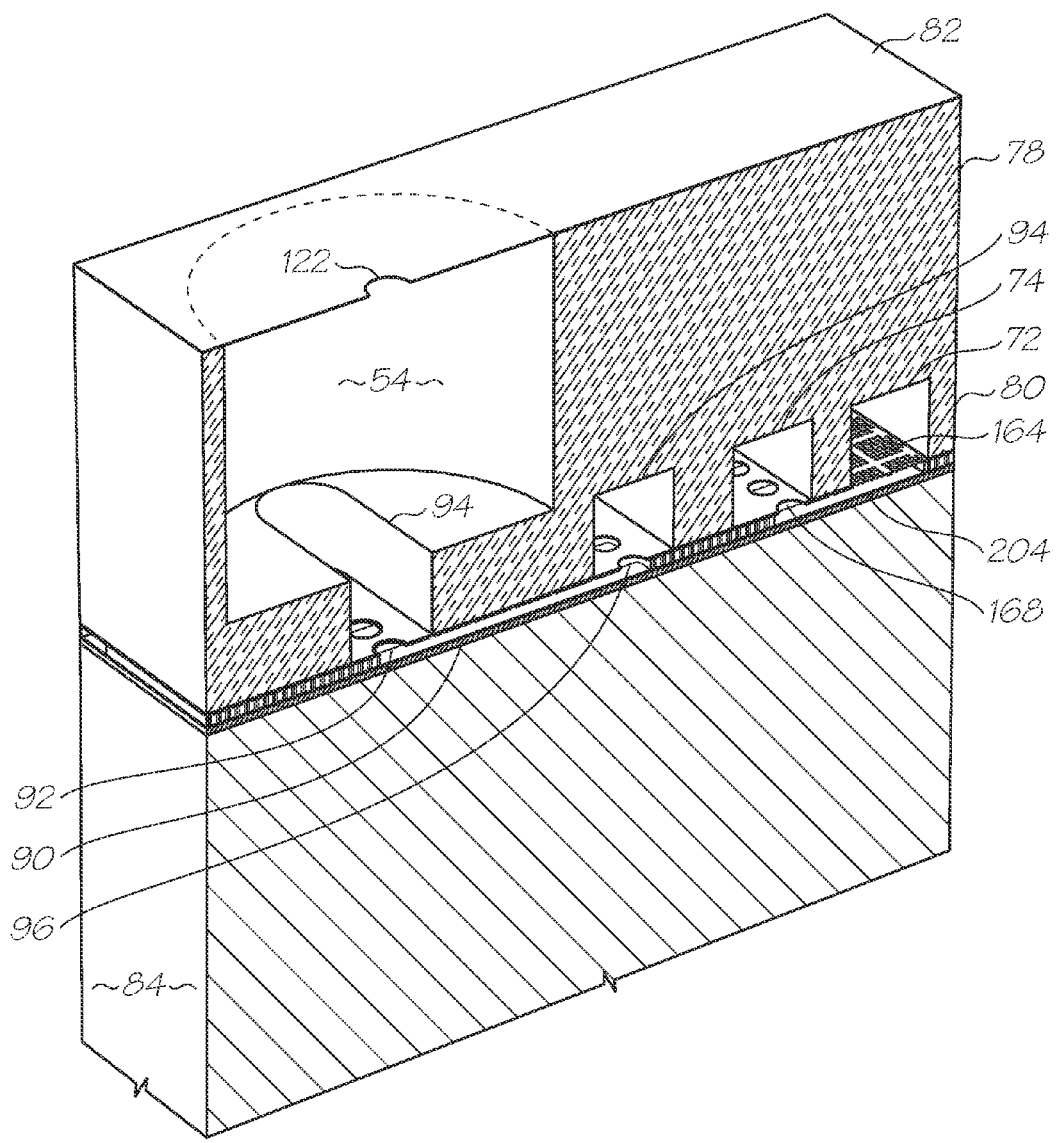
FIG. 21 is a partial perspective illustrating the laminar structure of the LOC device within Inset AE.

FIGS. 15 to 21 show Inset AE which is a portion of Inset AA shown in FIG. 13. As shown in FIGS. 15, 16 and 17, the surface tension valve 118 has three separate MST channels 90 extending between respective downtakes 92 and uptakes 96. The number of MST channels 90 in a surface tension valve can be varied to change the flow rate of the reagent into the sample mixture. As the sample mixture and the reagents mix together by diffusion, the flow rate out of the reservoir determines the concentration of the reagent in the sample flow. Hence, the surface tension valve for each of the reservoirs is configured to match the desired reagent concentration.

The blood passes into a pathogen dialysis section 70 (see FIGS. 4 and 15) where target cells are concentrated from the sample using an array of apertures 164 sized according to a predetermined threshold. Cells smaller than the threshold pass through the apertures while larger cells do not pass through the apertures. Unwanted cells, which may be either the larger cells withheld by the array of apertures 164 or the smaller cells that pass through the apertures, are redirected to a waste unit 76 while the target cells continue as part of the assay.

In the pathogen dialysis section 70 described here, the pathogens from the whole blood sample are concentrated for microbial DNA analysis. The array of apertures is formed by a multitude of 3 micron diameter holes 164 fluidically connecting the input flow in the cap channel 94 to a target channel 74. The 3 micron diameter apertures 164 and the dialysis uptake holes 168 for the target channel 74 are connected by a series of dialysis MST channels 204 (best shown in FIGS. 15 and 21). Pathogens are small enough to pass through the 3 micron diameter apertures 164 and fill the target channel 74 via the dialysis MST channels 204. Cells larger than 3 microns, such as erythrocytes and leukocytes, stay in the waste channel 72 in the cap 46 which leads to a waste reservoir 76 (see FIG. 7).

Other aperture shapes, sizes and aspect ratios can be used to isolate specific pathogens or other target cells such as leukocytes for human DNA analysis. Greater detail on the dialysis section and dialysis variants is provided later.

Referring again to FIGS. 6 and 7, the flow is drawn through the target channel 74 to the surface tension valve 128 of the lysis reagent reservoir 56. The surface tension valve 128 has seven MST channels 90 extending between the lysis reagent reservoir 56 and the target channel 74. When the menisci are unpinned by the sample flow, the flow rate from all seven of the MST channels 90 will be greater than the flow rate from the anticoagulant reservoir 54 where the surface tension valve 118 has three MST channels 90 (assuming the physical characteristics of the fluids are roughly equivalent). Hence the proportion of lysis reagent in the sample mixture is greater than that of the anticoagulant.

The lysis reagent and target cells mix by diffusion in the target channel 74 within the chemical lysis section 130. A boiling-initiated valve 126 stops the flow until sufficient time has passed for diffusion and lysis to take place, releasing the genetic material from the target cells (see FIGS. 6 and 7). The structure and operation of the boiling-initiated valves are described in greater detail below with reference to FIGS. 31 and 32. Other active valve types (as opposed to passive valves such as the surface tension valve 118) have also been developed by the Applicant which may be used here instead of the boiling-initiated valve. These alternative valve designs are also described later.

When the boiling-initiated valve 126 opens, the lysed cells flow into a mixing section 131 for pre-amplification restriction digestion and linker ligation.

Referring to FIG. 13, restriction enzymes, linkers and ligase are released from the reservoir 58 when the flow unpins the menisci at the surface tension valve 132 at the start of the mixing section 131. The mixture flows the length of the mixing section 131 for diffusion mixing. At the end of the mixing section 131 is downtake 134 leading into the incubator inlet channel 133 of the incubation section 114 (see FIG. 13). The incubator inlet channel 133 feeds the mixture into a serpentine configuration of heated microchannels 210 which provides an incubation chamber for holding the sample during restriction digestion and ligation of the linkers (see FIGS. 13 and 14).

Figure 23:
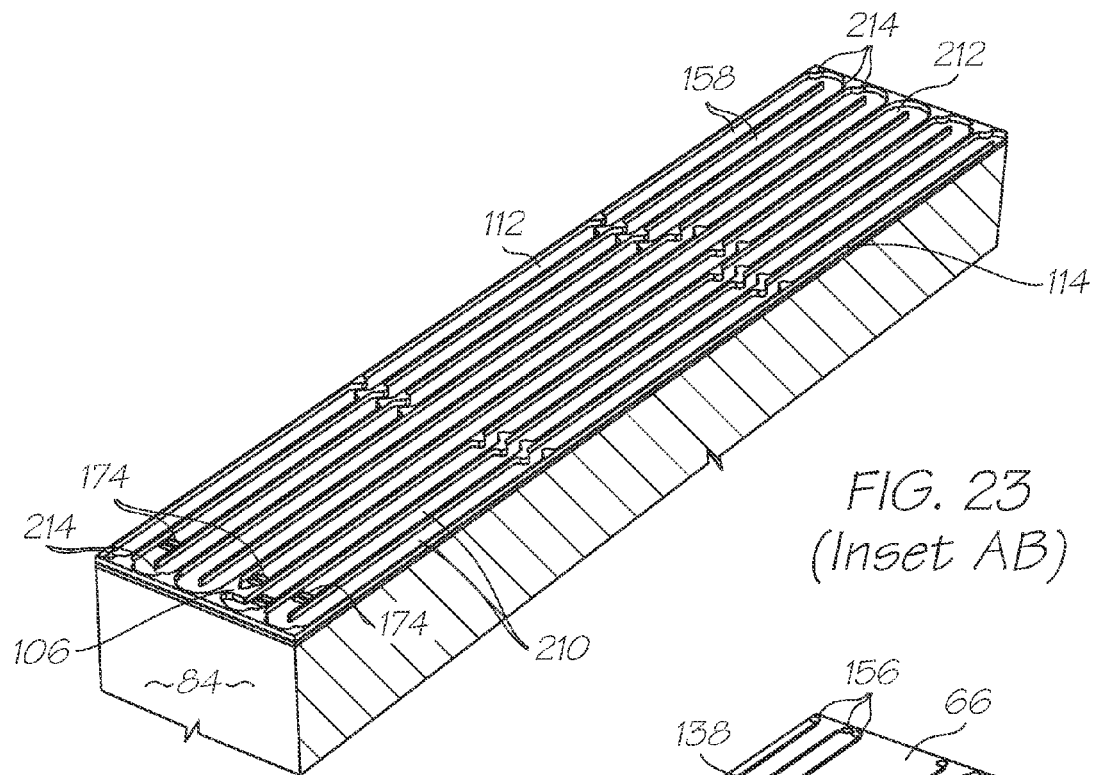
FIG. 23 is a partial perspective illustrating the laminar structure of the LOC device within Inset AB.
Figure 24:
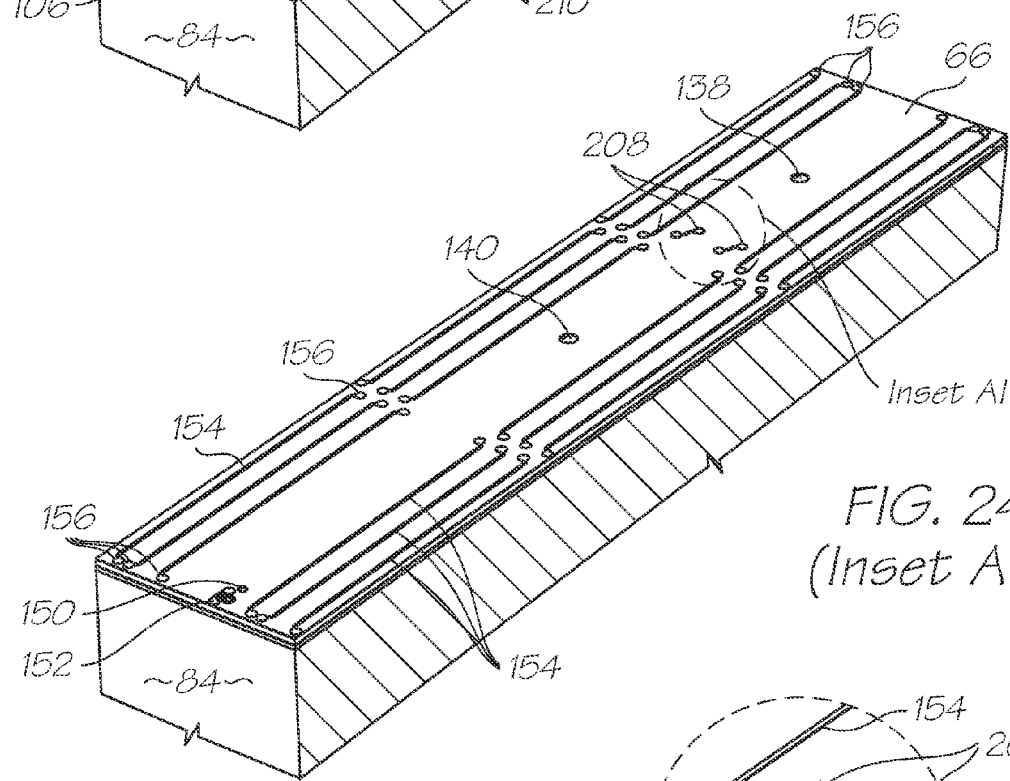
FIG. 24 is a partial perspective illustrating the laminar structure of the LOC device within Inset AB.

FIGS. 23, 24, 25, 26, 27, 28 and 29 show the layers of the LOC device 301 within Inset AB of FIG. 6. Each figure shows the sequential addition of layers forming the structures of the CMOS+MST layer 48 and the cap 46. Inset AB shows the end of the incubation section 114 and the start of the amplification section 112. As best shown in FIGS. 14 and 23, the flow fills the microchannels 210 of the incubation section 114 until reaching the boiling-initiated valve 106 where the flow stops while diffusion takes place. As discussed above, the microchannel 210 upstream of the boiling-initiated valve 106 becomes an incubation chamber containing the sample, restriction enzymes, ligase and linkers. The heaters 154 are then activated and held at constant temperature for a specified time for restriction digestion and linker ligation to occur.

The skilled worker will appreciate that this incubation step 291 (see FIG. 4) is optional and only required for some nucleic acid amplification assay types. Furthermore, in some instances, it may be necessary to have a heating step at the end of the incubation period to spike the temperature above the incubation temperature. The temperature spike inactivates the restriction enzymes and ligase prior to entering the amplification section 112. Inactivation of the restriction enzymes and ligase has particular relevance when isothermal nucleic acid amplification is being employed.

Figure 31:
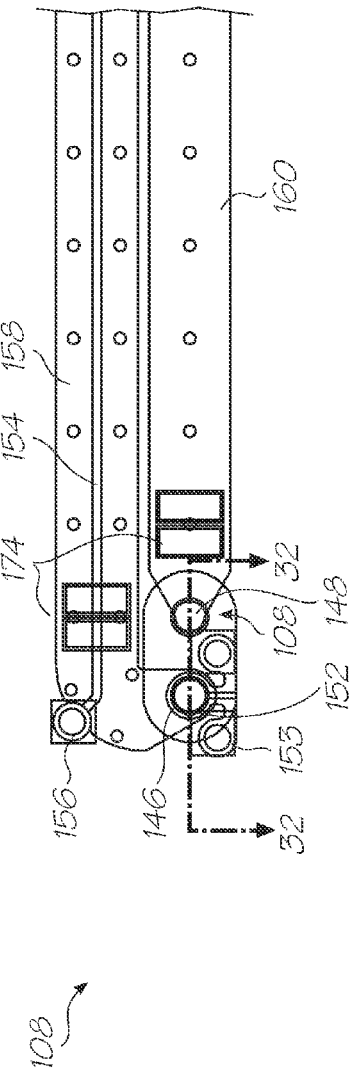
FIG. 31 show the features of a boiling-initiated valve in isolation.
Figure 32:
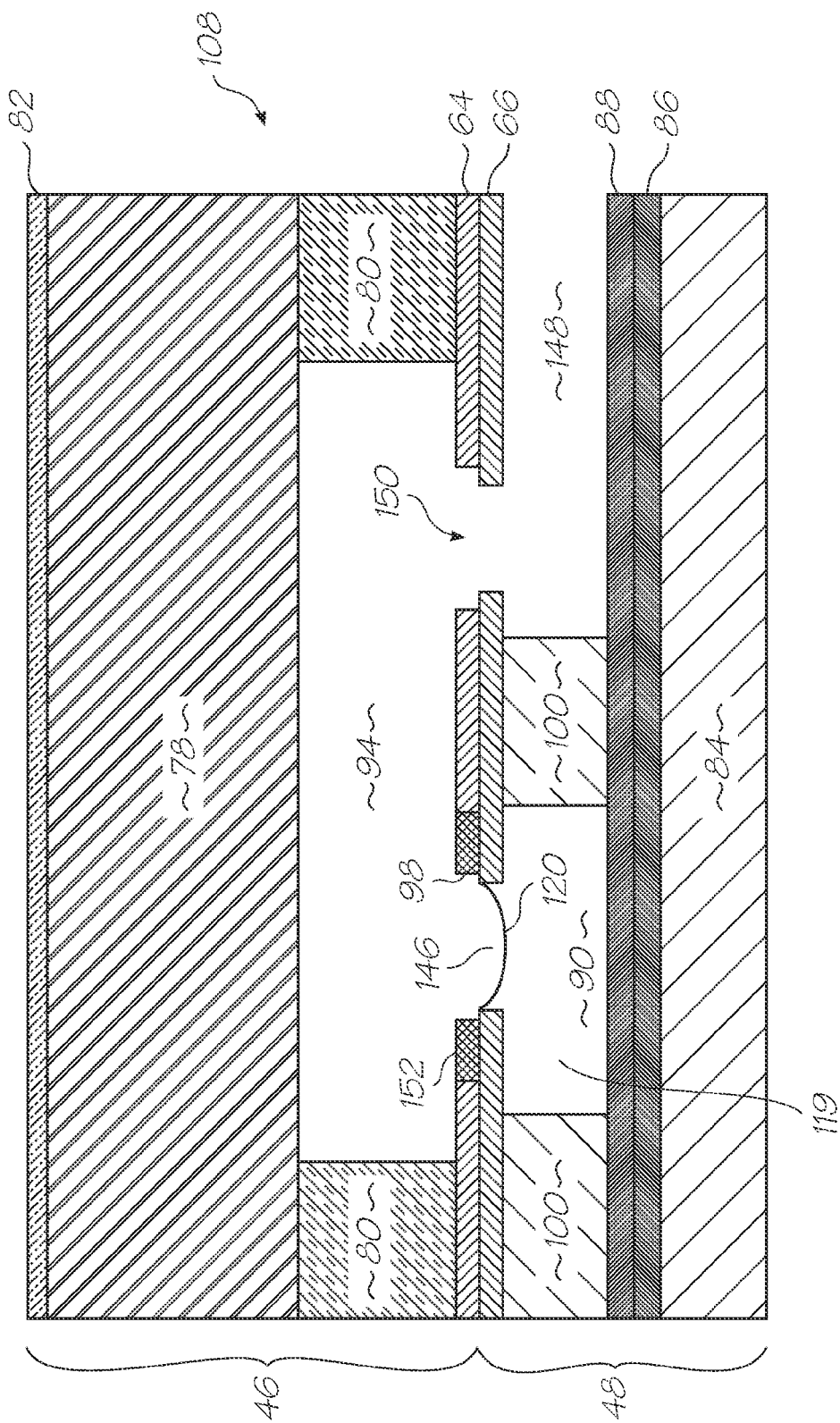
FIG. 32 is a schematic section view of the boiling-initiated valve taken through line 33-33 shown in FIG. 31.
Figure 33:
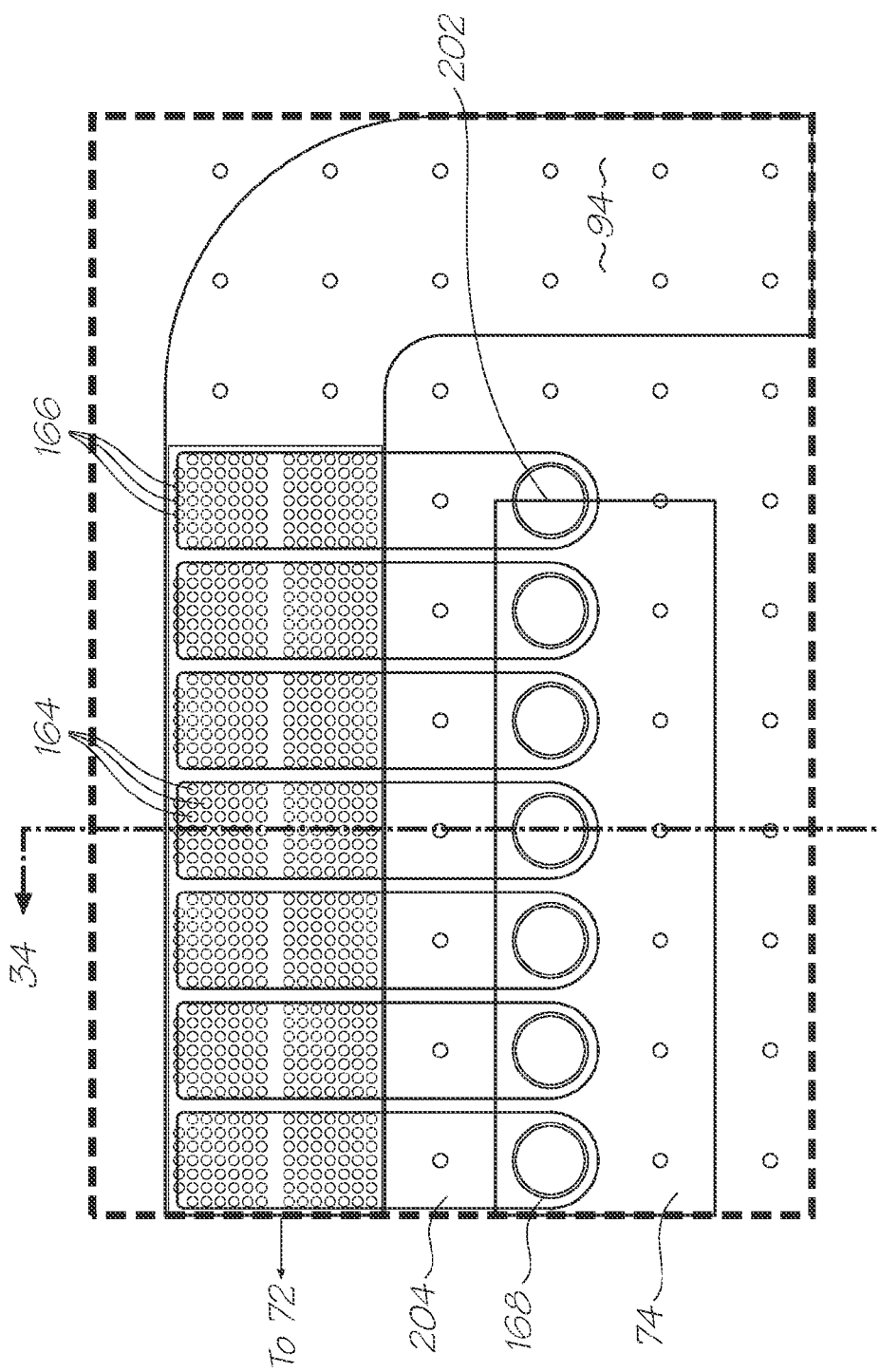
FIG. 33 is an enlarged view of Inset AF shown in FIG. 15.
Figure 34:
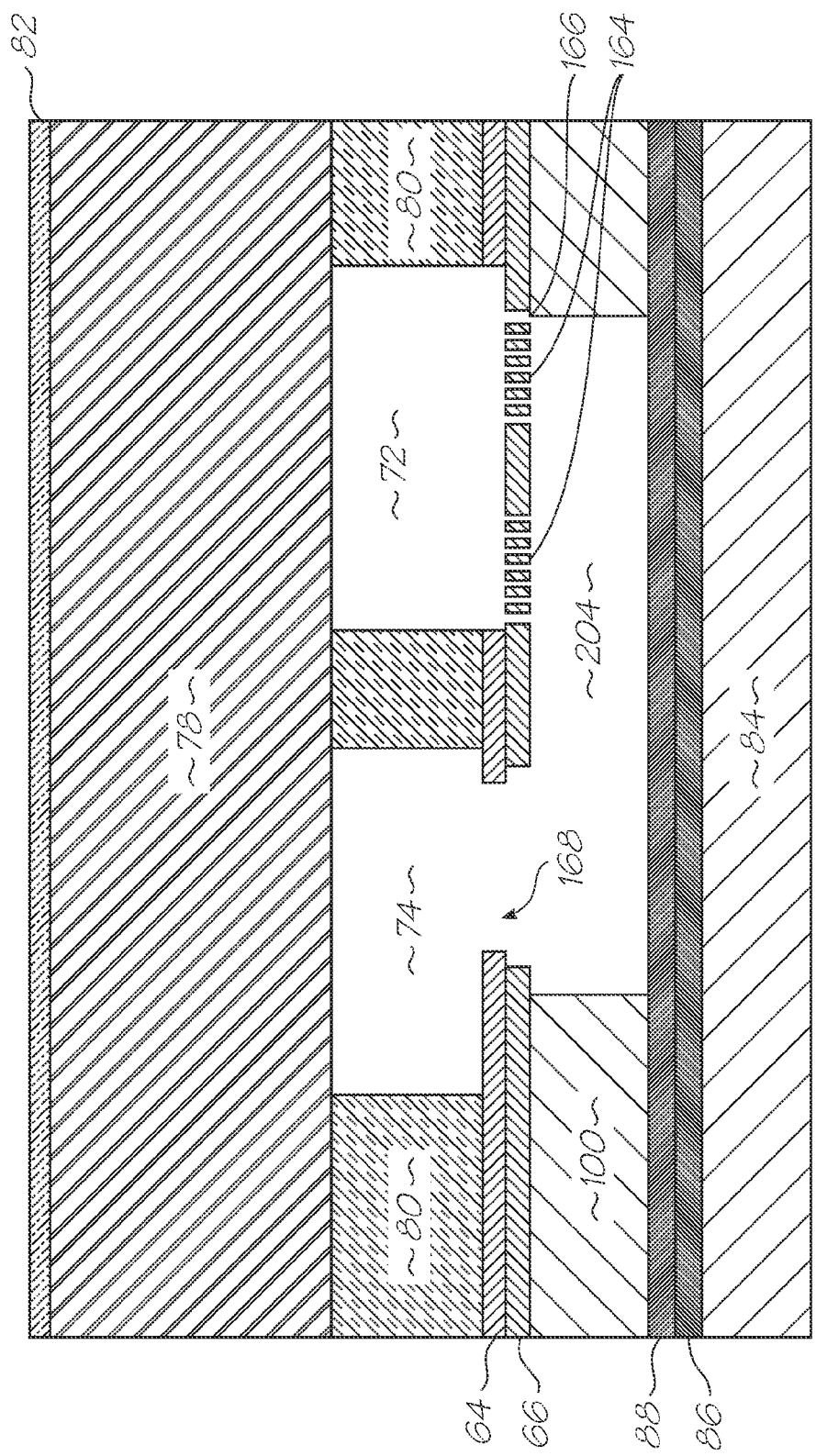
FIG. 34 is a schematic section view of the upstream end of the dialysis section taken through line 35-35 shown in FIG. 33.

Following incubation, the boiling-initiated valve 106 is activated (opened) and the flow resumes into the amplification section 112. Referring to FIGS. 31 and 32, the mixture fills the serpentine configuration of heated microchannels 158, which form one or more amplification chambers, until it reaches the boiling-initiated valve 108. As best shown in the schematic section view of FIG. 30, amplification mix (dNTPs, primers, buffer) is released from reservoir 60 and polymerase is subsequently released from reservoir 62 into the intermediate MST channel 212 connecting the incubation and amplification sections (114 and 112 respectively).

FIGS. 35 to 51 show the layers of the LOC device 301 within Inset AC of FIG. 6. Each figure shows the sequential addition of layers forming the structures of the CMOS+MST device 48 and the cap 46. Inset AC is at the end of the amplification section 112 and the start of the hybridization and detection section 52. The incubated sample, amplification mix and polymerase flow through the microchannels 158 to the boiling-initiated valve 108. After sufficient time for diffusion mixing, the heaters 154 in the microchannels 158 are activated for thermal cycling or isothermal amplification. The amplification mix goes through a predetermined number of thermal cycles or a preset amplification time to amplify sufficient target DNA. After the nucleic acid amplification process, the boiling-initiated valve 108 opens and flow resumes into the hybridization and detection section 52. The operation of boiling-initiated valves is described in more detail later.

Figure 52:
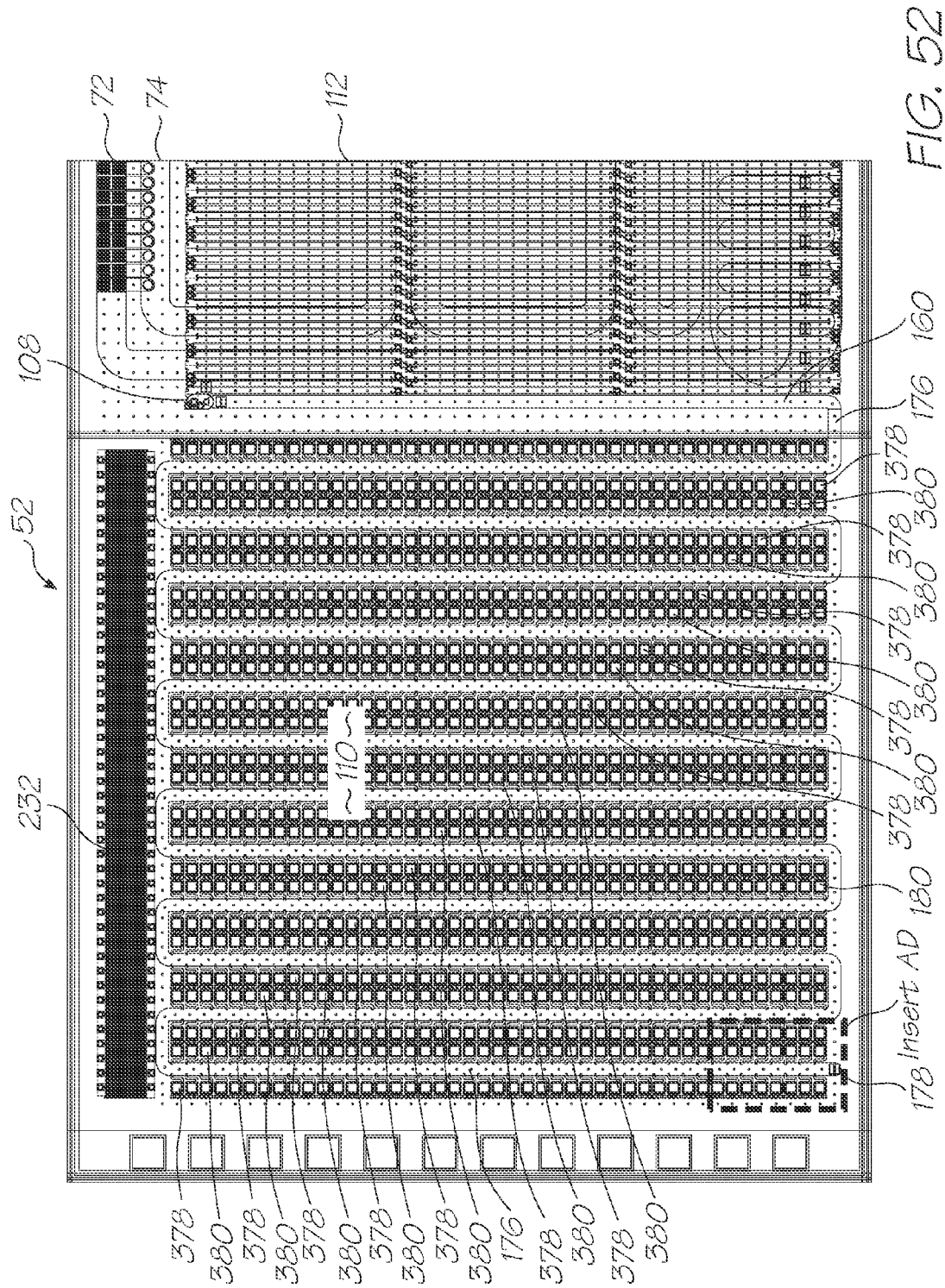
FIG. 52 is an enlarged plan view of the hybridization section.

As shown in FIG. 52, the hybridization and detection section 52 has an array of hybridization chambers 110. FIGS. 52, 53, 54 and 56 show the hybridization chamber array 110 and individual hybridization chambers 180 in detail. At the entrance to the hybridization chamber 180 is a diffusion barrier 175 which prevents diffusion of the target nucleic acid, probe strands and hybridized probes between the hybridization chambers 180 during hybridization so as to prevent erroneous hybridization detection results. The diffusion barriers 175 present a flow-path-length that is long enough to prevent the target sequences and probes diffusing out of one chamber and contaminating another chamber within the time taken for the probes and nucleic acids to hybridize and the signal to be detected, thus avoiding an erroneous result.

Another mechanism to prevent erroneous readings is to have identical probes in a number of the hybridization chambers. The CMOS circuitry 86 derives a single result from the photodiodes 184 corresponding to the hybridization chambers 180 that contain identical probes. Anomalous results can be disregarded or weighted differently in the derivation of the single result.

Figure 69:
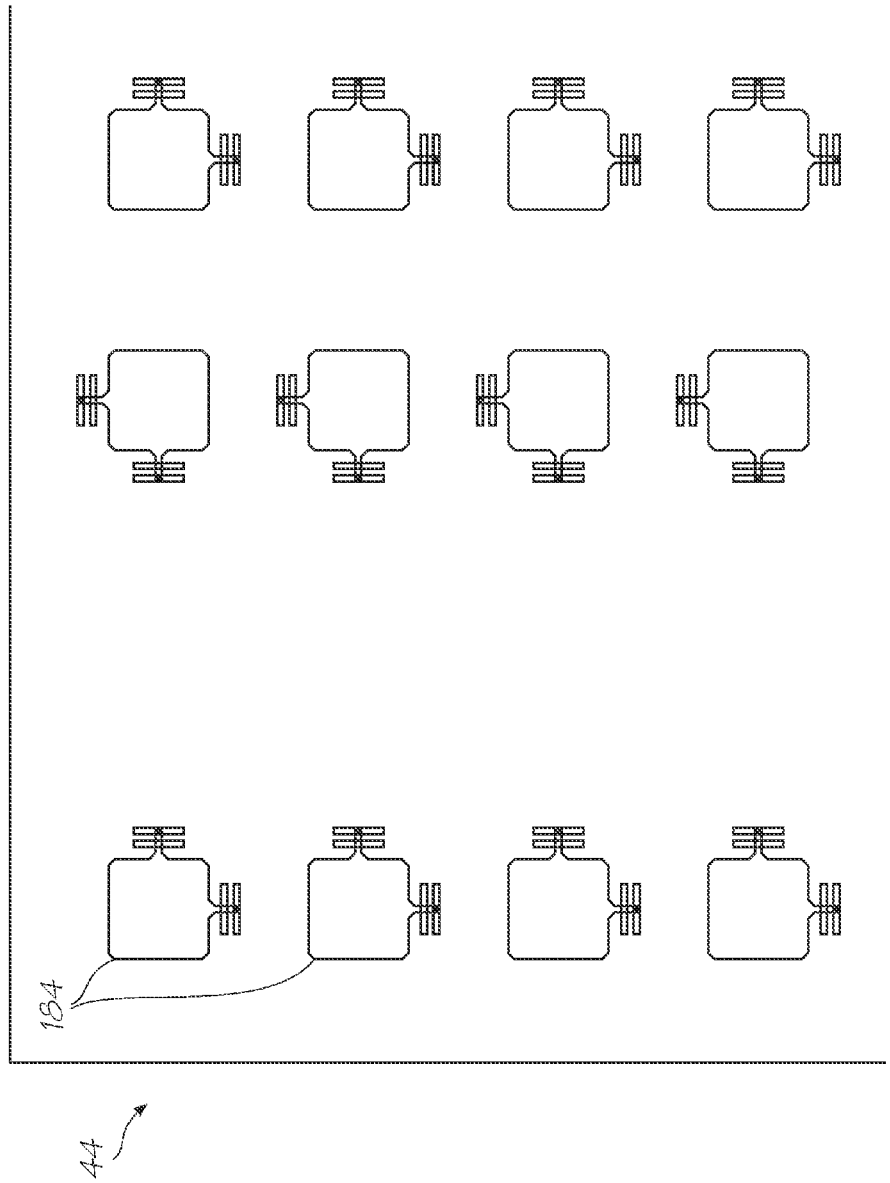
FIG. 69 is a schematic showing part of the photodiode array of the photo sensor.

The thermal energy required for hybridization is provided by CMOS-controlled heaters 182 (described in more detail below). After the heater is activated, hybridization occurs between complementary target-probe sequences. The LED driver 29 in the CMOS circuitry 86 signals the LED 26 located in the test module 10 to illuminate. These probes only fluoresce when hybridization has occurred thereby avoiding washing and drying steps that are typically required to remove unbound strands. Hybridization forces the stem-and-loop structure of the FRET probes 186 to open, which allows the fluorophore to emit fluorescent energy in response to the LED excitation light, as discussed in greater detail later. Fluorescence is detected by a photodiode 184 in the CMOS circuitry 86 underlying each hybridization chamber 180 (see hybridization chamber description below). The photodiodes 184 for all hybridization chambers and associated electronics collectively form the photosensor 44 (see FIG. 69). In other embodiments, the photosensor may be an array of charge coupled devices (CCD array). The detected signal from the photodiodes 184 is amplified and converted to a digital output which is analyzed by the test module reader 12. Further details of the detection method are described later.

Additional Details for the LOC Device

Modularity of the Design

The LOC device 301 has many functional sections, including the reagent reservoirs 54, 56, 58, 60 and 62, the dialysis section 70, lysis section 130, incubation section 114, and amplification section 112, valve types, the humidifier and humidity sensor. In other embodiments of the LOC device, these functional sections can be omitted, additional functional sections can be added or the functional sections can be used for alternative purposes to those described above.

For example, the incubation section 114 can be used as the first amplification section 112 of a tandem amplification assay system, with the chemical lysis reagent reservoir 56 being used to add the first amplification mix of primers, dNTPs and buffer and reagent reservoir 58 being used for adding the reverse transcriptase and/or polymerase. A chemical lysis reagent can also be added to the reservoir 56 along with the amplification mix if chemical lysis of the sample is desired or, alternatively, thermal lysis can occur in the incubation section by heating the sample for a predetermined time. In some embodiments, an additional reservoir can be incorporated immediately upstream of reservoir 58 for the mix of primers, dNTPs and buffer if there is a requirement for chemical lysis and a separation of this mix from the chemical lysis reagent is desired.

In some circumstances it may be desirable to omit a step, such as the incubation step 291. In this case, a LOC device can be specifically fabricated to omit the reagent reservoir 58 and incubation section 114, or the reservoir can simply not be loaded with reagents or the active valves, if present, not activated to dispense the reagents into the sample flow, and the incubation section then simply becomes a channel to transport the sample from the lysis section 130 to the amplification section 112. The heaters are independently operable and therefore, where reactions are dependent on heat, such as thermal lysis, programming the heaters not to activate during this step ensures thermal lysis does not occur in LOC devices that do not require it. The dialysis section 70 can be located at the beginning of the fluidic system within the microfluidic device as shown in FIG. 4 or can be located anywhere else within the microfluidic device. For example, dialysis after the amplification phase 292 to remove cellular debris prior to the hybridization and detection step 294 may be beneficial in some circumstances. Alternatively, two or more dialysis sections can be incorporated at any location throughout the LOC device. Similarly, it is possible to incorporate additional amplification sections 112 to enable multiple targets to be amplified in parallel or in series prior to being detected in the hybridization chamber arrays 110 with specific nucleic acid probes. For analysis of samples like whole blood, in which dialysis is not required, the dialysis section 70 is simply omitted from the sample input and preparation section 288 of the LOC design. In some cases, it is not necessary to omit the dialysis section 70 from the LOC device even if the analysis does not require dialysis. If there is no geometric hindrance to the assay by the existence of a dialysis section, a LOC with the dialysis section 70 in the sample input and preparation section can still be used without a loss of the required functionality.

Furthermore, the detection section 294 may encompass proteomic chamber arrays which are identical to the hybridization chamber arrays but are loaded with probes designed to conjugate or hybridize with sample target proteins present in non-amplified sample instead of nucleic acid probes designed to hybridize to target nucleic acid sequences.

It will be appreciated that the LOC devices fabricated for use in this diagnostic system are different combinations of functional sections selected in accordance with the particular LOC application. The vast majority of functional sections are common to many of the LOC devices and the design of additional LOC devices for new application is a matter of compiling an appropriate combination of functional sections from the extensive selection of functional sections used in the existing LOC devices.

Only a small number of the LOC devices are shown in this description and some more are shown schematically to illustrate the design flexibility of the LOC devices fabricated for this system. The person skilled in the art will readily recognise that the LOC devices shown in this description are not an exhaustive list and many additional LOC designs are a matter of compiling the appropriate combination of functional sections.

Sample Types

LOC variants can accept and analyze the nucleic acid or protein content of a variety of sample types in liquid form including, but not limited to, blood and blood products, saliva, cerebrospinal fluid, urine, semen, amniotic fluid, umbilical cord blood, breast milk, sweat, pleural effusion, tear, pericardial fluid, peritoneal fluid, environmental water samples and drink samples. Amplicon obtained from macroscopic nucleic acid amplification can also be analysed using the LOC device; in this case, all the reagent reservoirs will be empty or configured not to release their contents, and the dialysis, lysis, incubation and amplification sections will be used solely to transport the sample from the sample inlet 68 to the hybridization chambers 180 for nucleic acid detection, as described above.

For some sample types, a pre-processing step is required, for example semen may need to be liquefied and mucus may need to be pre-treated with an enzyme to reduce the viscosity prior to input into the LOC device.

Sample Input

Referring to FIGS. 1 and 12, the sample is added to the macroreceptacle 24 of the test module 10. The macroreceptacle 24 is a truncated cone which feeds into the inlet 68 of the LOC device 301 by capillary action. Here it flows into the 64 μm wide×60 μm deep cap channel 94 where it is drawn towards the anticoagulant reservoir 54, also by capillary action.

Reagent Reservoirs

The small volumes of reagents required by the assay systems using microfluidic devices, such as LOC device 301, permit the reagent reservoirs to contain all reagents necessary for the biochemical processing with each of the reagent reservoirs having a small volume. This volume is easily less than 1,000,000,000 cubic microns, in the vast majority of cases less than 300,000,000 cubic microns, typically less than 70,000,000 cubic microns and in the case of the LOC device 301 shown in the drawings, less than 20,000,000 cubic microns.

Dialysis Section

Referring to FIGS. 15 to 21, 33 and 34, the pathogen dialysis section 70 is designed to concentrate pathogenic target cells from the sample. As previously described, a plurality of apertures in the form of 3 micron diameter holes 164 in the roof layer 66 filter the target cells from the bulk of the sample. As the sample flows past the 3 micron diameter apertures 164, microbial pathogens pass through the holes into a series of dialysis MST channels 204 and flow back up into the target channel 74 via 16 μm dialysis uptake holes 168 (see FIGS. 33 and 34). The remainder of the sample (erythrocytes and so on) stay in the cap channel 94. Downstream of the pathogen dialysis section 70, the cap channel 94 becomes the waste channel 72 leading to the waste reservoir 76. For biological samples of the type that generate a substantial amount of waste, a foam insert or other porous element 49 within the outer casing 13 of the test module 10 is configured to be in fluid communication with the waste reservoir 76 (see FIG. 1).

The pathogen dialysis section 70 functions entirely on capillary action of the fluid sample. The 3 micron diameter apertures 164 at the upstream end of the pathogen dialysis section 70 have capillary initiation features (CIFs) 166 (see FIG. 33) so that the fluid is drawn down into the dialysis MST channel 204 beneath. The first uptake hole 198 for the target channel 74 also has a CIF 202 (see FIG. 15) to avoid the flow simply pinning a meniscus across the dialysis uptake holes 168.

Figure 81:
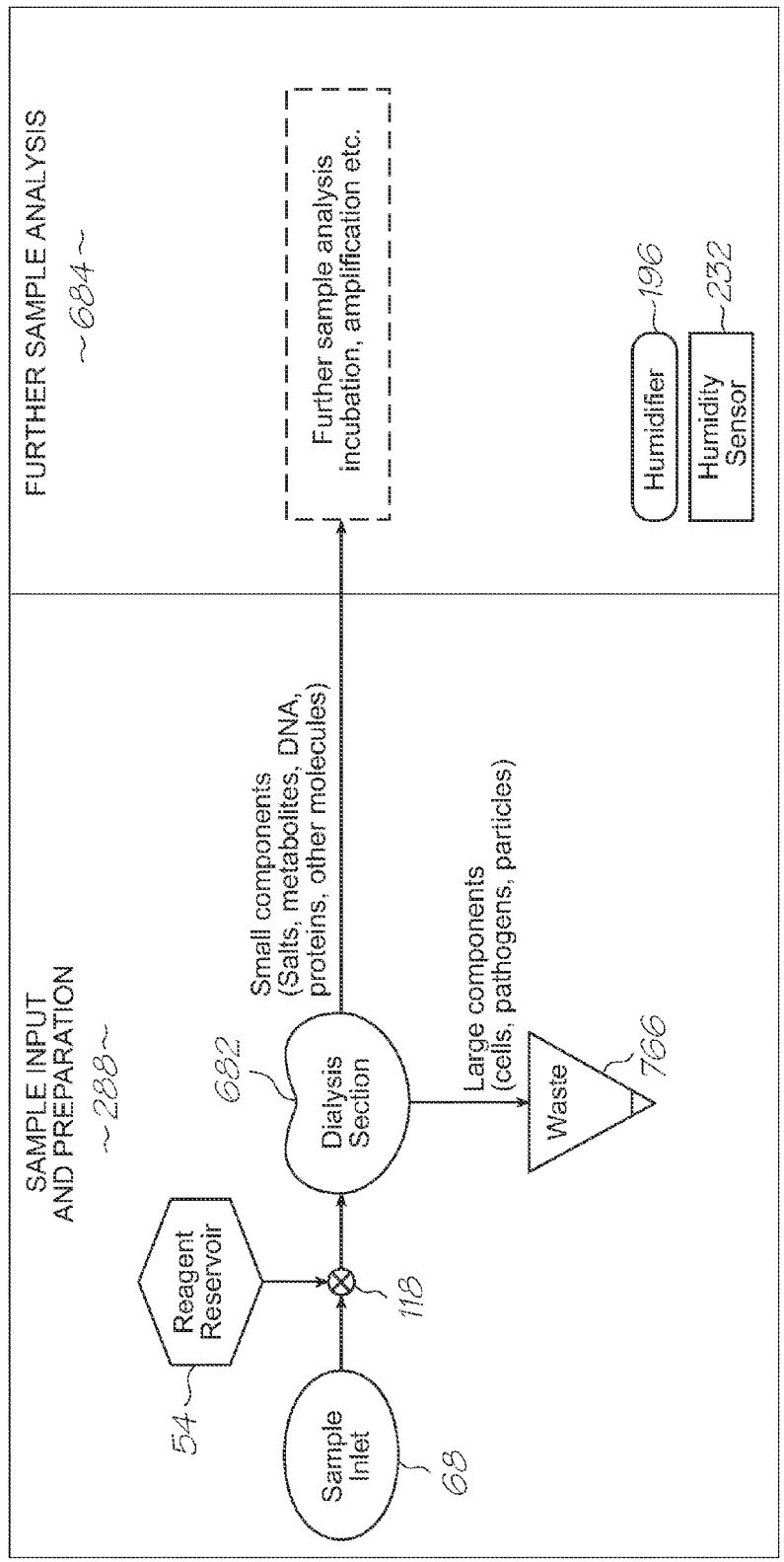
FIG. 81 is a schematic illustration of the architecture of LOC variant XLI.

The small constituents dialysis section 682 schematically shown in FIG. 81 can have a similar structure to the pathogen dialysis section 70. The small constituents dialysis section separates any small target cells or molecules from a sample by sizing (and, if necessary, shaping) apertures suitable for allowing the small target cells or molecules to pass into the target channel and continue for further analysis. Larger sized cells or molecules are removed to a waste reservoir 766. Thus, the LOC device 30 (see FIGS. 1 and 103) is not limited to separating pathogens that are less than 3 μm in size, but can be used to separate cells or molecules of any size desired.

Lysis Section

Referring back to FIGS. 7, 11 and 13, the genetic material in the sample is released from the cells by a chemical lysis process. As described above, a lysis reagent from the lysis reservoir 56 mixes with the sample flow in the target channel 74 downstream of the surface tension valve 128 for the lysis reservoir 56. However, some diagnostic assays are better suited to a thermal lysis process, or even a combination of chemical and thermal lysis of the target cells. The LOC device 301 accommodates this with the heated microchannels 210 of the incubation section 114. The sample flow fills the incubation section 114 and stops at the boiling-initiated valve 106. The incubation microchannels 210 heat the sample to a temperature at which the cellular membranes are disrupted.

In some thermal lysis applications, an enzymatic reaction in the chemical lysis section 130 is not necessary and the thermal lysis completely replaces the enzymatic reaction in the chemical lysis section 130.

Boiling-Initiated Valve

As discussed above, the LOC device 301 has three boiling-initiated valves 126, 106 and 108. The location of these valves is shown in FIG. 6. FIG. 31 is an enlarged plan view of the boiling-initiated valve 108 in isolation at the end of the heated microchannels 158 of the amplification section 112.

The sample flow 119 is drawn along the heated microchannels 158 by capillary action until it reaches the boiling-initiated valve 108. The leading meniscus 120 of the sample flow pins at a meniscus anchor 98 at the valve inlet 146. The geometry of the meniscus anchor 98 stops the advancing meniscus to arrest the capillary flow. As shown in FIGS. 31 and 32, the meniscus anchor 98 is an aperture provided by an uptake opening from the MST channel 90 to the cap channel 94. Surface tension in the meniscus 120 keeps the valve closed. An annular heater 152 is at the periphery of the valve inlet 146. The annular heater 152 is CMOS-controlled via the boiling-initiated valve heater contacts 153.

To open the valve, the CMOS circuitry 86 sends an electrical pulse to the valve heater contacts 153. The annular heater 152 resistively heats until the liquid sample 119 boils. The boiling unpins the meniscus 120 from the valve inlet 146 and initiates wetting of the cap channel 94. Once wetting the cap channel 94 begins, capillary flow resumes. The fluid sample 119 fills the cap channel 94 and flows through the valve downtake 150 to the valve outlet 148 where capillary driven flow continues along the amplification section exit channel 160 into the hybridization and detection section 52. Liquid sensors 174 are placed before and after the valve for diagnostics.

It will be appreciated that once the boiling-initiated valves are opened, they cannot be re-closed. However, as the LOC device 301 and the test module 10 are single-use devices, re-closing the valves is unnecessary.

Incubation Section and Nucleic Acid Amplification Section

FIGS. 6, 7, 13, 14, 23, 24, 25, 35 to 45, 50 and 51 show the incubation section 114 and the amplification section 112. The incubation section 114 has a single, heated incubation microchannel 210 etched in a serpentine pattern in the MST channel layer 100 from the downtake opening 134 to the boiling-initiated valve 106 (see FIGS. 13 and 14). Control over the temperature of the incubation section 114 enables enzymatic reactions to take place with greater efficiency. Similarly, the amplification section 112 has a heated amplification microchannel 158 in a serpentine configuration leading from the boiling-initiated valve 106 to the boiling-initiated valve 108 (see FIGS. 6 and 14). These valves arrest the flow to retain the target cells in the heated incubation or amplification microchannels 210 or 158 while mixing, incubation and nucleic acid amplification takes place. The serpentine pattern of the microchannels also facilitates (to some extent) mixing of the target cells with reagents.

Figure 51:
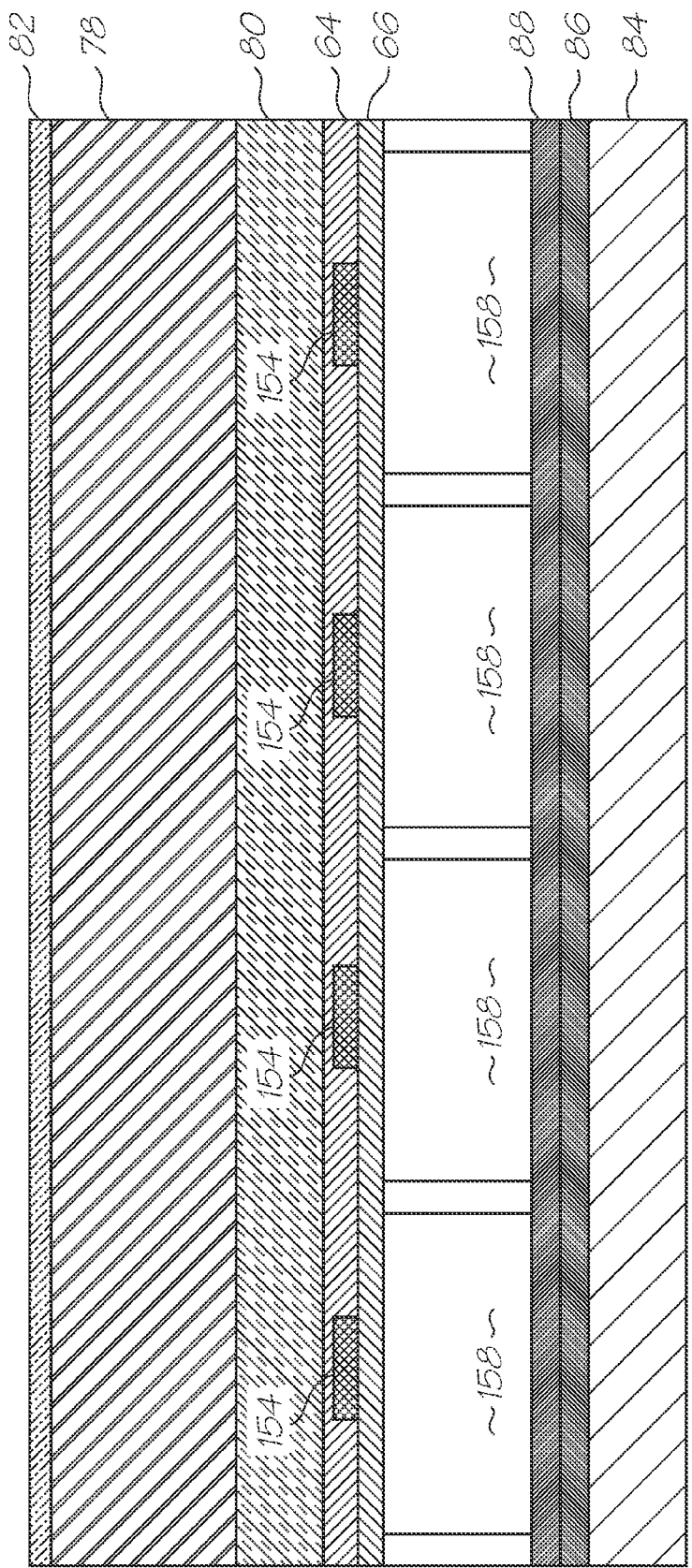
FIG. 51 is a schematic section view of the amplification section.

In the incubation section 114 and the amplification section 112, the sample cells and the reagents are heated by the heaters 154 controlled by the CMOS circuitry 86 using pulse width modulation (PWM). Each meander of the serpentine configuration of the heated incubation microchannel 210 and amplification microchannel 158 has three separately operable heaters 154 extending between their respective heater contacts 156 (see FIG. 14) which provides for the two-dimensional control of input heat flux density. As best shown in FIG. 51, the heaters 154 are supported on the roof layer 66 and embedded in the lower seal 64. The heater material is TiAl but many other conductive metals would be suitable. The elongate heaters 154 are parallel with the longitudinal extent of each channel section that forms the wide meanders of the serpentine shape. In the amplification section 112, each of the wide meanders can operate as separate PCR chambers via individual heater control.

The small volumes of amplicon required by the assay systems using microfluidic devices, such as LOC device 301, permit low amplification mixture volumes for amplification in amplification section 112. This volume is easily less than 400 nanoliters, in the vast majority of cases less than 170 nanoliters, typically less than 70 nanoliters and in the case of the LOC device 301, between 2 nanoliters and 30 nanoliters.

Increased Rates of Heating and Greater Diffusive Mixing

The small cross section of each channel section increases the heating rate of the amplification fluid mix. All the fluid is kept a relatively short distance from the heater 154. Reducing the channel cross section (that is the amplification microchannel 158 cross section) to less than 100,000 square microns achieves appreciably higher heating rates than that provided by more 'macro-scale' equipment. Lithographic fabrication techniques allow the amplification microchannel 158 to have a cross sectional area transverse to the flow-path less than 16,000 square microns which gives substantially higher heating rates. Feature sizes on the order of 1 micron are readily achievable with lithographic techniques. If very little amplicon is needed (as is the case in the LOC device 301), the cross sectional area can be reduced to less than 2,500 square microns. For diagnostic assays with 1,000 to 2,000 probes on the LOC device, and a requirement of 'sample-in, answer out' in less than 1 minute, a cross sectional area transverse to the flow of between 400 square microns and 1 square micron is adequate.

The heater element in the amplification microchannel 158 heats the nucleic acid sequences at a rate more than 80 Kelvin (K) per second, in the vast majority of cases at a rate greater than 100 K per second. Typically, the heater element heats the nucleic acid sequences at a rate more than 1,000 K per second and in many cases, the heater element heats the nucleic acid sequences at a rate more than 10,000 K per second. Commonly, based on the demands of the assay system, the heater element heats the nucleic acid sequences at a rate more than 100,000 K per second, more than 1,000,000 K per second more than 10,000,000 K per second, more than 20,000,000 K per second, more than 40,000,000 K per second, more than 80,000,000 K per second and more than 160,000,000 K per second.

A small cross-sectional area channel is also beneficial for diffusive mixing of any reagents with the sample fluid. Before diffusive mixing is complete, diffusion of one liquid into the other is greatest near the interface between the two. Concentration decreases with distance from the interface. Using microchannels with relatively small cross sections transverse to the flow direction, keeps both fluid flows close to the interface for more rapid diffusive mixing. Reducing the channel cross section to less than 100,000 square microns achieves appreciably higher mixing rates than that provided by more 'macro-scale' equipment. Lithographic fabrication techniques allows microchannels with a cross sectional area transverse to the flow-path less than 16000 square microns which gives significantly higher mixing rates. If small volumes are needed (as is the case in the LOC device 301), the cross sectional area can be reduced to less than 2500 square microns. For diagnostic assays with 1000 to 2000 probes on the LOC device, and a requirement of 'sample-in, answer out' in less than 1 minute, a cross sectional area transverse to the flow of between 400 square microns and 1 square micron is adequate.

Short Thermal Cycle Times

Keeping the sample mixture proximate to the heaters, and using very small fluid volumes allows rapid thermal cycling during the nucleic acid amplification process. Each thermal cycle (i.e. denaturing, annealing and primer extension) is completed in less than 30 seconds for target sequences up to 150 base pairs (bp) long. In the vast majority of diagnostic assays, the individual thermal cycle times are less than 11 seconds, and a large proportion are less than 4 seconds. LOC devices 30 with some of the most common diagnostic assays have thermal cycles time between 0.45 seconds to 1.5 seconds for target sequences up to 150 bp long. Thermal cycling at this rate allows the test module to complete the nucleic acid amplification process in much less than 10 minutes; often less than 220 seconds. For most assays, the amplification section generates sufficient amplicon in less than 80 seconds from the sample fluid entering the sample inlet. For a great many assays, sufficient amplicon is generated in 30 seconds.

Upon completion of a preset number of amplification cycles, the amplicon is fed into the hybridization and detection section 52 via the boiling-initiated valve 108.

Hybridization Chambers

FIGS. 52, 53, 54, 56 and 57 show the hybridization chambers 180 in the hybridization chamber array 110. The hybridization and detection section 52 has a 24×45 array 110 of hybridization chambers 180, each with hybridization-responsive FRET probes 186, heater element 182 and an integrated photodiode 184. The photodiode 184 is incorporated for detection of fluorescence resulting from the hybridization of a target nucleic acid sequence or protein with the FRET probes 186. Each photodiode 184 is independently controlled by the CMOS circuitry 86. Any material between the FRET probes 186 and the photodiode 184 must be transparent to the emitted light. Accordingly, the wall section 97 between the probes 186 and the photodiode 184 is also optically transparent to the emitted light. In the LOC device 301, the wall section 97 is a thin (approximately 0.5 micron) layer of silicon dioxide.

Incorporation of a photodiode 184 directly beneath each hybridization chamber 180 allows the volume of probe-target hybrids to be very small while still generating a detectable fluorescence signal (see FIG. 54). The small amounts permit small volume hybridization chambers. A detectable amount of probe-target hybrid requires a quantity of probe, prior to hybridization, which is easily less than 270 picograms (corresponding to 900,000 cubic microns), in the vast majority of cases less than 60 picograms (corresponding to 200,000 cubic microns), typically less than 12 picograms (corresponding to 40,000 cubic microns) and in the case of the LOC device 301 shown in the accompanying figures, less than 2.7 picograms (corresponding to a chamber volume of 9,000 cubic microns). Of course, reducing the size of the hybridization chambers allows a higher density of chambers and therefore more probes on the LOC device. In LOC device 301, the hybridization section has more than 1,000 chambers in an area of 1,500 microns by 1,500 microns (i.e. less than 2,250 square microns per chamber). Smaller volumes also reduce the reaction times so that hybridization and detection is faster. An additional advantage of the small amount of probe required in each chamber is that only very small quantities of probe solution need to be spotted into each chamber during production of the LOC device. Embodiments of the LOC device according to the invention can be spotted using a probe solution volume of 1 picoliter or less.

After nucleic acid amplification, boiling-initiated valve 108 is activated and the amplicon flows along the flow-path 176 and into each of the hybridization chambers 180 (see FIGS. 52 and 56). An end-point liquid sensor 178 indicates when the hybridization chambers 180 are filled with amplicon and the heaters 182 can be activated.

After sufficient hybridization time, the LED 26 (see FIG. 2) is activated. The opening in each of the hybridization chambers 180 provides an optical window 136 for exposing the FRET probes 186 to the excitation radiation (see FIGS. 52, 54 and 56). The LED 26 is illuminated for a sufficiently long time in order to induce a fluorescence signal from the probes with high intensity. During excitation, the photodiode 184 is shorted. After a pre-programmed delay 300 (see FIG. 2), the photodiode 184 is enabled and fluorescence emission is detected in the absence of the excitation light. The incident light on the active area 185 of the photodiode 184 (see FIG. 54) is converted into a photocurrent which can then be measured using CMOS circuitry 86.

The hybridization chambers 180 are each loaded with probes for detecting a single target nucleic acid sequence. Each hybridization chambers 180 can be loaded with probes to detect over 1,000 different targets if desired. Alternatively, many or all the hybridization chambers can be loaded with the same probes to detect the same target nucleic acid repeatedly. Replicating the probes in this way throughout the hybridization chamber array 110 leads to increased confidence in the results obtained and the results can be combined by the photodiodes adjacent those hybridization chambers to provide a single result if desired. The person skilled in the art will recognise that it is possible to have from one to over 1,000 different probes on the hybridization chamber array 110, depending on the assay specification.

Humidifier and Humidity Sensor

Inset AG of FIG. 6 indicates the position of the humidifier 196. The humidifier prevents evaporation of the reagents and probes during operation of the LOC device 301. As best shown in the enlarged view of FIG. 55, a water reservoir 188 is fluidically connected to three evaporators 190. The water reservoir 188 is filled with molecular biology-grade water and sealed during manufacturing. As best shown in FIGS. 55 and 74, water is drawn into three downtakes 194 and along respective water supply channels 192 by capillary action to a set of three uptakes 193 at the evaporators 190. A meniscus pins at each uptake 193 to retain the water. The evaporators have annular shaped heaters 191 which encircle the uptakes 193. The annular heaters 191 are connected to the CMOS circuitry 86 by the conductive columns 376 to the top metal layer 195 (see FIG. 37). Upon activation, the annular heaters 191 heat the water causing evaporation and humidifying the device surrounds.

The position of the humidity sensor 232 is also shown in FIG. 6. However, as best shown in the enlarged view of Inset AH in FIG. 63, the humidity sensor has a capacitive comb structure. A lithographically etched first electrode 296 and a lithographically etched second electrode 298 face each other such that their teeth are interleaved. The opposed electrodes form a capacitor with a capacitance that can be monitored by the CMOS circuitry 86. As the humidity increases, the permittivity of the air gap between the electrodes increases, so that the capacitance also increases. The humidity sensor 232 is adjacent the hybridization chamber array 110 where humidity measurement is most important to slow evaporation from the solution containing the exposed probes.

Feedback Sensors

Figure 35:
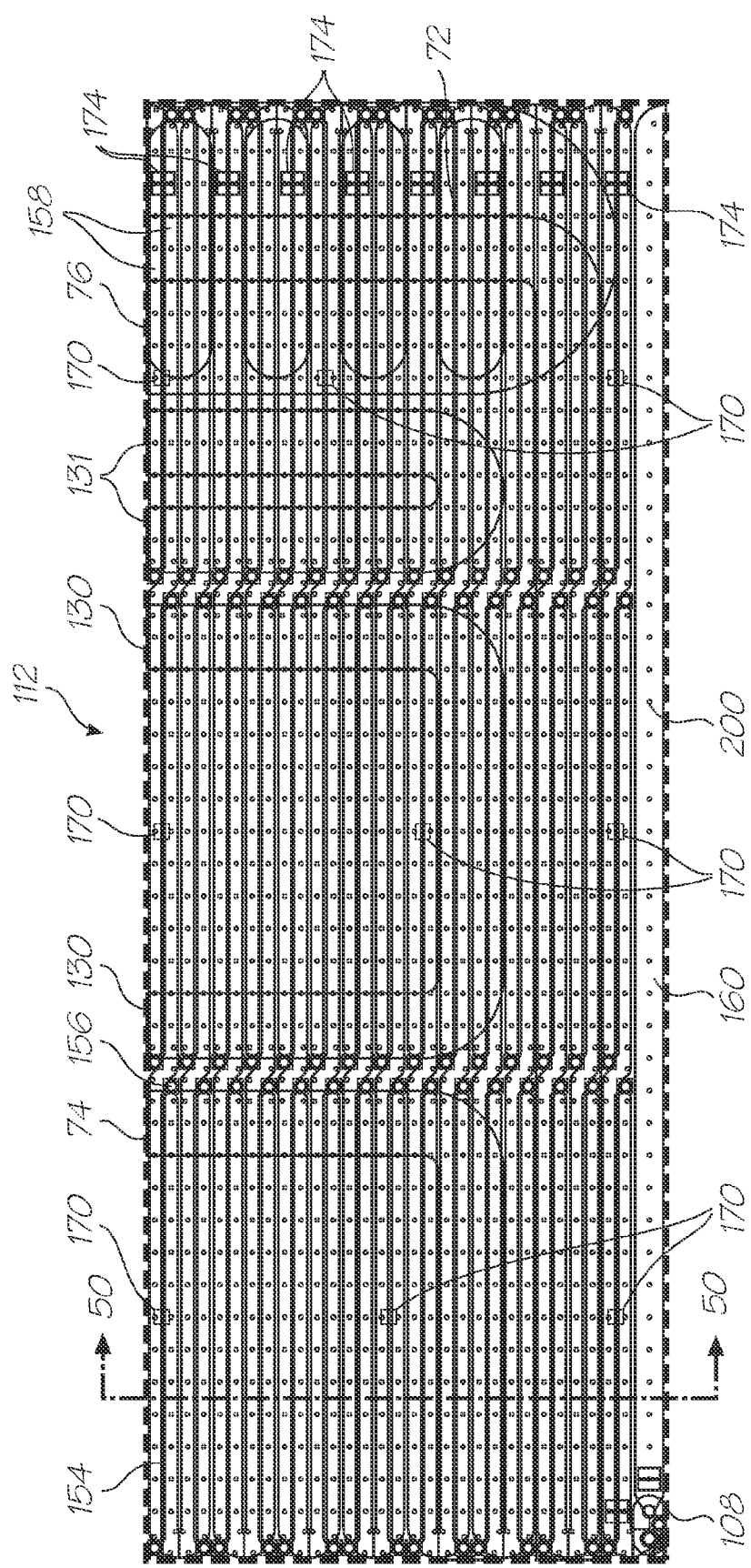
FIG. 35 is an enlarged view of Inset AC shown in FIG. 6.
Figure 36:
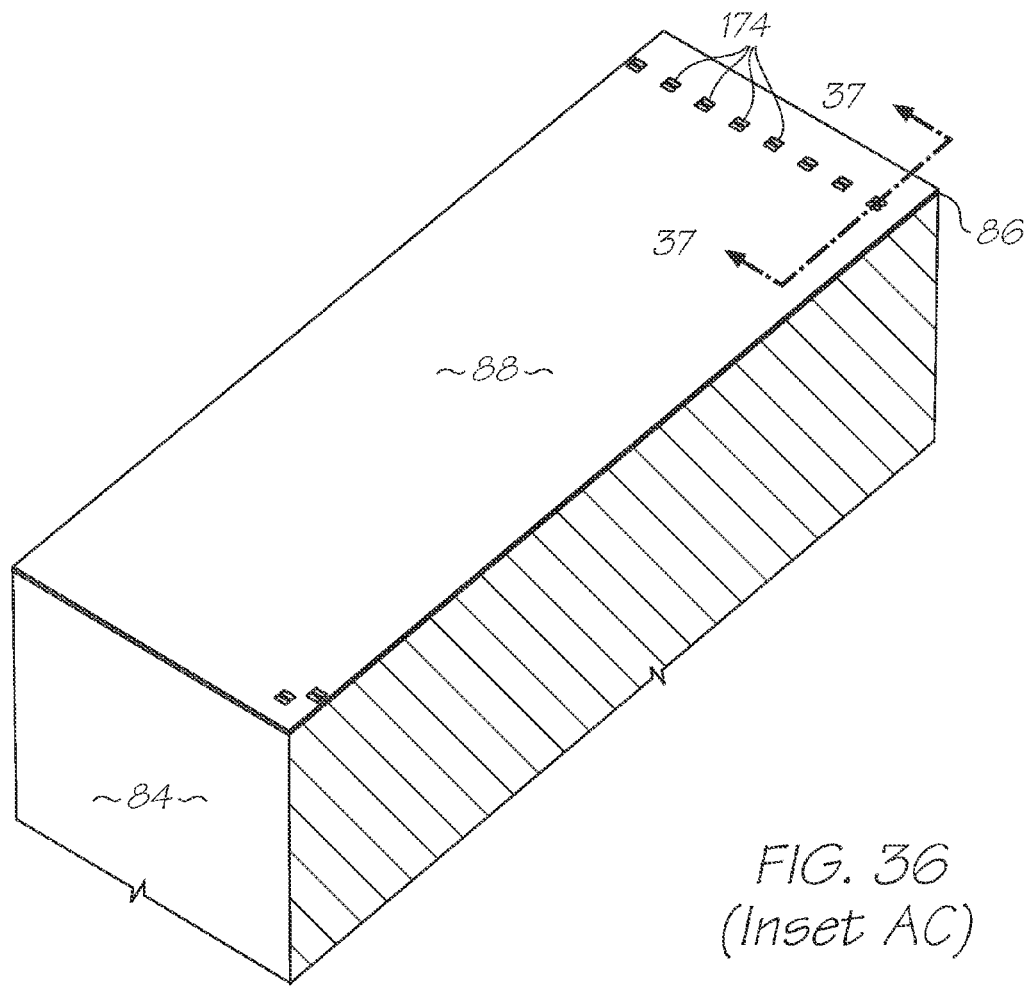
FIG. 36 is a further enlarged view within Inset AC showing the amplification section.

Temperature and liquid sensors are incorporated throughout the LOC device 301 to provide feedback and diagnostics during device operation. Referring to FIG. 35, nine temperature sensors 170 are distributed throughout the amplification section 112. Likewise, the incubation section 114 also has nine temperature sensors 170. These sensors each use a 2×2 array of bipolar junction transistors (BJTs) to monitor the fluid temperature and provide feedback to the CMOS circuitry 86. The CMOS circuitry 86 uses this to precisely control the thermal cycling during the nucleic acid amplification process and any heating during thermal lysis and incubation.

In the hybridization chambers 180, the CMOS circuitry 86 uses the hybridization heaters 182 as temperature sensors (see FIG. 56). The electrical resistance of the hybridization heaters 182 is temperature dependent and the CMOS circuitry 86 uses this to derive a temperature reading for each of the hybridization chambers 180.

Figure 37:
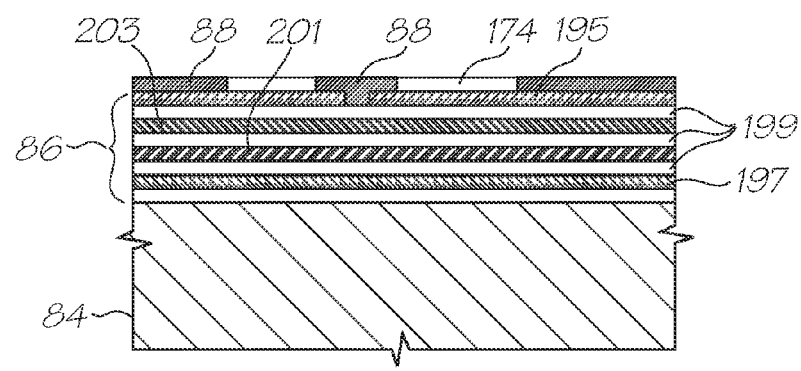
FIG. 37 is a further enlarged view within Inset AC showing the amplification section.
Figure 38:
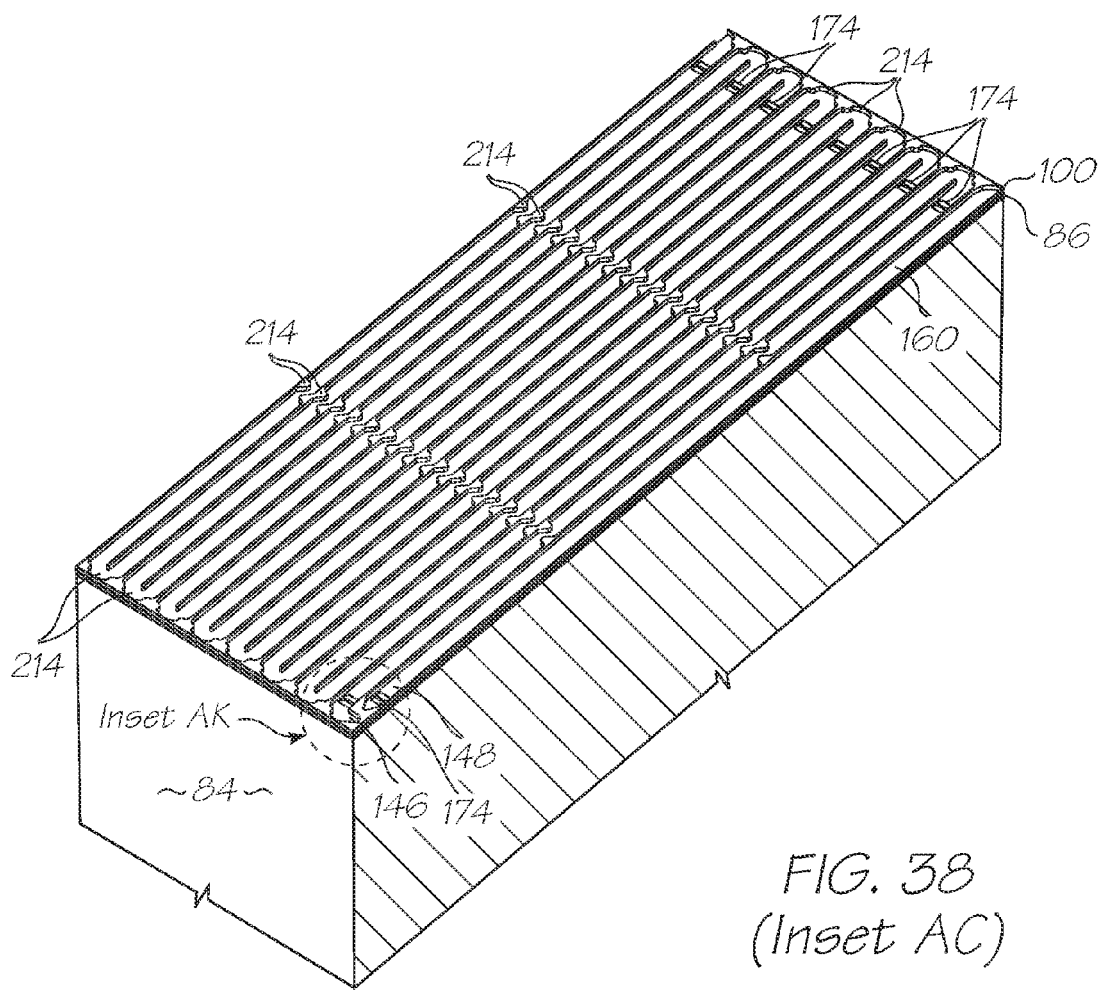
FIG. 38 is a further enlarged view within Inset AC showing the amplification section.
Figure 39:
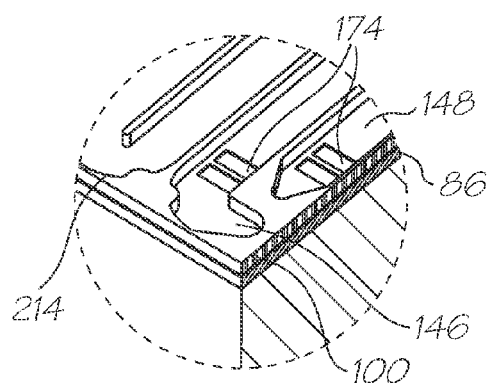
FIG. 39 is a further enlarged view within Inset AK shown in FIG. 38.
Figure 40:
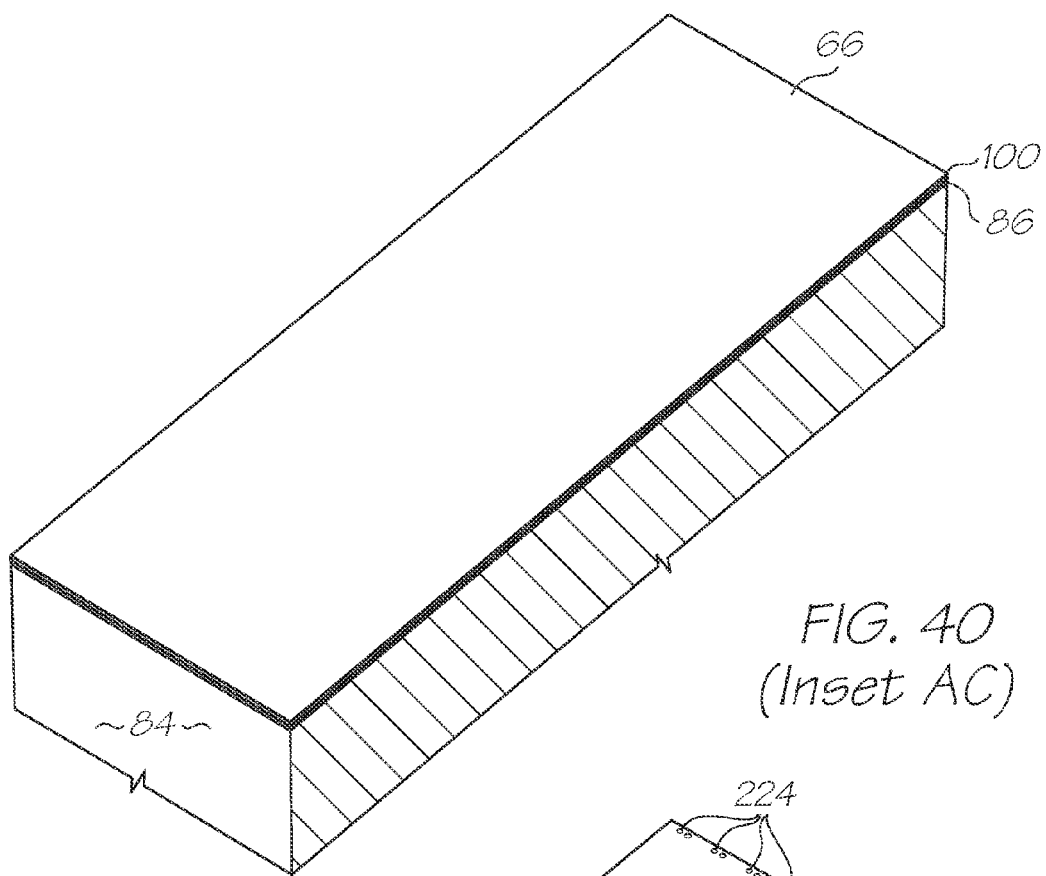
FIG. 40 is a further enlarged view within Inset AC showing the amplification chamber.
Figure 41:
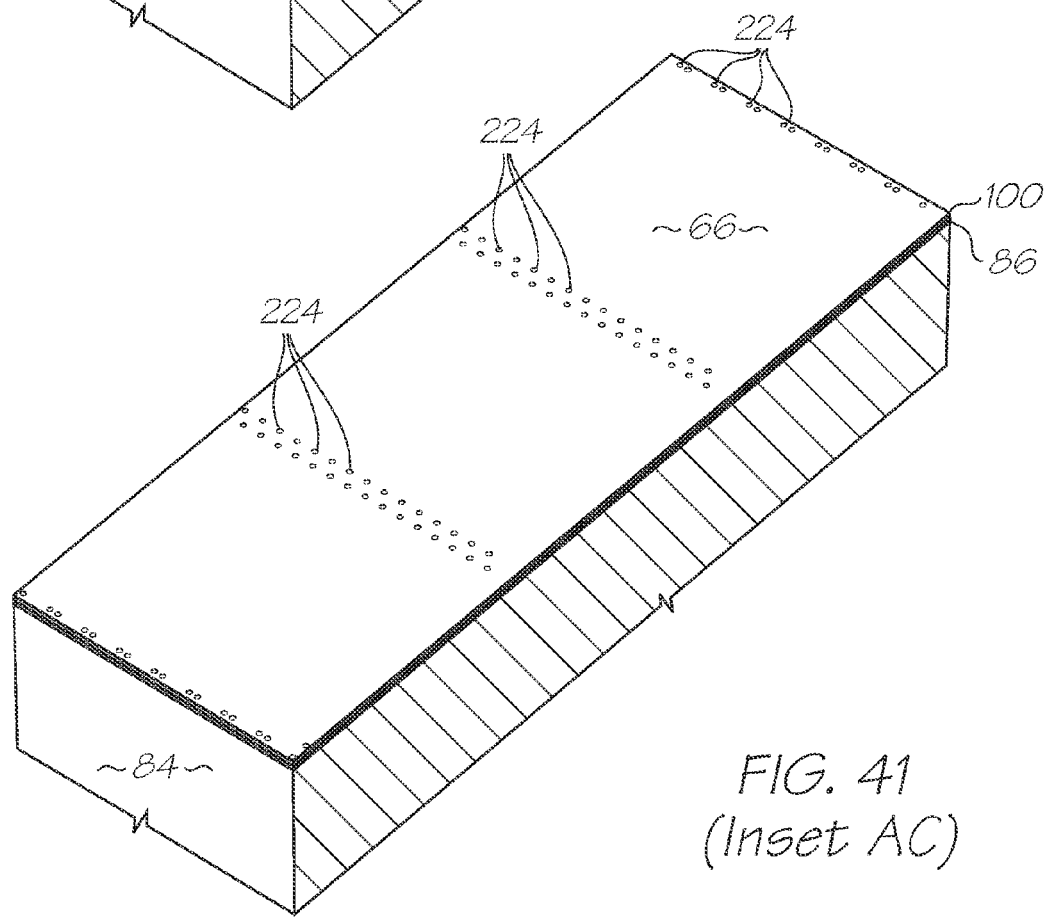
FIG. 41 is a further enlarged view within Inset AC showing the amplification section.
Figure 42:
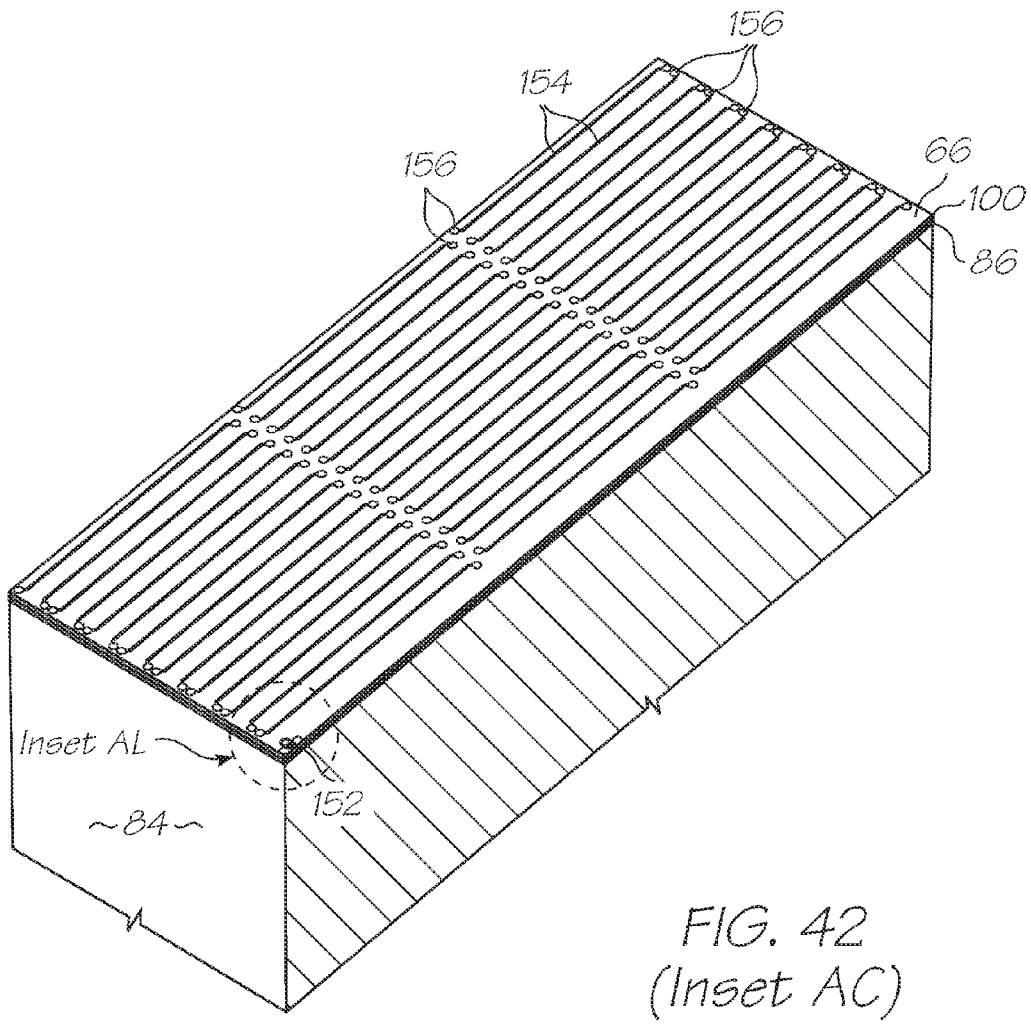
FIG. 42 is a further enlarged view within Inset AC showing the amplification chamber.
Figure 43:
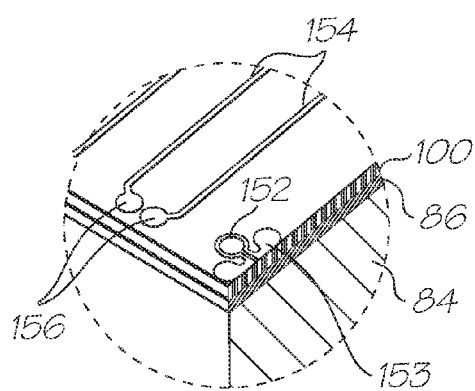
FIG. 43 is a further enlarged view within Inset AL shown in FIG. 42.
Figure 44:
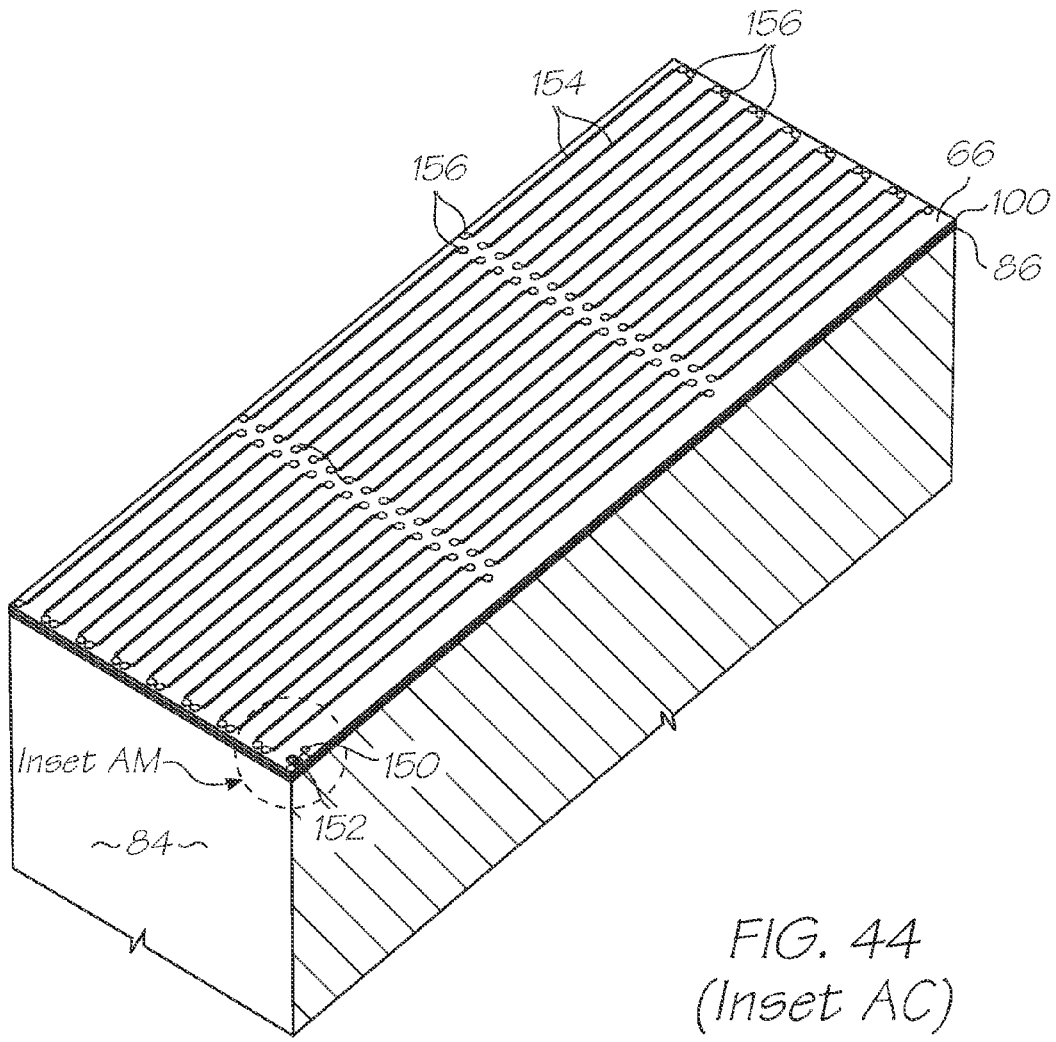
FIG. 44 is a further enlarged view within Inset AC showing the amplification section.
Figure 45:
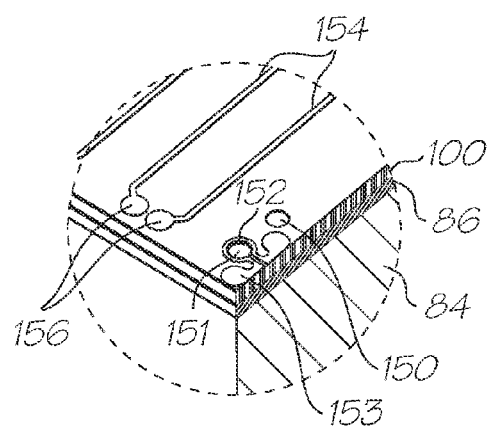
FIG. 45 is a further enlarged view within Inset AM shown in FIG. 44.
Figure 46:
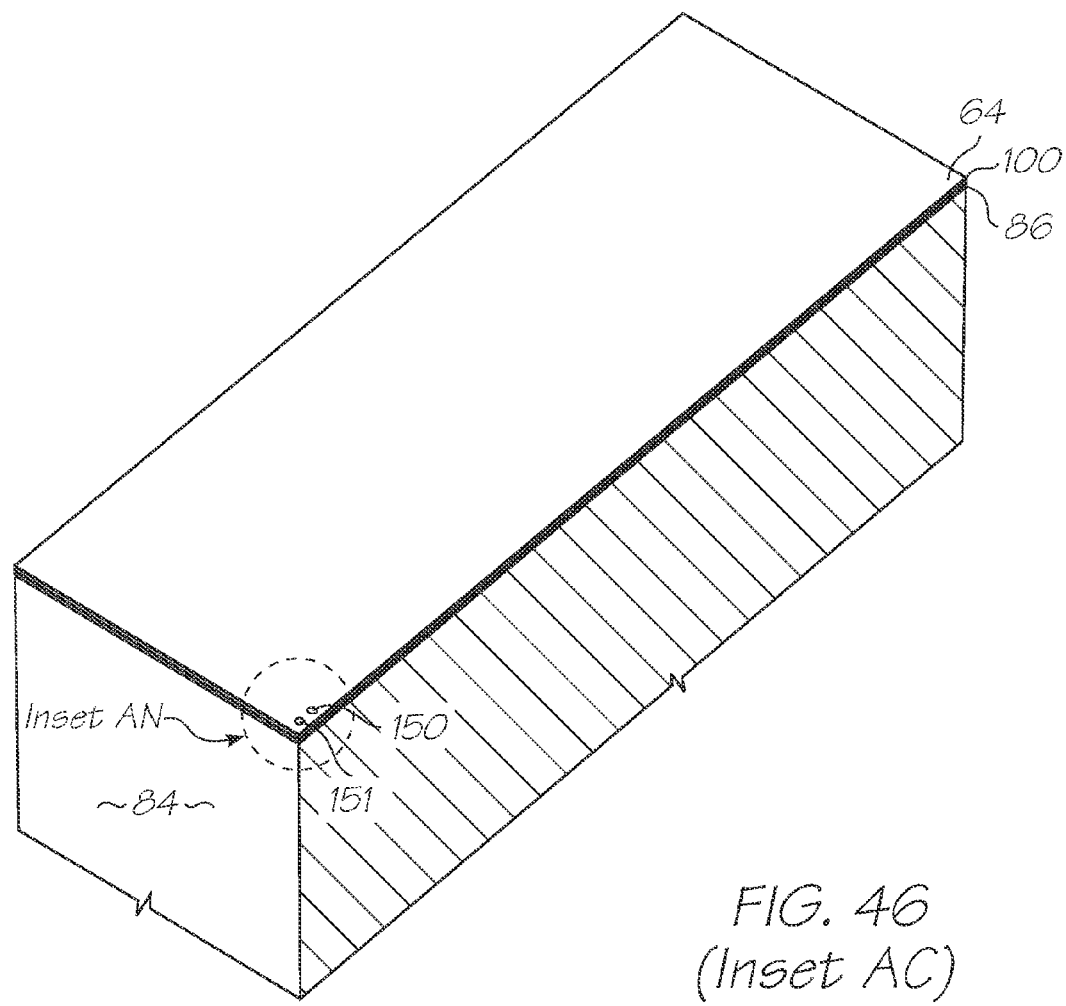
FIG. 46 is a further enlarged view within Inset AC showing the amplification chamber.
Figure 47:
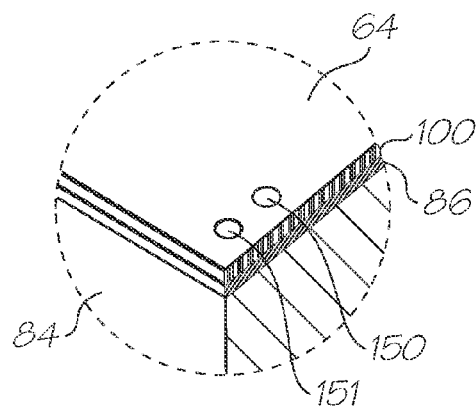
FIG. 47 is a further enlarged view within Inset AN shown in FIG. 46.
Figure 48:
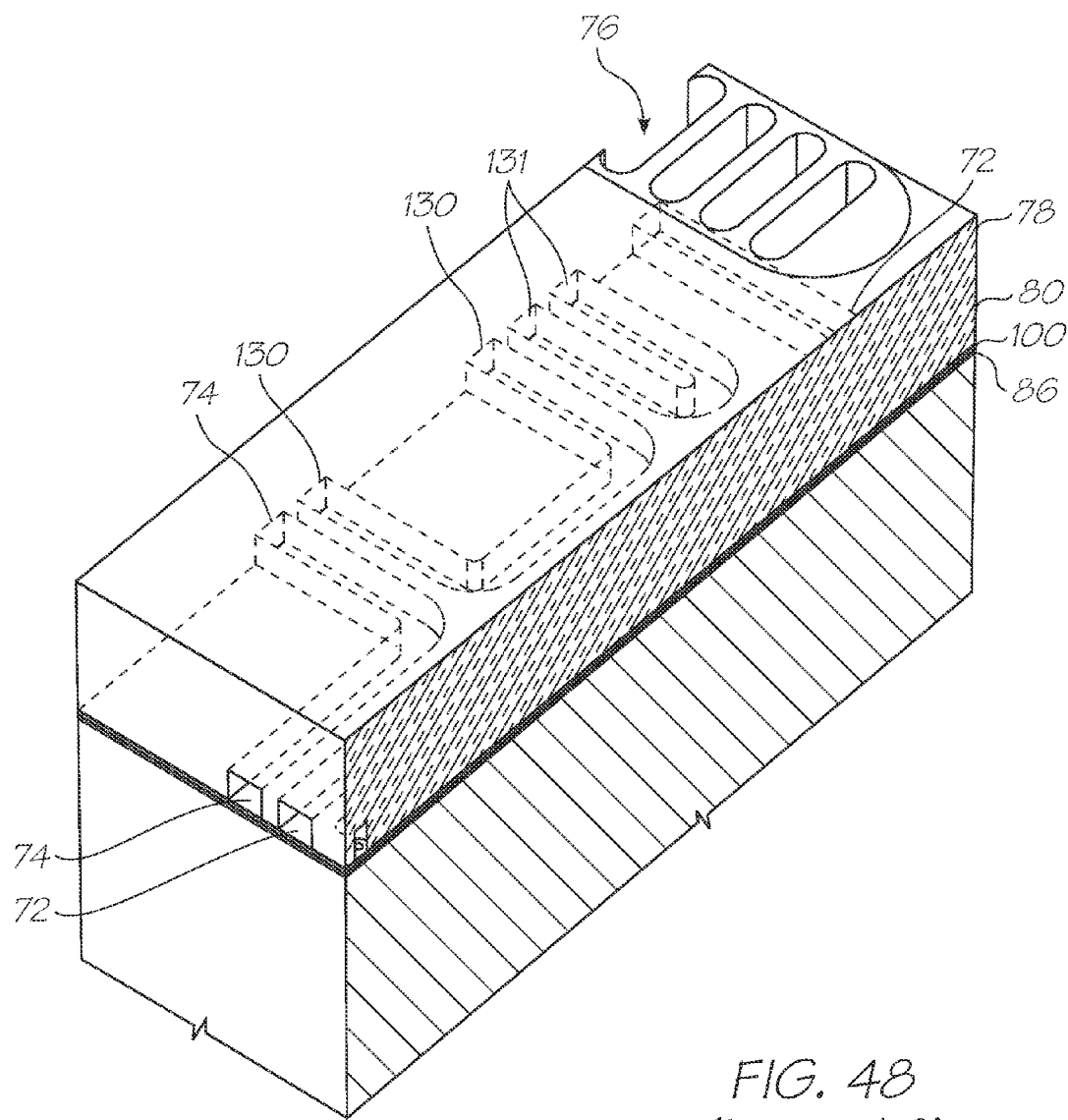
FIG. 48 is a further enlarged view within Inset AC showing the amplification chamber.
Figure 49:
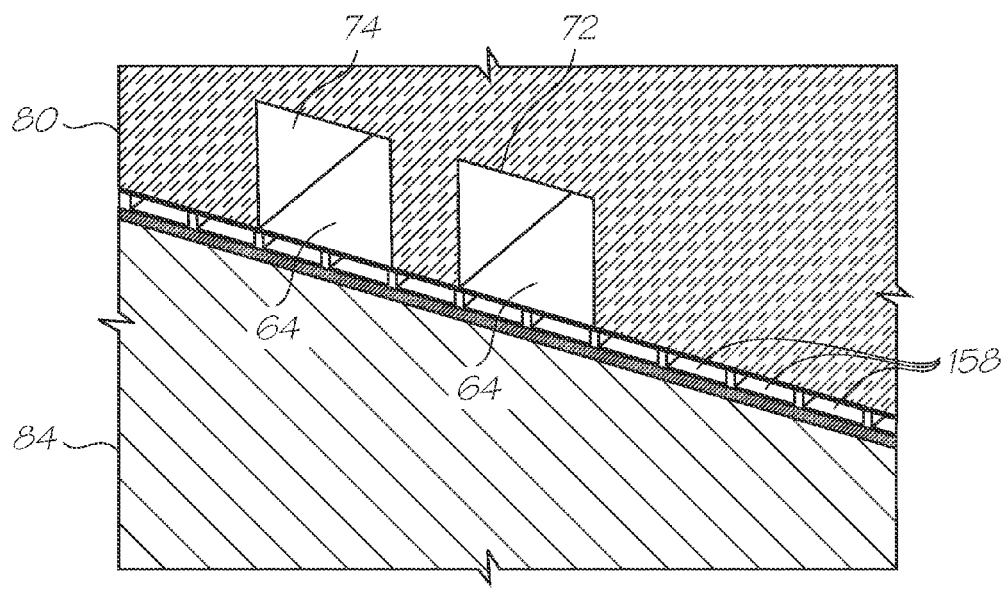
FIG. 49 is a further enlarged view within Inset AC showing the amplification chamber.
Figure 50:
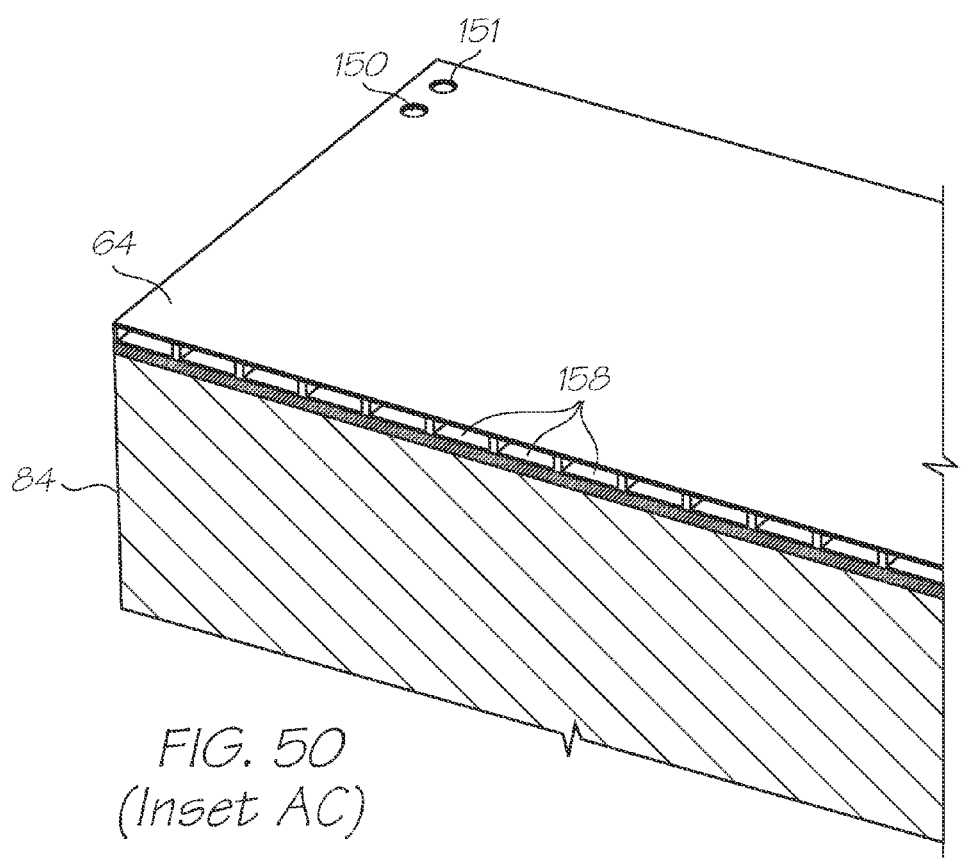
FIG. 50 is a further enlarged view within Inset AC showing the amplification section.

The LOC device 301 also has a number of MST channel liquid sensors 174 and cap channel liquid sensors 208. FIG. 35 shows a line of MST channel liquid sensors 174 at one end of every other meander in the heated microchannel 158. As best shown in FIG. 37, the MST channel liquid sensors 174 are a pair of electrodes formed by exposed areas of the top metal layer 195 in the CMOS structure 86. Liquid closes the circuit between the electrodes to indicate its presence at the sensor's location.

Figure 25:
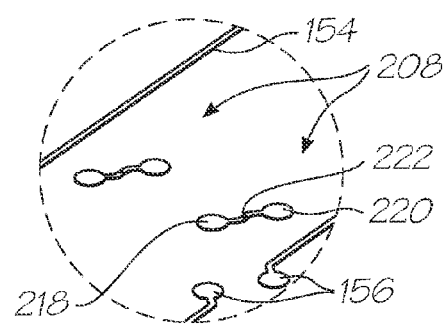
FIG. 25 is a partial perspective illustrating the laminar structure of the LOC device within Inset AI.
Figure 26:
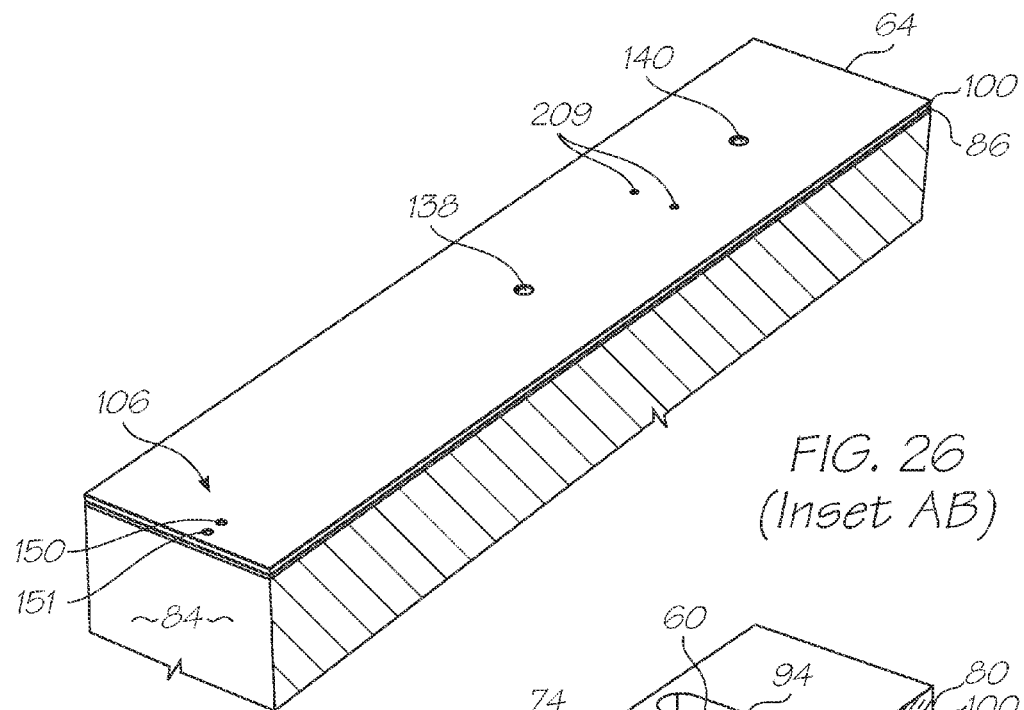
FIG. 26 is a partial perspective illustrating the laminar structure of the LOC device within Inset AB.
Figure 27:
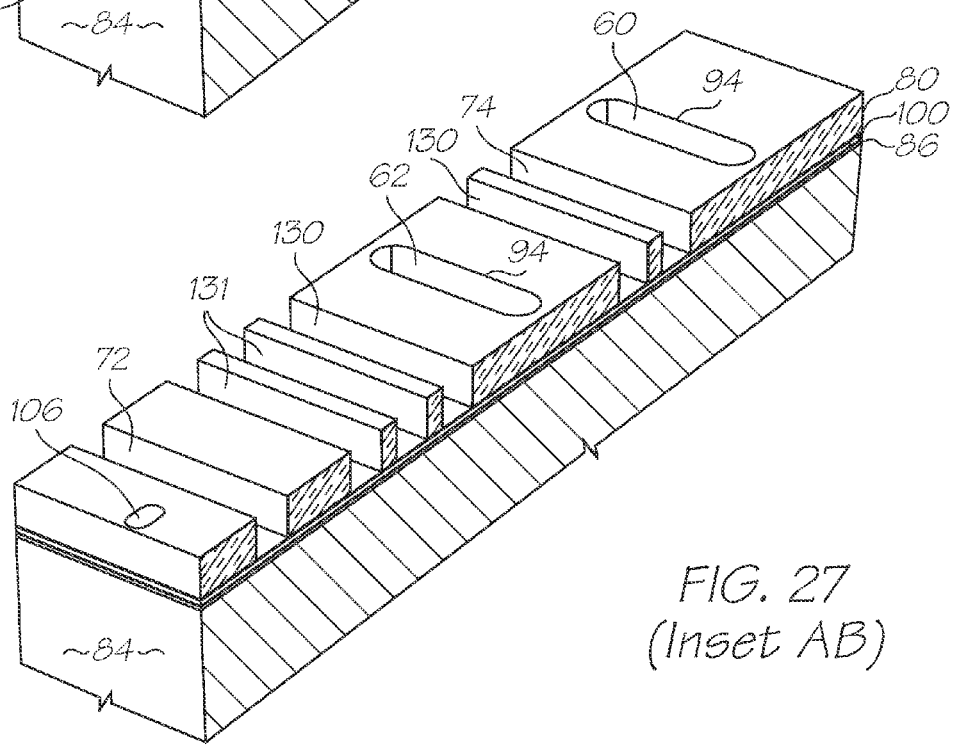
FIG. 27 is a partial perspective illustrating the laminar structure of the LOC device within Inset AB.
Figure 28:
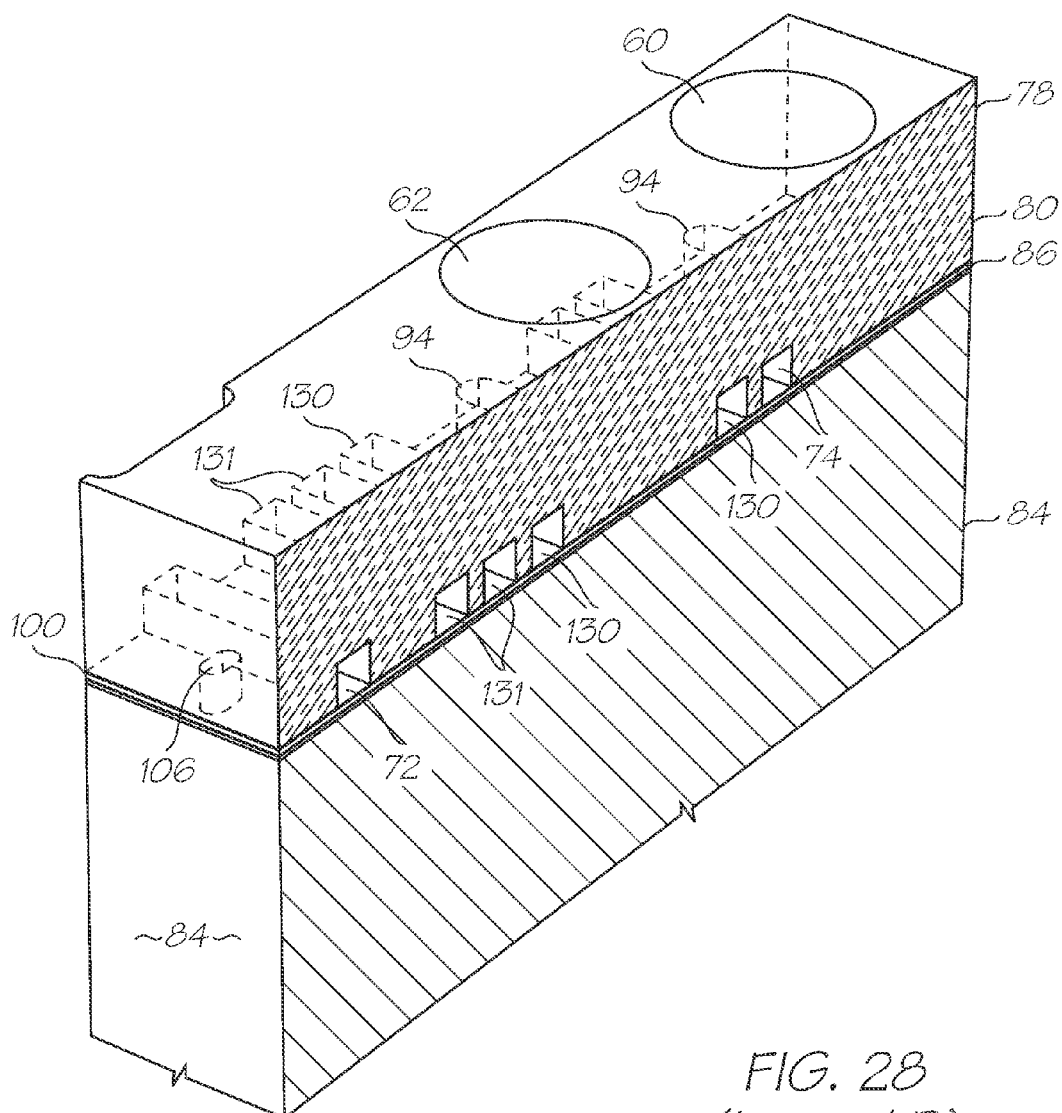
FIG. 28 is a partial perspective illustrating the laminar structure of the LOC device within Inset AB.
Figure 29:
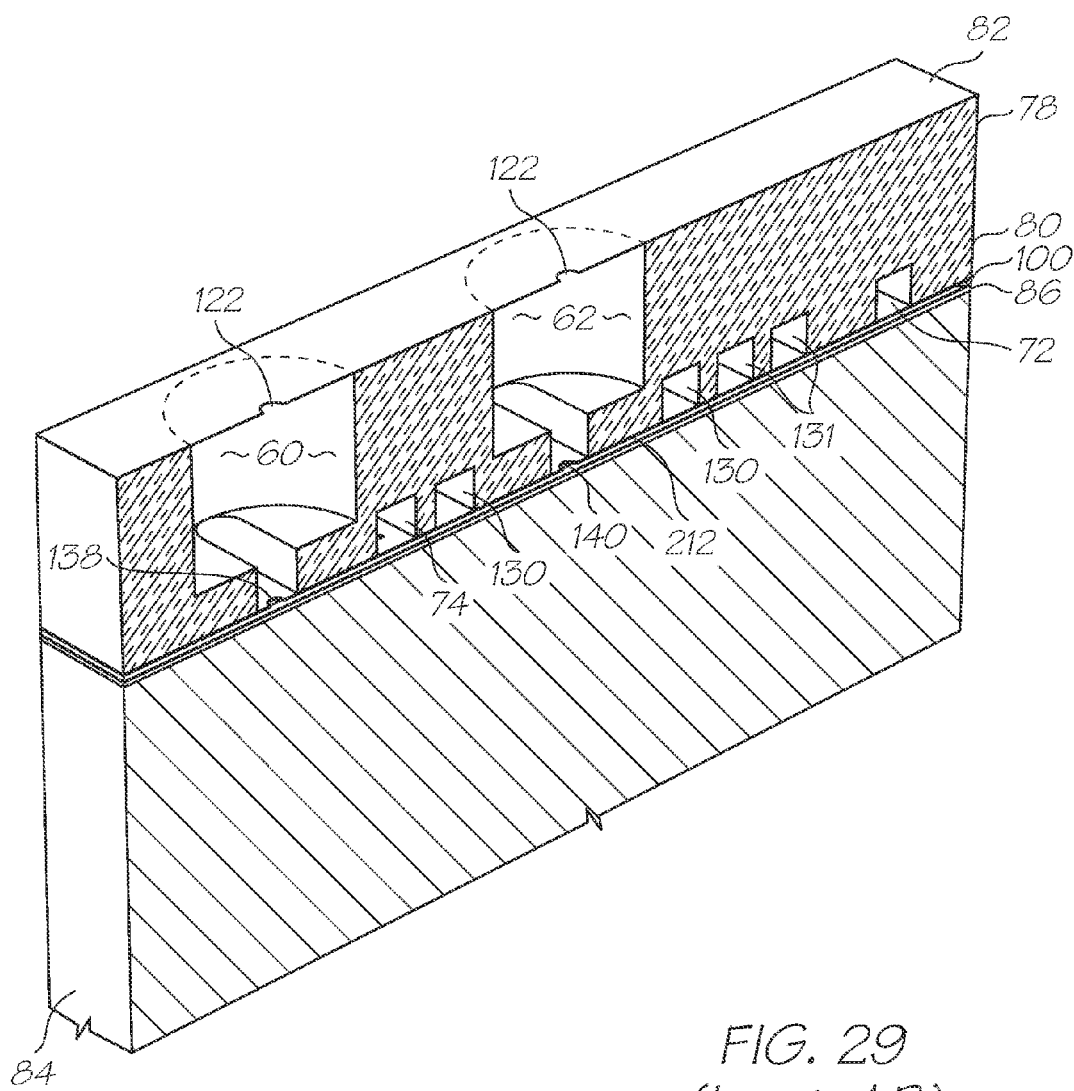
FIG. 29 is a partial perspective illustrating the laminar structure of the LOC device within Inset AB.
Figure 30:
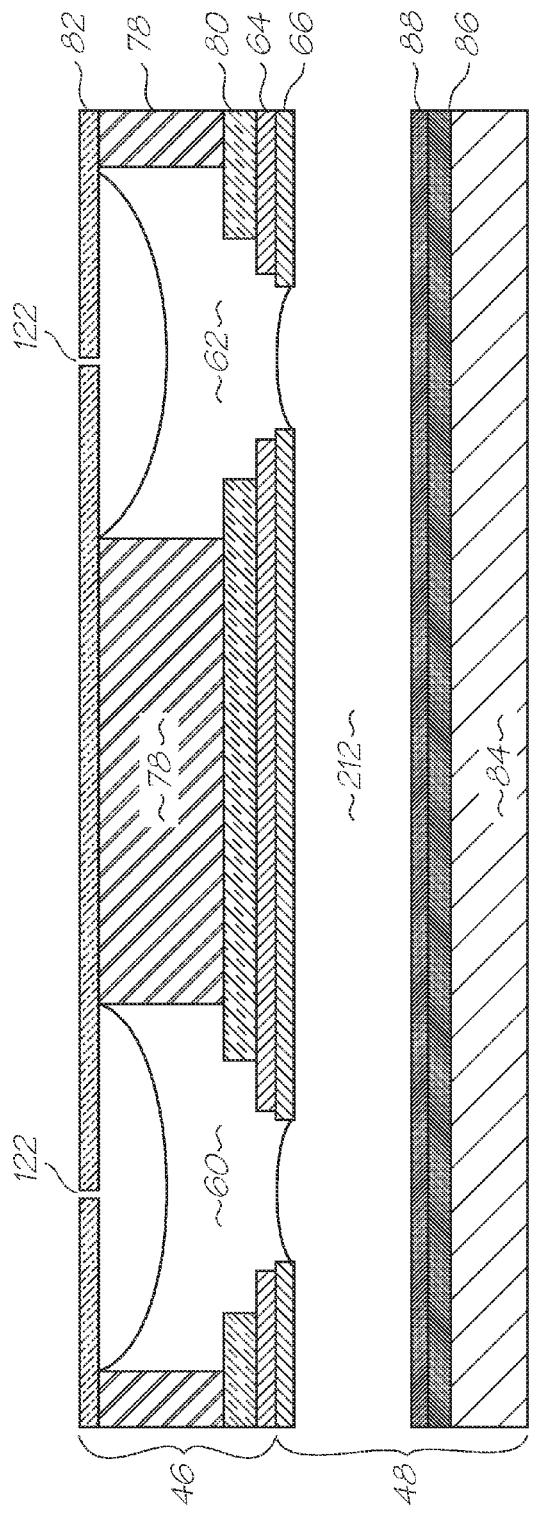
FIG. 30 is a schematic section view of the amplification mix reservoir and the polymerase reservoir.

FIG. 25 shows an enlarged perspective of cap channel liquid sensors 208. Opposing pairs of TiAl electrodes 218 and 220 are deposited on the roof layer 66. Between the electrodes 218 and 220 is a gap 222 to hold the circuit open in the absence of liquid. The presence of liquid closes the circuit and the CMOS circuitry 86 uses this feedback to monitor the flow.

Gravitational Independence

The test modules 10 are orientation independent. They do not need to be secured to a flat stable surface in order to operate. Capillary driven fluid flows and a lack of external plumbing into ancillary equipment allow the modules to be truly portable and simply plugged into a similarly portable hand held reader such as a mobile telephone. Having a gravitationally independent operation means the test modules are also accelerationally independent to all practical extents. They are resistant to shock and vibration and will operate on moving vehicles or while the mobile telephone is being carried around.

Thermal Bend Actuated Valve Variant 1

Figure 64:
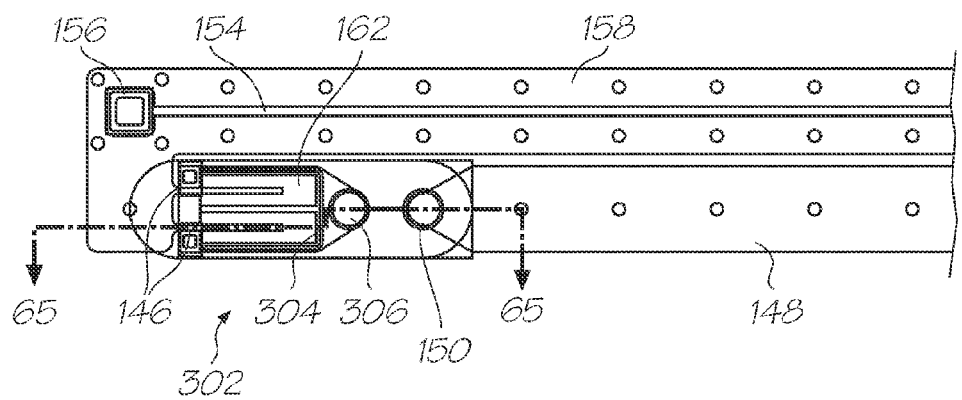
FIG. 64 shows the features of a first variant of a thermal bend actuated valve.
Figure 65:
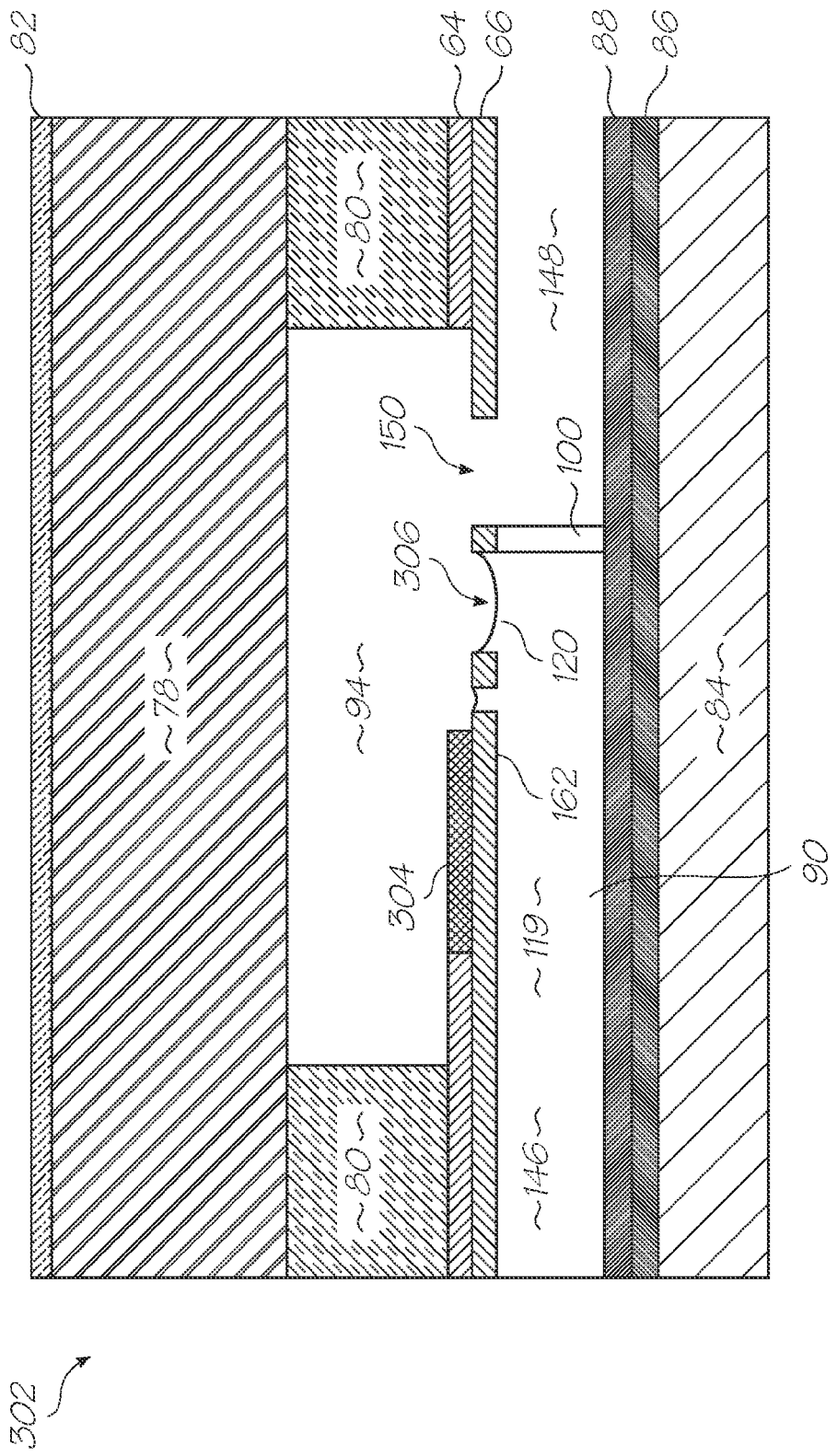
FIG. 65 is a schematic section view of the first variant of a thermal bend actuated valve taken along line 70-70 of FIG. 64.

FIGS. 64 and 65 show a first variant 302 of a thermal bend actuated valve which is a thermal bend actuated pressure pulse valve. FIG. 65 is a schematic section view through line 70-70 shown in FIG. 64. The first variant thermal bend actuated valve 302 has movable member in the form of a CMOS-activated thermal bend actuator 304 of TiAl, TiN or similar resistive heater material. The sample flow enters the valve inlets 146 in the MST channel 90 but stops when a meniscus 120 pins to the aperture 306. The embodiment shown in FIGS. 64 and 65 shows the aperture external to the movable member, but it may also be defined at least partially by the movable member. In this state, the valve is closed. To open the valve, the CMOS circuitry 86 sends a series of electrical pulses to the thermal bend actuator 304. The CMOS-activated thermal bend actuator 304 is bonded to a cantilevered section 162 of the roof layer 66 fixed at the inlet end and free at the aperture end. Differential thermal expansion bends the cantilevered section 162 such that it moves rapidly towards the passivation layer 88. Fluidic drag prevents backflow of the liquid sample 119 which instead, is ejected through the aperture 306 into the cap channel 94. Reciprocating the cantilevered section 162 between the quiescent and displaced positions for a period of time ensures the meniscus 120 unpins from the aperture 306. Sample 119 accumulates in the cap channel 94 until its surfaces are wetted and capillary driven flow resumes. The sample fills the cap channel 94 and then flows to the valve outlet 148 through the valve downtake 150.

Thermal Bend Actuated Valve Variant 2

Figure 66:
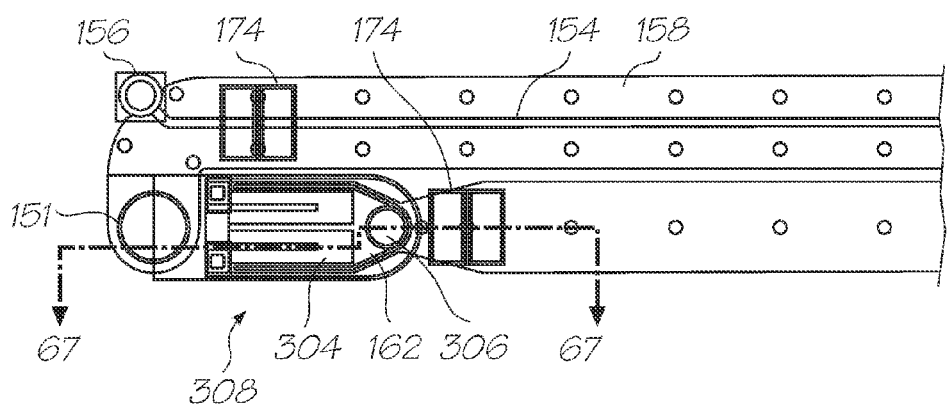
FIG. 66 shows the features of a second variant of a thermal bend actuated valve.
Figure 67:
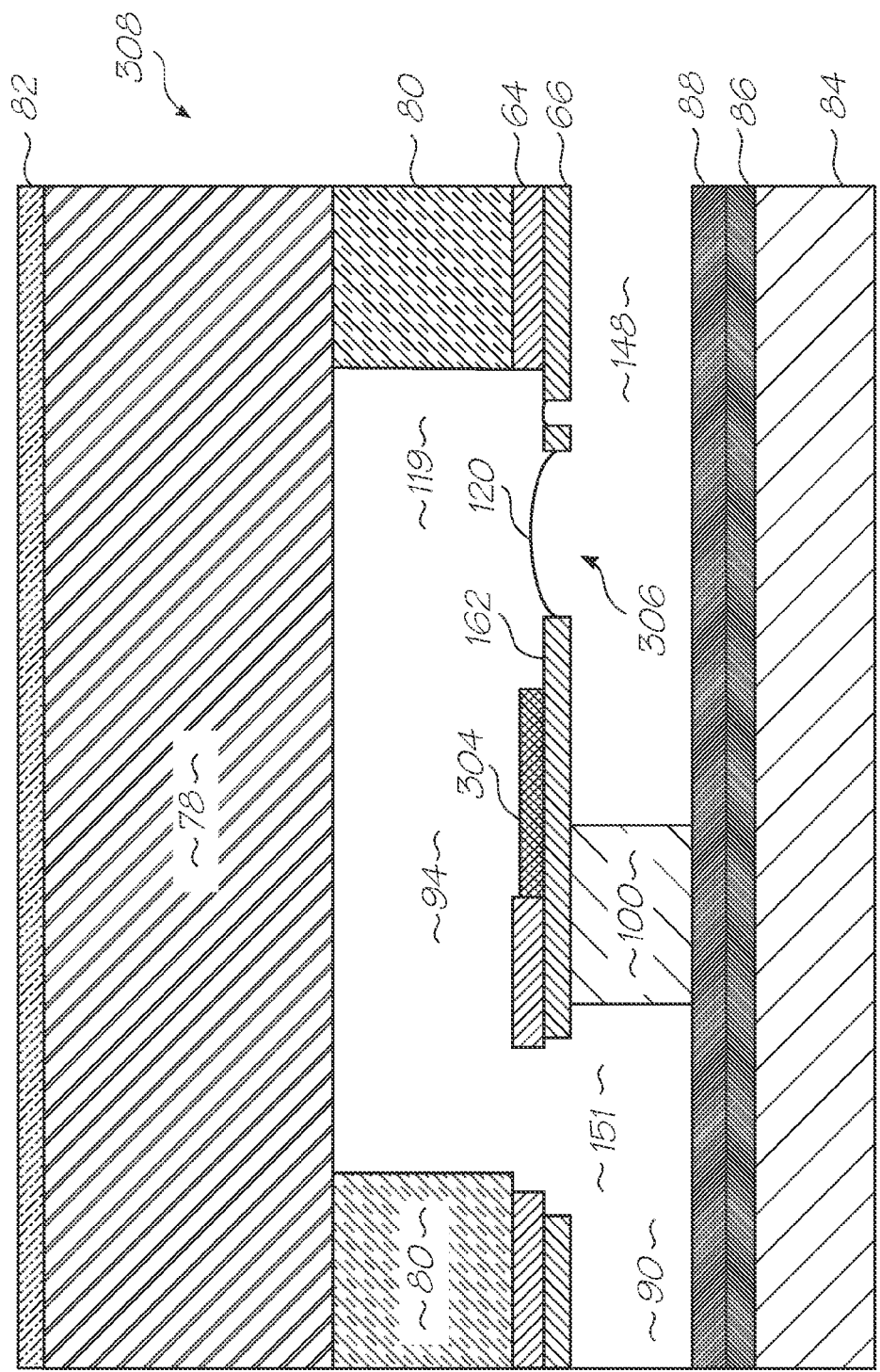
FIG. 67 is a schematic section view of the second variant of a thermal bend actuated valve taken along line 72-72 of FIG. 66.

FIGS. 66 and 67 show a second variant of the thermal bend actuated valve 308 which is a thermal bend actuated surface tension valve. FIG. 67 is a schematic section view through line 72-72 shown in FIG. 66. The second variant of the thermal bend actuated valve 308 has a CMOS-activated thermal bend actuator 304 of TiAl, TiN or similar resistive heater material. The sample flows along the MST channel 90 and into the valve inlet 146 provided by the valve uptake 151. The liquid sample 119 fills the cap channel 94 but stops when a meniscus 120 pins to the aperture 306. In this state, the valve is closed. To open the valve, the CMOS circuitry 86 sends a series of electrical pulses to the thermal bend actuator 304. The CMOS-activated thermal bend actuator 304 is bonded to a cantilevered section 162 of the roof layer 66 fixed at the inlet end and free at the aperture end. Differential thermal expansion bends the cantilevered section 162 such that the aperture 306 moves towards the passivation layer 88. The aperture 306 drags the meniscus 120 from the cap channel 94 into the MST channel 90 to re-establish capillary flow. To re-establish the capillary flow, the channel has opposing side walls that converge to a narrow section immediately downstream of the movable member such that the meniscus contacts the narrow section when the movable member moves to the actuated position. Liquid sensors 174 are placed before and after the valve for diagnostics.

Nucleic Acid Amplification Variants

Direct PCR

Traditionally, PCR requires extensive purification of the target DNA prior to preparation of the reaction mixture. However, with appropriate changes to the chemistry and sample concentration, it is possible to perform nucleic acid amplification with minimal DNA purification, or direct amplification. When the nucleic acid amplification process is PCR, this approach is called direct PCR. In LOC devices where nucleic acid amplification is performed at a controlled, constant temperature, the approach is direct isothermal amplification. Direct nucleic acid amplification techniques have considerable advantages for use in LOC devices, particularly relating to simplification of the required fluidic design. Adjustments to the amplification chemistry for direct PCR or direct isothermal amplification include increased buffer strength, the use of polymerases which have high activity and processivity, and additives which chelate with potential polymerase inhibitors. Dilution of inhibitors present in the sample is also important.

To take advantage of direct nucleic acid amplification techniques, the LOC device designs incorporate two additional features. The first feature is reagent reservoirs (for example reservoir 58 in FIG. 8) which are appropriately dimensioned to supply a sufficient quantity of amplification reaction mix, or diluent, so that the final concentrations of sample components which might interfere with amplification chemistry are low enough to permit successful nucleic acid amplification. The desired dilution of non-cellular sample components is in the range of 5× to 20×. Different LOC structures, for example the pathogen dialysis section 70 in FIG. 4, are used when appropriate to ensure that the concentration of target nucleic acid sequences is maintained at a high enough level for amplification and detection. In this embodiment, further illustrated in FIG. 6, a dialysis section which effectively concentrates pathogens small enough to be passed into the amplification section 292 is employed upstream of the sample extraction section 290, and rejects larger cells to a waste receptacle 76. In another embodiment, a dialysis section is used to selectively deplete proteins and salts in blood plasma while retaining cells of interest.

The second LOC structural feature which supports direct nucleic acid amplification is design of channel aspect ratios to adjust the mixing ratio between the sample and the amplification mix components. For example, to ensure dilution of inhibitors associated with the sample in the preferred 5×-20× range through a single mixing step, the length and cross-section of the sample and reagent channels are designed such that the sample channel, upstream of the location where mixing is initiated, constitutes a flow impedance 4×-19× higher than the flow impedance of the channels through which the reagent mixture flows. Control over flow impedances in microchannels is readily achieved through control over the design geometry. The flow impedance of a microchannel increases linearly with the channel length, for a constant cross-section. Importantly for mixing designs, flow impedance in microchannels depends more strongly on the smallest cross-sectional dimension. For example, the flow impedance of a microchannel with rectangular cross-section is inversely proportional to the cube of the smallest perpendicular dimension, when the aspect ratio is far from unity.

Reverse-Transcriptase PCR (RT-PCR)

Where the sample nucleic acid species being analysed or extracted is RNA, such as from RNA viruses or messenger RNA, it is first necessary to reverse transcribe the RNA into complementary DNA (cDNA) prior to PCR amplification. The reverse transcription reaction can be performed in the same chamber as the PCR (one-step RT-PCR) or it can be performed as a separate, initial reaction (two-step RT-PCR). In the LOC variants described herein, a one-step RT-PCR can be performed simply by adding the reverse transcriptase to reagent reservoir 62 along with the polymerase and programming the heaters 154 to cycle firstly for the reverse transcription step and then progress onto the nucleic acid amplification step. A two-step RT-PCR could also be easily achieved by utilizing the reagent reservoir 58 to store and dispense the buffers, primers, dNTPs and reverse transcriptase and the incubation section 114 for the reverse transcription step followed by amplification in the normal way in the amplification section 112.

Isothermal Nucleic Acid Amplification

For some applications, isothermal nucleic acid amplification is the preferred method of nucleic acid amplification, thus avoiding the need to repetitively cycle the reaction components through various temperature cycles but instead maintaining the amplification section at a constant temperature, typically around 37° C. to 41° C. A number of isothermal nucleic acid amplification methods have been described, including Strand Displacement Amplification (SDA), Transcription Mediated Amplification (TMA), Nucleic Acid Sequence Based Amplification (NASBA), Recombinase Polymerase Amplification (RPA), Helicase-Dependent isothermal DNA Amplification (HDA), Rolling Circle Amplification (RCA), Ramification Amplification (RAM) and Loop-mediated Isothermal Amplification (LAMP), and any of these, or other isothermal amplification methods, can be employed in particular embodiments of the LOC device described herein.

In order to perform isothermal nucleic acid amplification, the reagent reservoirs 60 and 62 adjoining the amplification section will be loaded with the appropriate reagents for the specified isothermal method instead of PCR amplification mix and polymerase. For example, for SDA, reagent reservoir 60 contains amplification buffer, primers and dNTPs and reagent reservoir 62 contains an appropriate nickase enzyme and Exo-DNA polymerase. For RPA, reagent reservoir 60 contains the amplification buffer, primers, dNTPs and recombinase proteins, with reagent reservoir 62 containing a strand displacing DNA polymerase such as Bsu. Similarly, for HDA, reagent reservoir 60 contains amplification buffer, primers and dNTPs and reagent reservoir 62 contains an appropriate DNA polymerase and a helicase enzyme to unwind the double stranded DNA strand instead of using heat. The skilled person will appreciate that the necessary reagents can be split between the two reagent reservoirs in any manner appropriate for the nucleic acid amplification process.

For amplification of viral nucleic acids from RNA viruses such as HIV or hepatitis C virus, NASBA or TMA is appropriate as it is unnecessary to first transcribe the RNA to cDNA. In this example, reagent reservoir 60 is filled with amplification buffer, primers and dNTPs and reagent reservoir 62 is filled with RNA polymerase, reverse transcriptase and, optionally, RNase H.

For some forms of isothermal nucleic acid amplification it may be necessary to have an initial denaturation cycle to separate the double stranded DNA template, prior to maintaining the temperature for the isothermal nucleic acid amplification to proceed. This is readily achievable in all embodiments of the LOC device described herein, as the temperature of the mix in the amplification section 112 can be carefully controlled by the heaters 154 in the amplification microchannels 158 (see FIG. 14).

Figure 82:
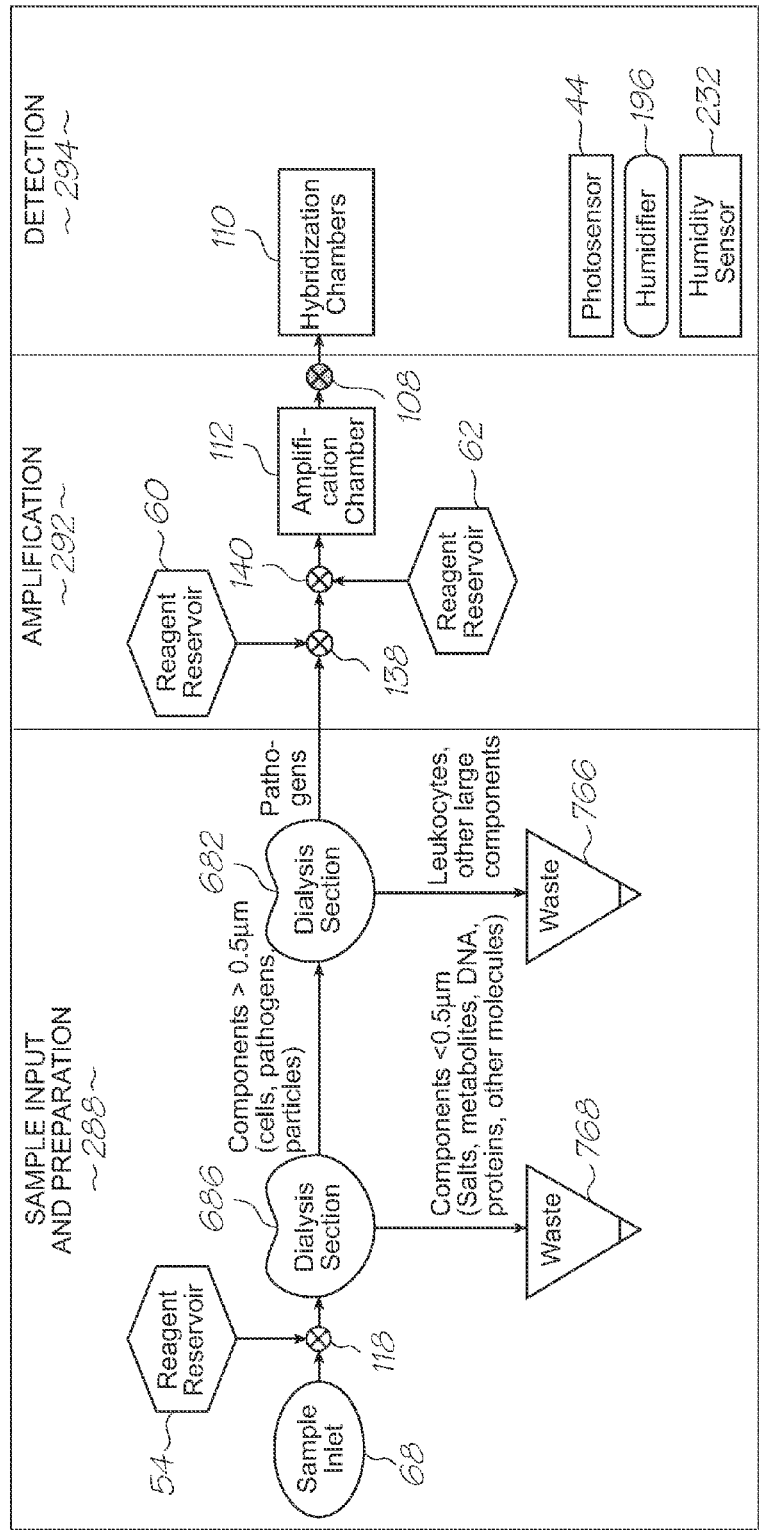
FIG. 82 is a schematic illustration of the architecture of LOC variant XLIII.
Figure 83:
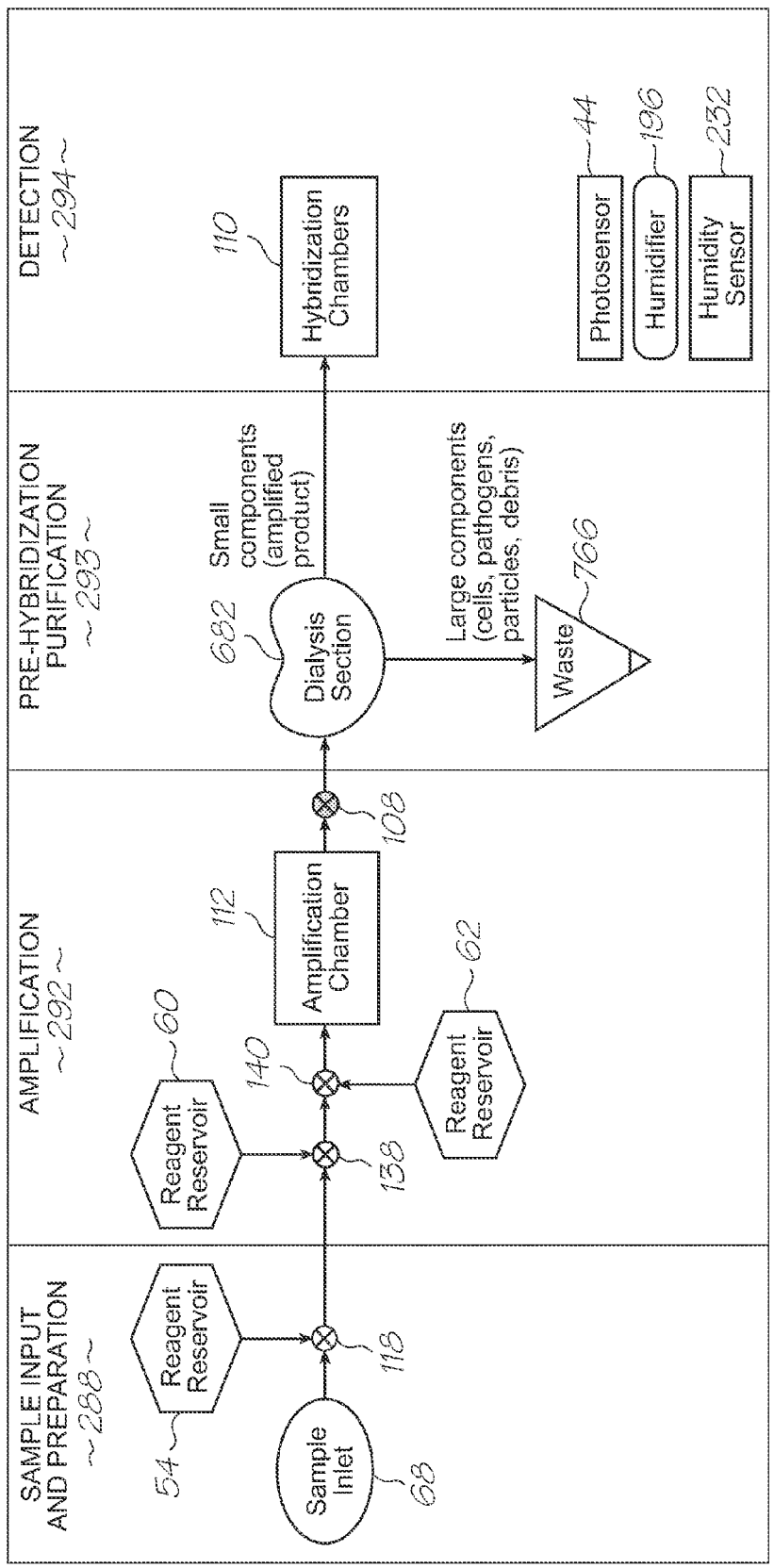
FIG. 83 is a schematic illustration of the architecture of LOC variant XLIV.
Figure 84:
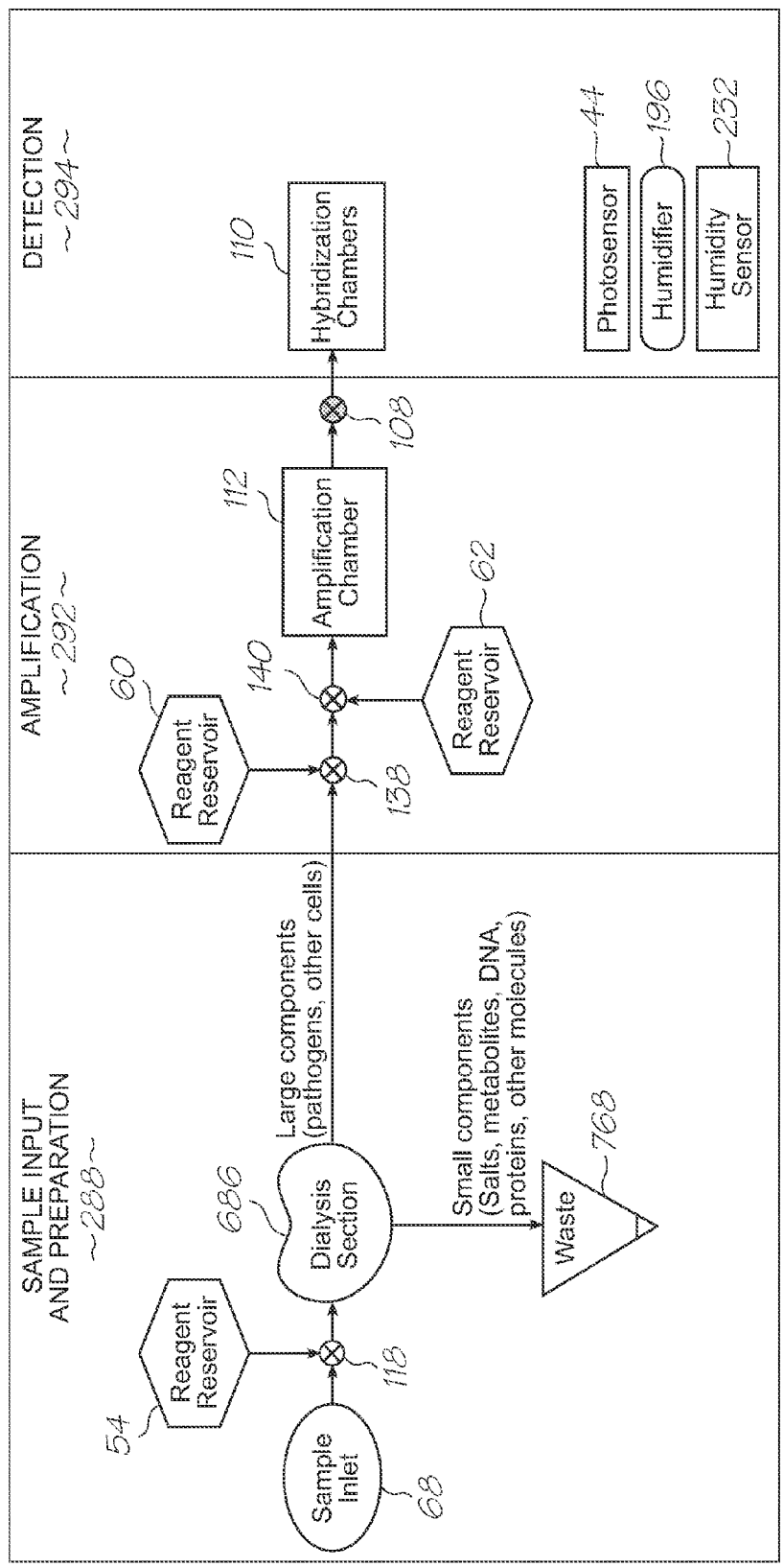
FIG. 84 is a schematic illustration of the architecture of LOC variant XLVII.

Isothermal nucleic acid amplification is more tolerant of potential inhibitors in the sample and, as such, is generally suitable for use where direct nucleic acid amplification from the sample is desired. Therefore, isothermal nucleic acid amplification is sometimes useful in LOC variant XLIII 673, LOC variant XLIV 674 and LOC variant XLVII 677, amongst others, shown in FIGS. 82, 83 and 84, respectively. Direct isothermal amplification may also be combined with one or more pre-amplification dialysis steps 70, 686 or 682 as shown in FIGS. 82 and 84 and/or a pre-hybridization dialysis step 682 as indicated in FIG. 83 to help partially concentrate the target cells in the sample before nucleic acid amplification or remove unwanted cellular debris prior to the sample entering the hybridization chamber array 110, respectively. The person skilled in the art will appreciate that any combination of pre-amplification dialysis and pre-hybridization dialysis can be used.

Figure 78:
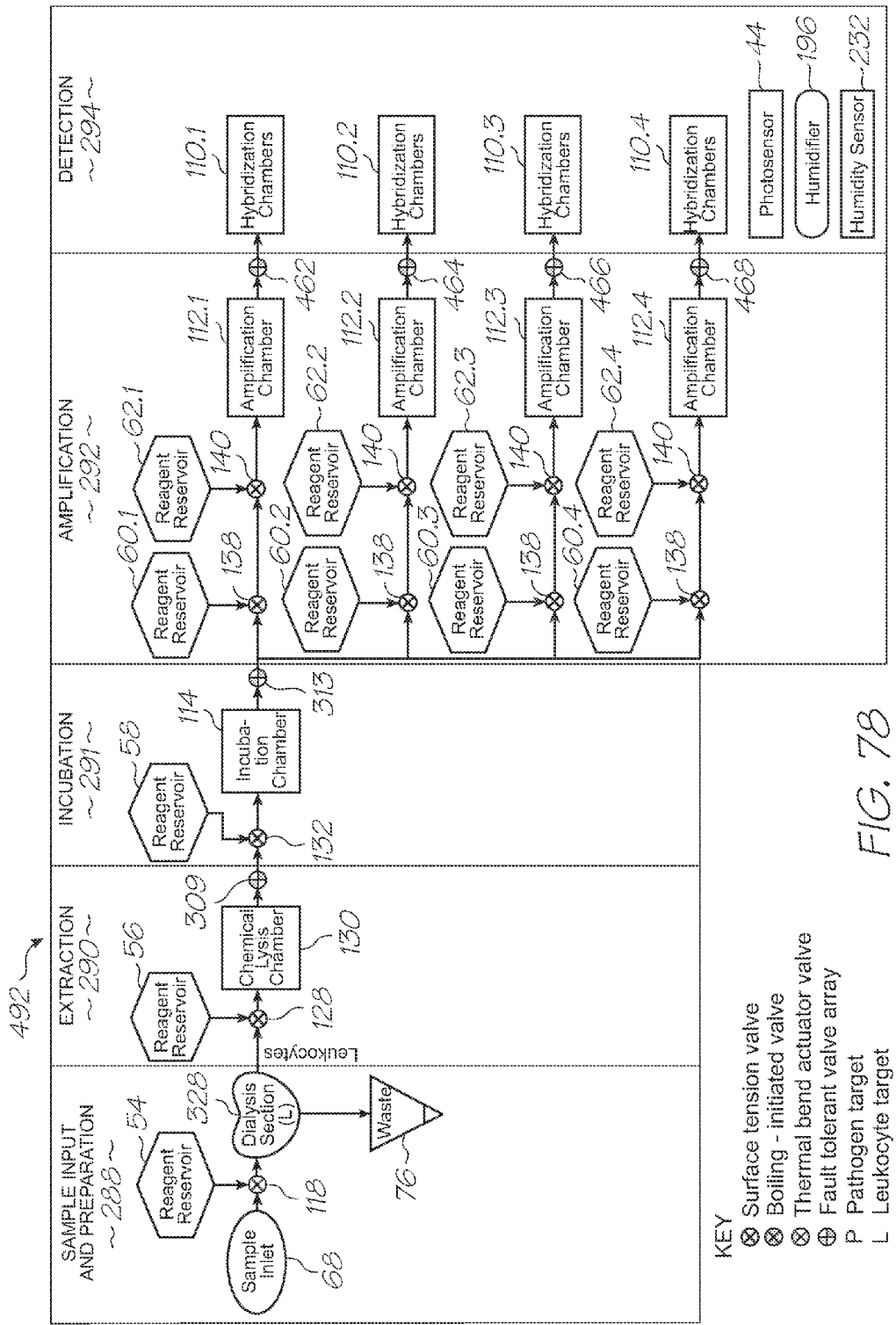
FIG. 78 is a diagrammatic representation of the architecture of LOC variant VII.
Figure 79:
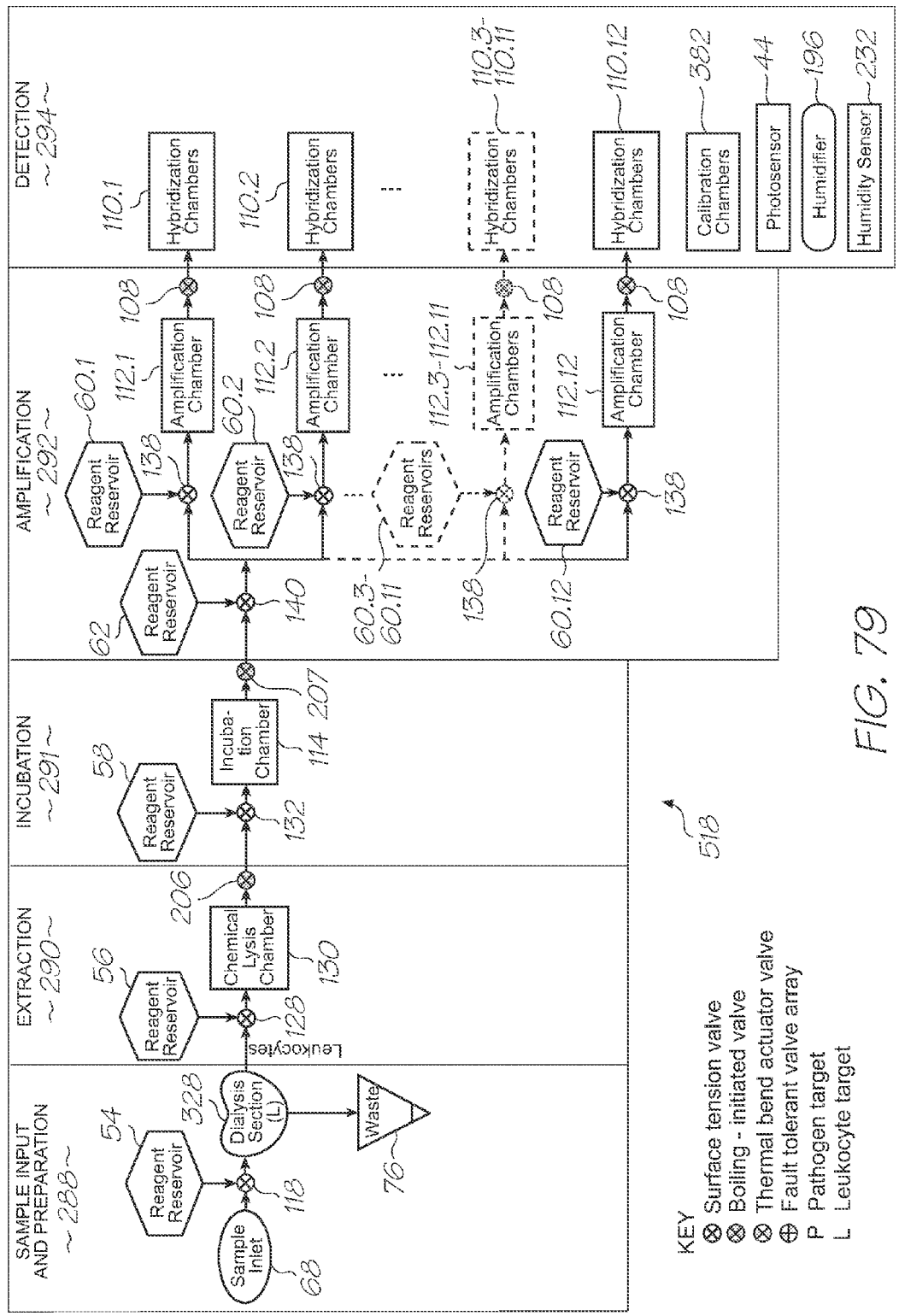
FIG. 79 is a diagrammatic representation of the architecture of LOC variant VIII.
Figure 80:
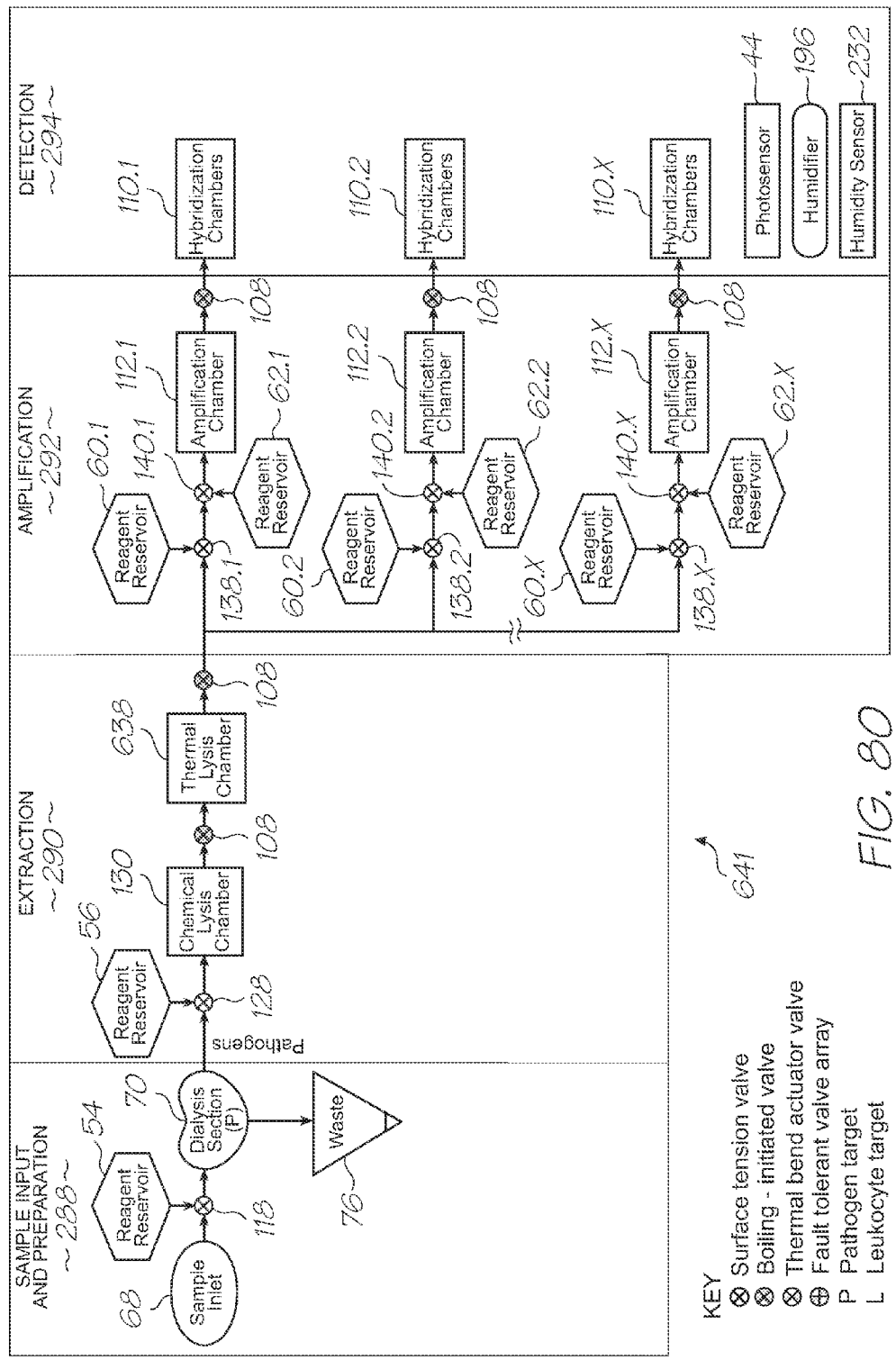
FIG. 80 is a schematic illustration of the architecture of LOC variant XIV.

Isothermal nucleic acid amplification can also be performed in parallel amplification sections such as those schematically represented in FIGS. 78, 79 and 80, multiplexed and some methods of isothermal nucleic acid amplification, such as LAMP, are compatible with an initial reverse transcription step to amplify RNA.

Additional Details on the Fluorescence Detection System

Figure 58:
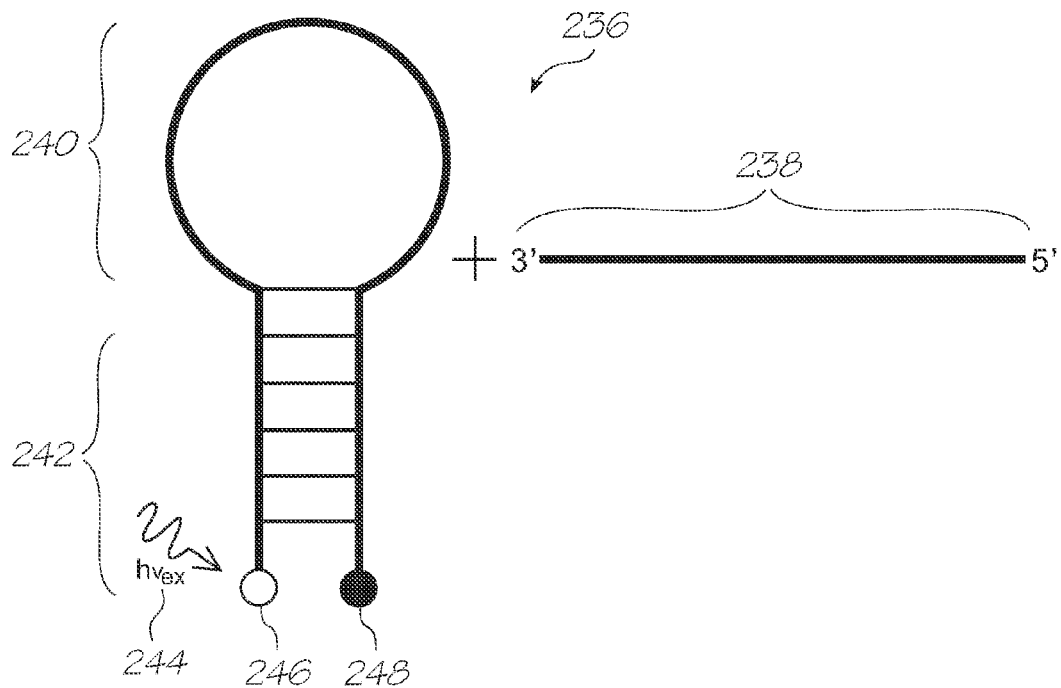
FIG. 58 is a diagram of a FRET probe in a closed configuration.
Figure 59:
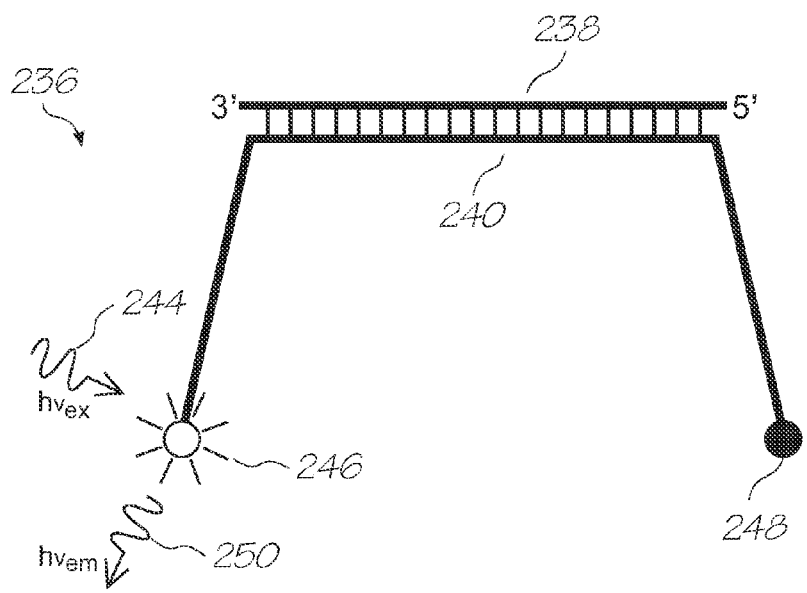
FIG. 59 is a diagram of a FRET probe in an open and hybridized configuration.

FIGS. 58 and 59 show the hybridization-responsive FRET probes 236. These are often referred to as molecular beacons and are stem-and-loop probes, generated from a single strand of nucleic acid, that fluoresce upon hybridization to complementary nucleic acids. FIG. 58 shows a single FRET probe 236 prior to hybridization with a target nucleic acid sequence 238. The probe has a loop 240, stem 242, a fluorophore 246 at the 5' end, and a quencher 248 at the 3' end. The loop 240 consists of a sequence complementary to the target nucleic acid sequence 238. Complementary sequences on either side of the probe sequence anneal together to form the stem 242.

In the absence of a complementary target sequence, the probe remains closed as shown in FIG. 58. The stem 242 keeps the fluorophore-quencher pair in close proximity to each other, such that significant resonant energy transfer can occur between them, substantially eliminating the ability of the fluorophore to fluoresce when illuminated with the excitation light 244.

FIG. 59 shows the FRET probe 236 in an open or hybridized configuration. Upon hybridization to a complementary target nucleic acid sequence 238, the stem-and-loop structure is disrupted, the fluorophore and quencher are spatially separated, thus restoring the ability of the fluorophore 246 to fluoresce. The fluorescence emission 250 is optically detected as an indication that the probe has hybridized.

The probes hybridize with very high specificity with complementary targets, since the stem helix of the probe is designed to be more stable than a probe-target helix with a single nucleotide that is not complementary. Since double-stranded DNA is relatively rigid, it is sterically impossible for the probe-target helix and the stem helix to coexist.

Primer-Linked Probes

Primer-linked, stem-and-loop probes and primer-linked, linear probes, otherwise known as scorpion probes, are an alternative to molecular beacons and can be used for real-time and quantitative nucleic acid amplification in the LOC device. Real-time amplification could be performed directly in the hybridization chambers of the LOC device. The benefit of using primer-linked probes is that the probe element is physically linked to the primer, thus only requiring a single hybridization event to occur during the nucleic acid amplification rather than separate hybridizations of the primers and probes being required. This ensures that the reaction is effectively instantaneous and results in stronger signals, shorter reaction times and better discrimination than when using separate primers and probes. The probes (along with polymerase and the amplification mix) would be deposited into the hybridization chambers 180 during fabrication and there would be no need for a separate amplification section on the LOC device. Alternatively, the amplification section is left unused or used for other reactions.

Primer-Linked Linear Probe

Figure 85:
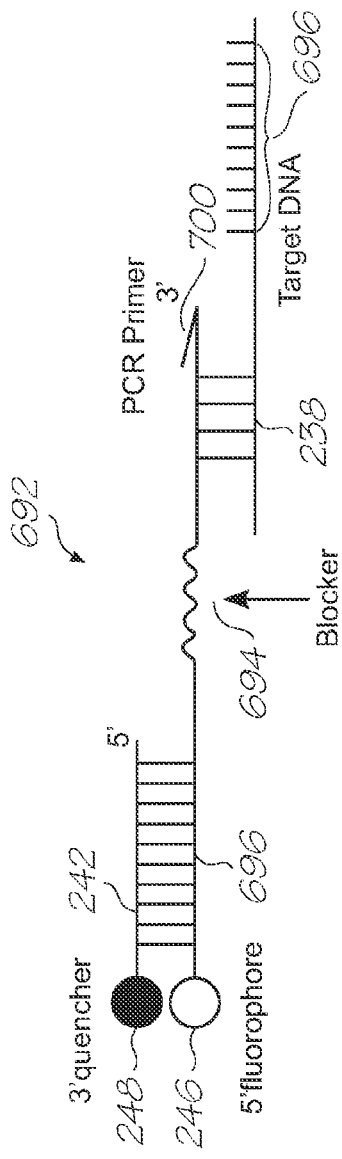
FIG. 85 is a diagram of a primer-linked, linear fluorescent probe during the initial round of amplification.
Figure 86:
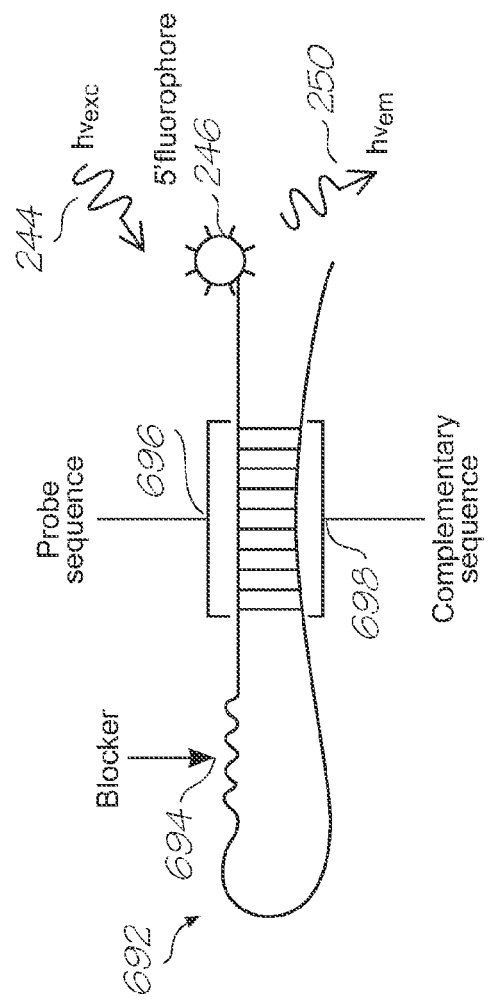
FIG. 86 is a diagram of a primer-linked, linear fluorescent probe during a subsequent amplification cycle.

FIGS. 85 and 86 show a primer-linked linear probe 692 during the initial round of nucleic acid amplification and in its hybridized configuration during subsequent rounds of nucleic acid amplification, respectively. Referring to FIG. 85, the primer-linked linear probe 692 has a double-stranded stem segment 242. One of the strands incorporates the primer linked probe sequence 696 which is homologous to a region on the target nucleic acid 696 and is labelled on its 5' end with fluorophore 246, and linked on its 3' end to an oligonucleotide primer 700 via an amplification blocker 694. The other strand of the stem 242 is labelled at its 3 end with a quencher moiety 248. After an initial round of nucleic acid amplification has completed, the probe can loop around and hybridize to the extended strand with the, now complementary, sequence 698.

During the initial round of nucleic acid amplification, the oligonucleotide primer 700 anneals to the target DNA 238 (FIG. 85) and is then extended, forming a DNA strand containing both the probe sequence and the amplification product. The amplification blocker 694 prevents the polymerase from reading through and copying the probe region 696. Upon subsequent denaturation, the extended oligonucleotide primer 700/template hybrid is dissociated and so is the double stranded stem 242 of the primer-linked linear probe, thus releasing the quencher 248. Once the temperature decreases for the annealing and extension steps, the primer linked probe sequence 696 of the primer-linked linear probe curls around and hybridizes to the amplified complementary sequence 698 on the extended strand and fluorescence is detected indicating the presence of the target DNA. Non-extended primer-linked linear probes retain their double-stranded stem and fluorescence remains quenched. This detection method is particularly well suited for fast detection systems as it relies on a single-molecule process.

Primer-Linked Stem-and-Loop Probes

Figure 87:
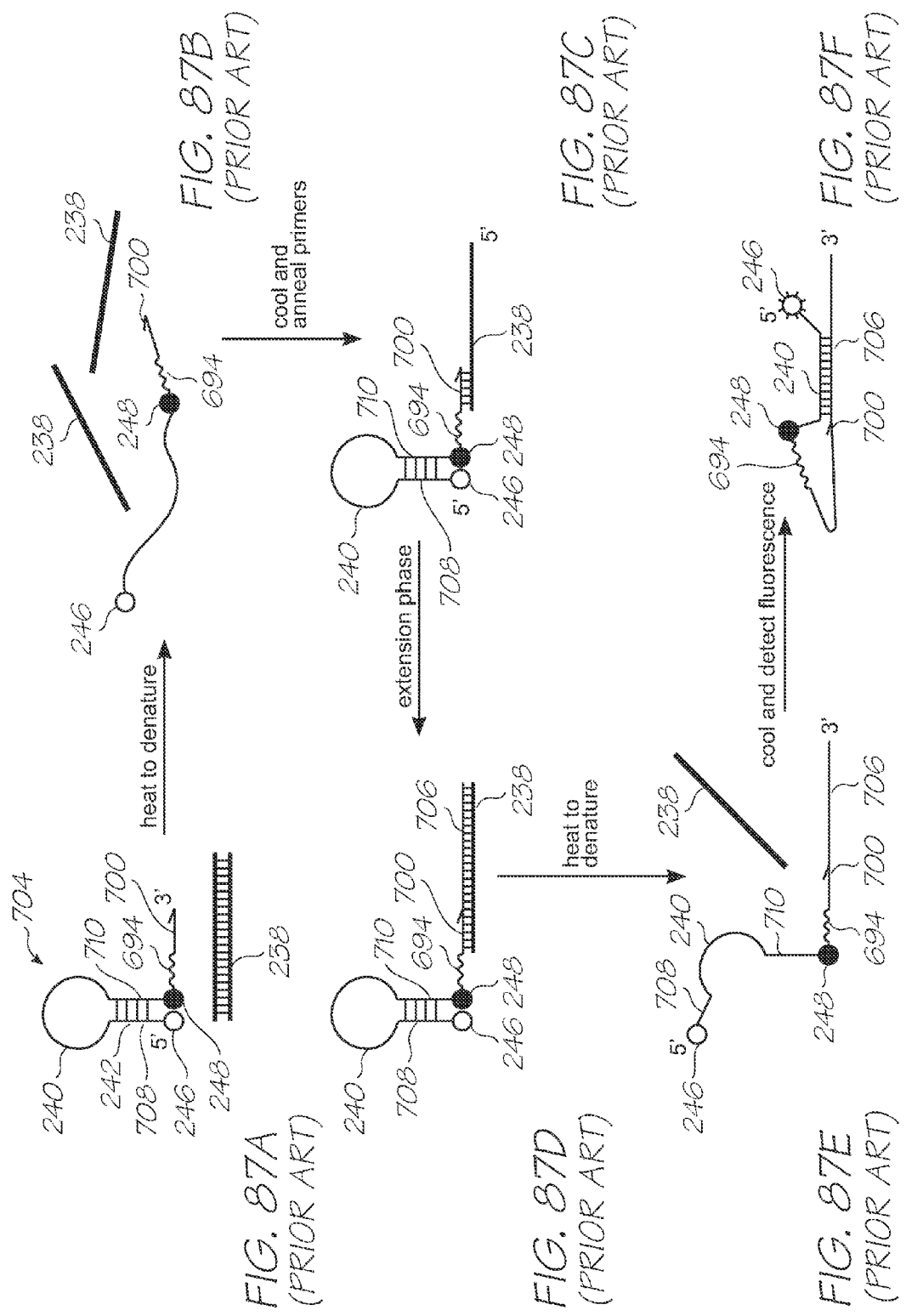
FIGS. 87A to 87F diagrammatically illustrate thermal cycling of a primer-linked fluorescent stem-and-loop probe.

FIGS. 87A to 87F show the operation of a primer-linked stem-and-loop probe 704. Referring to FIG. 87A, the primer-linked stem-and-loop probe 704 has a stem 242 of complementary double-stranded DNA and a loop 240 which incorporates the probe sequence. One of the stem strands 708 is labelled at its 5' end with fluorophore 246. The other strand 710 is labelled with a 3'-end quencher 248 and carries both the amplification blocker 694 and oligonucleotide primer 700. During the initial denaturation phase (see FIG. 87B), the strands of the target nucleic acid 238 separate, as does the stem 242 of the primer-linked, stem-and-loop probe 704. When the temperature cools for the annealing phase (see FIG. 87C), the oligonucleotide primer 700 on the primer-linked stem-and-loop probe 704 hybridizes to the target nucleic acid sequence 238. During extension (see FIG. 87D) the complement 706 to the target nucleic acid sequence 238 is synthesized forming a DNA strand containing both the probe sequence 704 and the amplified product. The amplification blocker 694 prevents the polymerase from reading through and copying the probe region 704. When the probe next anneals, following denaturation, the probe sequence of the loop segment 240 of the primer-linked stem-and-loop probe (see FIG. 87F) anneals to the complementary sequence 706 on the extended strand. This configuration leaves the fluorophore 246 relatively remote from the quencher 248, resulting in a significant increase in fluorescence emission.

Control Probes

Figure 99:
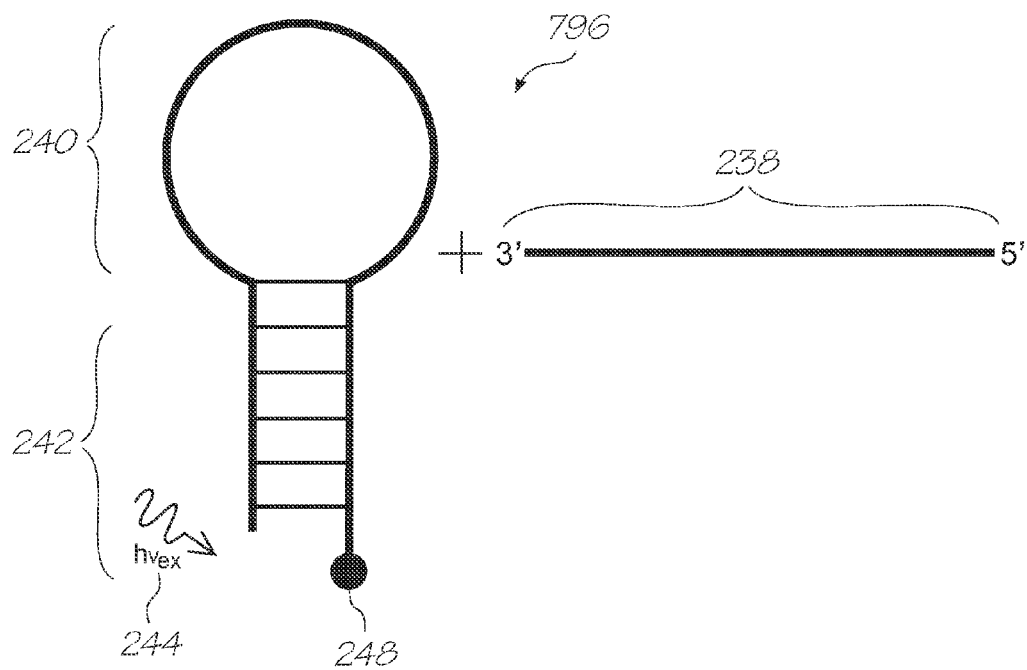
FIG. 99 schematically illustrates a negative control fluorescent probe in its stem-and-loop configuration.
Figure 100:
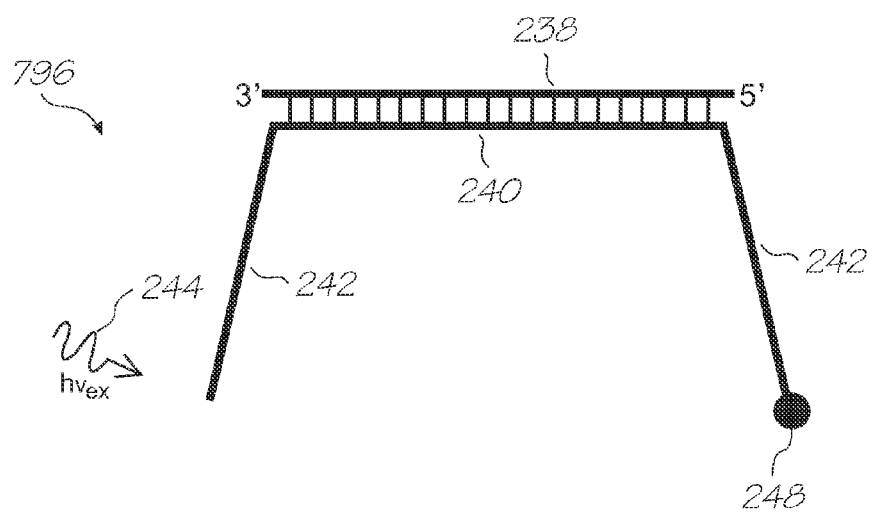
FIG. 100 schematically illustrates the negative control fluorescent probe of FIG. 99 in its open configuration.
Figure 101:
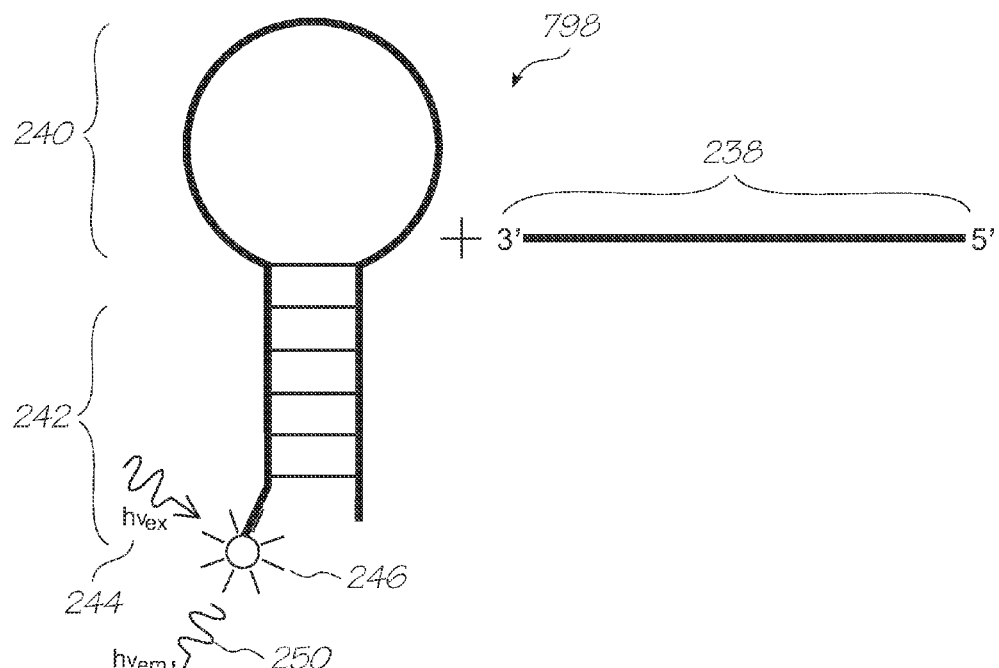
FIG. 101 schematically illustrates a positive control fluorescent probe in its stem-and-loop configuration.
Figure 102:
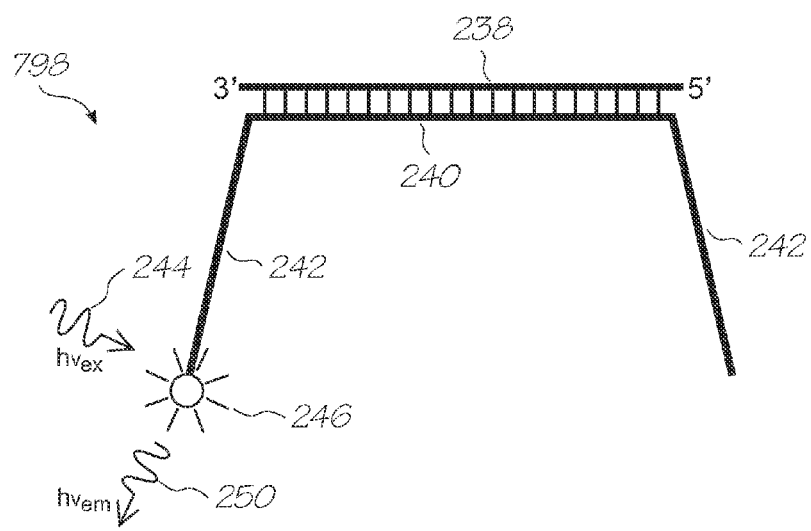
FIG. 102 schematically illustrates the positive control fluorescent probe of FIG. 101 in its open configuration.

The hybridization chamber array 110 includes some hybridization chambers 180 with positive and negative control probes used for assay quality control. FIGS. 99 and 100 schematically illustrate negative control probes without a fluorophore 796, and FIGS. 101 and 102 are sketches of positive control probes without a quencher 798. The positive and negative control probes have a stem-and-loop structure like the FRET probes described above. However, a fluorescence signal 250 will always be emitted from positive control probes 798 and no fluorescence signal 250 is ever emitted from negative control probes 796, regardless of whether the probes hybridize into an open configuration or remain closed.

Referring to FIGS. 99 and 100, the negative control probe 796 has no fluorophore (and may or may not have a quencher 248). Hence, whether the target nucleic acid sequence 238 hybridizes with the probe (see FIG. 100), or the probe remains in its stem-and-loop configuration (see FIG. 99), the response to the excitation light 244 is negligible. Alternatively, the negative control probe 796 could be designed so that it always remains quenched. For example, by synthesizing the loop 240 to have a probe sequence that will not hybridize to any nucleic acid sequence within the sample under investigation, the stem 242 of the probe molecule will re-hybridize to itself and the fluorophore and quencher will remain in close proximity and no appreciable fluorescence signal will be emitted. This negative control signal would correspond to low level emissions from hybridization chambers 180 in which the probes has not hybridized but the quencher does not quench all emissions from the reporter.

Conversely, the positive control probe 798 is constructed without a quencher as illustrated in FIGS. 101 and 102. Nothing quenches the fluorescence emission 250 from the fluorophore 246 in response to the excitation light 244 regardless of whether the positive control probe 798 hybridizes with the target nucleic acid sequence 238.

FIG. 52 shows a possible distribution of the positive and negative control probes (378 and 380 respectively) throughout the hybridization chamber array 110. The control probes 378 and 380 are placed in hybridization chambers 180 positioned in a line across the hybridization chamber array 110. However, the arrangement of the control probes within the array is arbitrary (as is the configuration of the hybridization chamber array 110).

Fluorophore Design

Fluorophores with long fluorescence lifetimes are required in order to allow enough time for the excitation light to decay to an intensity below that of the fluorescence emission at which time the photosensor 44 is enabled, thereby providing a sufficient signal to noise ratio. Also, longer fluorescence lifetime translates into larger integrated fluorescence photon count.

The fluorophores 246 (see FIG. 59) have a fluorescence lifetime greater than 100 nanoseconds, often greater than 200 nanoseconds, more commonly greater than 300 nanoseconds and in most cases greater than 400 nanoseconds.

The metal-ligand complexes based on the transition metals or lanthanides have long lifetimes (from hundreds of nanoseconds to milliseconds), adequate quantum yields, and high thermal, chemical and photochemical stability, which are all favourable properties with respect to the fluorescence detection system requirements.

A particularly well-studied metal-ligand complex based on the transition metal ion Ruthenium (Ru(II)) is tris(2,2'-bipyridine) ruthenium (II) ([Ru(bpy)$_3$]$^{2+}$) which has a lifetime of approximately 1 μs. This complex is available commercially from Biosearch Technologies under the brand name Pulsar 650.

TABLE 1

Photophysical properties of Pulsar 650 (Ruthenium chelate)

| Parameter | Symbol | Value | Unit |
|---|---|---|---|
| Absorption Wavelength | $\lambda_{abs}$ | 460 | nm |
| Emission Wavelength | $\lambda_{em}$ | 650 | nm |
| Extinction Coefficient | E | 14800 | M$^{-1}$cm$^{-1}$ |
| Fluorescence Lifetime | $\tau_f$ | 1.0 | μs |
| Quantum Yield | H | 1 (deoxygenated) | N/A |

Terbium chelate, a lanthanide metal-ligand complex has been successfully demonstrated as a fluorescent reporter in a FRET probe system, and also has a long lifetime of 1600 μs.

TABLE 2

Photophysical properties of terbium chelate

| Parameter | Symbol | Value | Unit |
|---|---|---|---|
| Absorption Wavelength | $\lambda_{abs}$ | 330-350 | nm |
| Emission Wavelength | $\lambda_{em}$ | 548 | nm |
| Extinction Coefficient | E | 13800 ($\lambda_{abs}$ and ligand dependent, can be up to 30000 @ $\lambda_{e-340nm}$) | M$^{-1}$cm$^{-1}$ |
| Fluorescence Lifetime | $\tau_f$ | 1600 (hybridized probe) | μs |
| Quantum Yield | H | 1 (ligand dependent) | N/A |

The fluorescence detection system used by the LOC device 301 does not utilize filters to remove unwanted background fluorescence. It is therefore advantageous if the quencher 248 has no native emission in order to increase the signal-to-noise ratio. With no native emission, there is no contribution to background fluorescence from the quencher 248. High quenching efficiency is also important so that fluorescence is prevented until a hybridization event occurs. The Black Hole Quenchers (BHQ), available from Biosearch Technologies, Inc. of Novato Calif., have no native emission and high quenching efficiency, and are suitable quenchers for the system. BHQ-1 has an absorption maximum at 534 nm, and a quenching range of 480-580 nm, making it a suitable quencher for the Tb-chelate fluorophore. BHQ-2 has an absorption maximum at 579 nm, and a quenching range of 560-670 nm, making it a suitable quencher for Pulsar 650.

Iowa Black Quenchers (Iowa Black FQ and RQ), available from Integrated DNA Technologies of Coralville, Iowa, are suitable alternative quenchers with little or no background emission. Iowa Black FQ has a quenching range from 420-620 nm, with an absorption maximum at 531 nm and would therefore be a suitable quencher for the Tb-chelate fluorophore. Iowa Black RQ has an absorption maximum at 656 nm, and a quenching range of 500-700 nm, making it an ideal quencher for Pulsar 650.

In the embodiments described here, the quencher 248 is a functional moiety which is initially attached to the probe, but other embodiments are possible in which the quencher is a separate molecule free in solution.

Excitation Source

Figure 88:
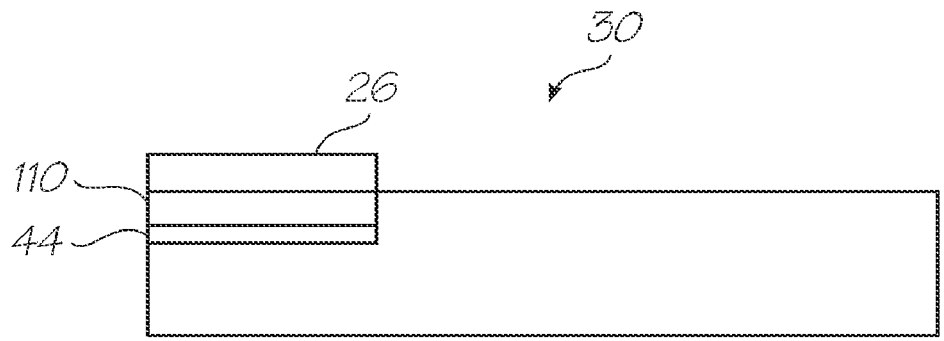
FIG. 88 is a schematic illustration of the excitation LED relative to the hybridization chamber array and the photodiodes.

In the fluorescence detection based embodiments described herein, a LED is chosen as the excitation source instead of a laser diode, high power lamp or laser due to the low power consumption, low cost and small size. Referring to FIG. 88, the LED 26 is positioned directly above the hybridization chamber array 110 on an external surface of the LOC device 301. On the opposing side of the hybridization chamber array 110, is the photosensor 44, made up of an array of photodiodes 184 (see FIGS. 53, 54 and 69) for detection of fluorescence signals from each of the chambers.

Figure 89:
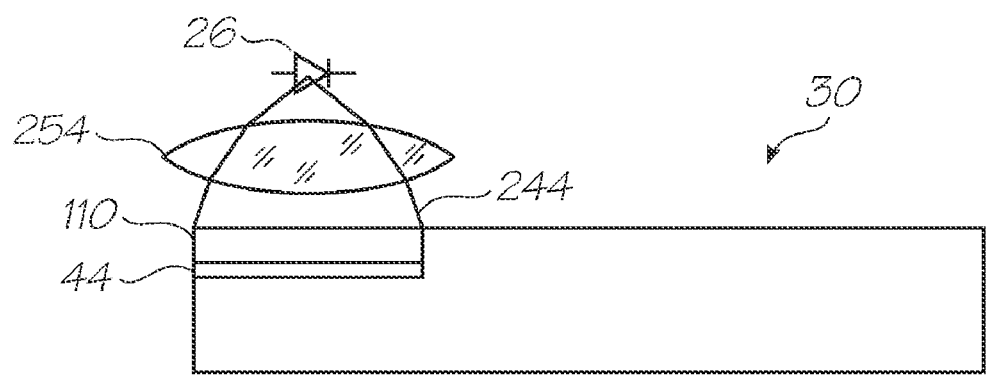
FIG. 89 is a schematic illustration of the excitation LED and optical lens for directing light onto the hybridization chamber array of the LOC device.
Figure 90:
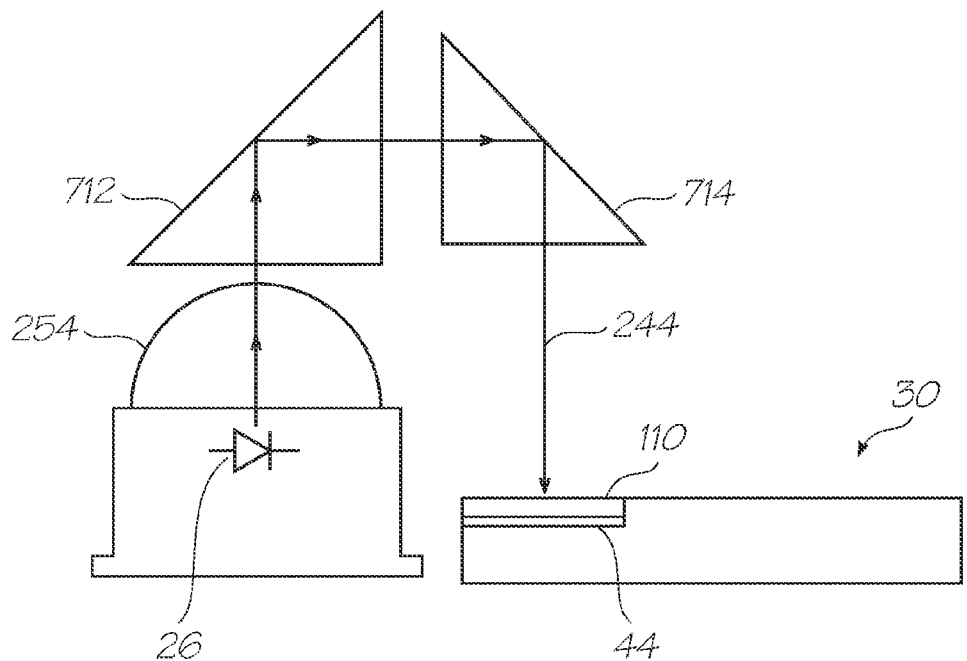
FIG. 90 is a schematic illustration of the excitation LED, optical lens, and optical prisms for directing light onto the hybridization chamber array of the LOC device.
Figure 91:
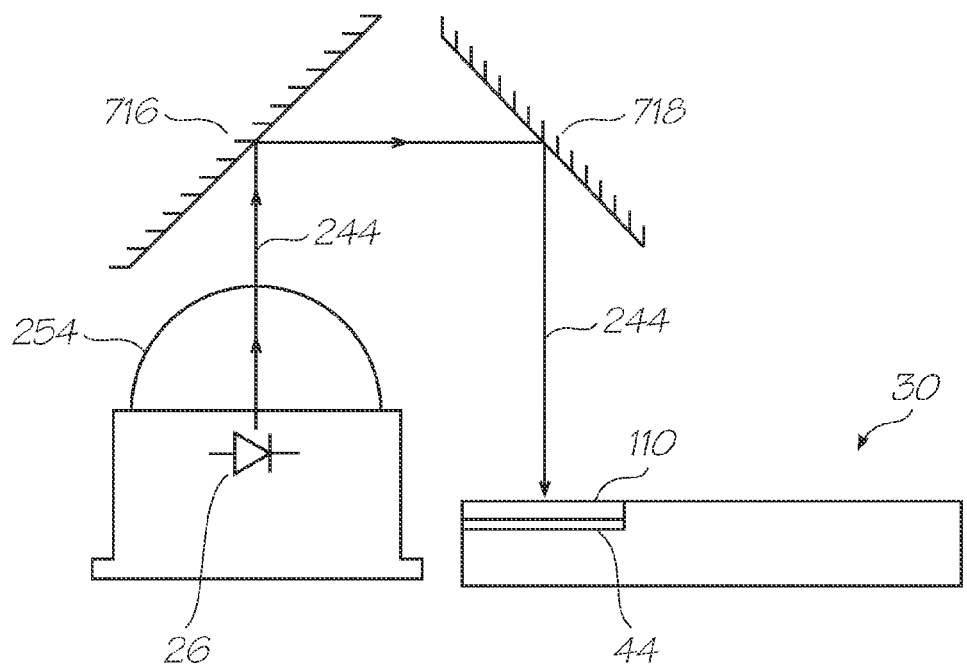
FIG. 91 is a schematic illustration of the excitation LED, optical lens and mirror arrangement for directing light onto the hybridization chamber array of the LOC device.

FIGS. 89, 90 and 91 schematically illustrate other embodiments for exposing the probes to excitation light. In the LOC device 30 shown in FIG. 89, the excitation light 244 generated by the excitation LED 26 is directed onto the hybridization chamber array 110 by the lens 254. The excitation LED 26 is pulsed and the fluorescence emissions are detected by the photosensor 44.

In the LOC device 30 shown in FIG. 90, the excitation light 244 generated by the excitation LED 26 is directed onto the hybridization chamber array 110 by the lens 254, a first optical prism 712 and second optical prism 714. The excitation LED 26 is pulsed and the fluorescence emissions are detected by the photosensor 44.

Similarly, the LOC device 30 shown in FIG. 91, the excitation light 244 generated by the excitation LED 26 is directed onto the hybridization chamber array 110 by the lens 254, a first mirror 716 and second mirror 718. Again, the excitation LED 26 is pulsed and the fluorescence emissions are detected by the photosensor 44.

The excitation wavelength of the LED 26 is dependent on the choice of fluorescent dye. The Philips LXK2-PR14-R00 is a suitable excitation source for the Pulsar 650 dye. The SET UVTOP335TO39BL LED is a suitable excitation source for the Tb-chelate label.

TABLE 3

Philips LXK2-PR14-R00 LED specifications

| Parameter | Symbol | Value | Unit |
|---|---|---|---|
| Wavelength | $\lambda_{ex}$ | 460 | nm |
| Emission Frequency | $v_{em}$ | $6.52(10)^{14}$ | Hz |
| Output Power | $p_I$ | 0.515 (min) @ 1 A | W |
| Radiation pattern | | Lambertian profile | N/A |

TABLE 4

SET UVTOP334TO39BL LED Specifications

| Parameter | Symbol | Value | Unit |
|---|---|---|---|
| Wavelength | $\lambda_e$ | 340 | nm |
| Emission Frequency | $v_e$ | $8.82(10)^{14}$ | Hz |
| Power | $p_I$ | 0.000240 (min) @ 20 mA | W |
| Pulse Forward Current | I | 200 | mA |
| Radiation pattern | | Lambertian | N/A |

Ultra Violet Excitation Light

Silicon absorbs little light in the UV spectrum. Accordingly, it is advantageous to use UV excitation light. A UV LED excitation source can be used but the broad spectrum of the LED 26 reduces the effectiveness of this method. To address this, a filtered UV LED can be used. Optionally, a UV laser can be the excitation source unless the relatively high cost of the laser is impractical for the particular test module market.
LED Driver The LED driver 29 drives the LED 26 at a constant current for the required duration. A lower power USB 2.0-certifiable device can draw at most 1 unit load (100 mA), with a minimum operating voltage of 4.4 V. A standard power conditioning circuit is used for this purpose.
Photodiode FIG. 54 shows the photodiode 184 integrated into the CMOS circuitry 86 of the LOC device 301. The photodiode 184 is fabricated as part of the CMOS circuitry 86 without additional masks or steps. This is one significant advantage of a CMOS photodiode over a CCD, an alternate sensing technology which could be integrated on the same chip using non-standard processing steps, or fabricated on an adjacent chip. On-chip detection is low cost and reduces the size of the assay system. The shorter optical path length reduces noise from the surrounding environment for efficient collection of the fluorescence signal and eliminates the need for a conventional optical assembly of lenses and filters.

Quantum efficiency of the photodiode 184 is the fraction of photons impinging on its active area 185 that are effectively converted to photo-electrons. For standard silicon processes, the quantum efficiency is in the range of 0.3 to 0.5 for visible light, depending on process parameters such as the amount and absorption properties of the cover layers.

The detection threshold of the photodiode 184 determines the smallest intensity of the fluorescence signal that can be detected. The detection threshold also determines the size of the photodiode 184 and hence the number of hybridization chambers 180 in the hybridization and detection section 52 (see FIG. 52). The size and number of chambers are technical parameters that are limited by the dimensions of the LOC device (in the case of the LOC device 301, the dimensions are 1760 µm×5824 µm) and the real estate available after other functional modules such as the pathogen dialysis section 70 and amplification section(s) 112 are incorporated.

For standard silicon processes, the photodiode 184 detects a minimum of 5 photons. However, to ensure reliable detection, the minimum can be set to 10 photons. Therefore with the quantum efficiency range being 0.3 to 0.5 (as discussed above), the fluorescence emission from the probes should be a minimum of 17 photons but 30 photons would incorporate a suitable margin of error for reliable detection.
Calibration Chambers The non-uniformity of the electrical characteristic of the photodiode 184, autofluorescence, and residual excitation photon flux that has not yet completely decayed, introduce background noise and offset into the output signal. This background is removed from each output signal using one or more calibration signals. Calibration signals are generated by exposing one or more calibration photodiodes 184 in the array to respective calibration sources. A low calibration source is used for determining a negative result in which a target has not reacted with a probe. A high calibration source is indicative of a positive result from a probe-target complex. In the embodiment described here, the low calibration light source is provided by calibration chambers 382 in the hybridization chamber array 110 which:

do not contain any probes;

contain probes that have no fluorescent reporter; or, contain probes with a reporter and quencher configured such that quenching is always expected to occur.

The output signal from such calibration chambers 382 closely approximates the noise and offset in the output signal from all the hybridization chambers in the LOC device. Subtracting the calibration signal from the output signals generated by the other hybridization chambers substantially removes the background and leaves the signal generated by the fluorescence emission (if any). Signals arising from ambient light in the region of the chamber array are also subtracted.

Figure 92:
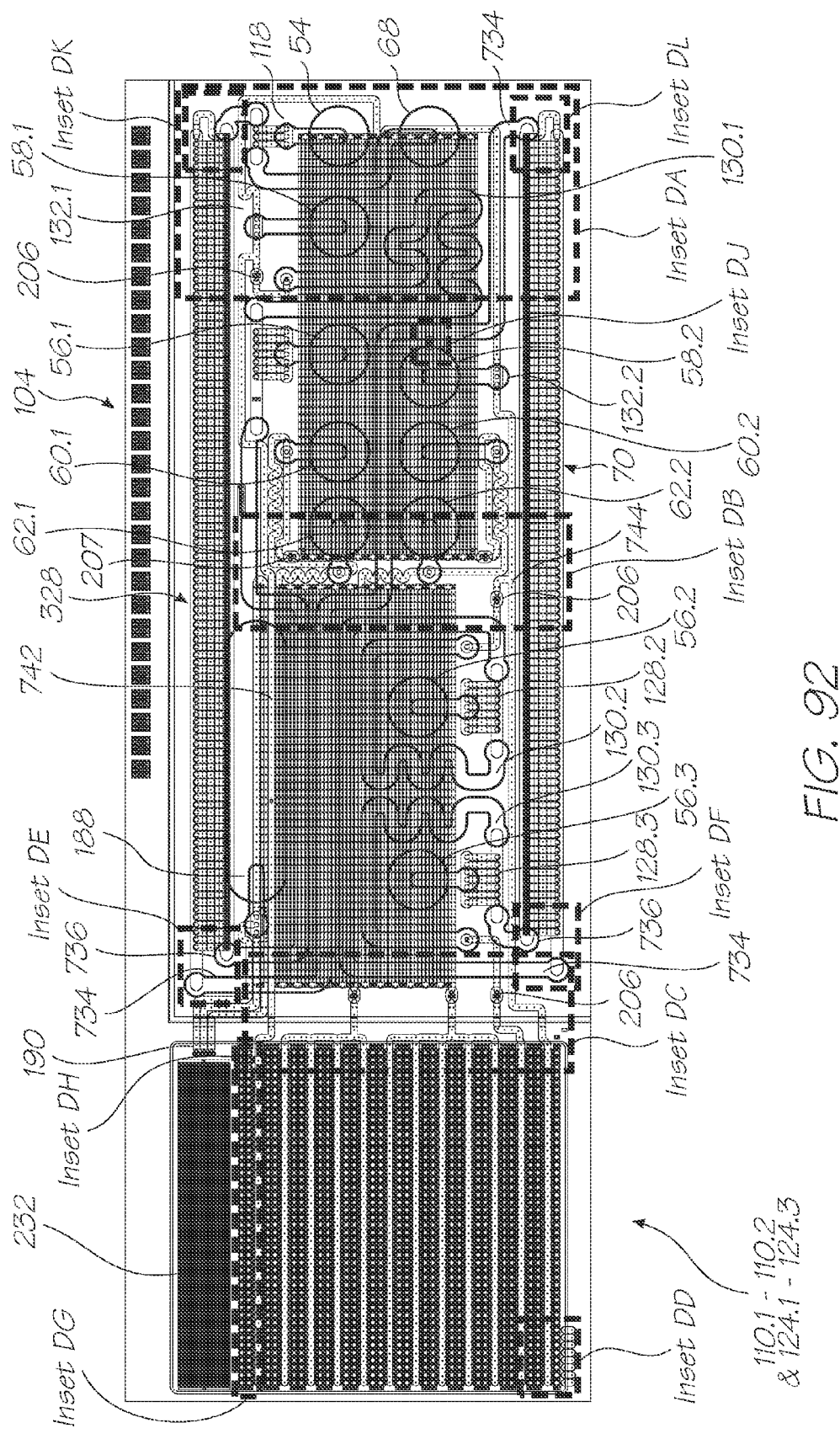
FIG. 92 is a plan view showing all the features superimposed on each other, and showing the location of Insets DA to DK.

It will be appreciated that the negative control probes described above with reference to FIGS. 99 to 102 can be used in calibration chambers. However, as shown in FIGS. 93 and 94, which are enlarged views of insets DG and DH of LOC variant X 728 shown in FIG. 92, another option is to fluidically isolate the calibration chambers 382 from the amplicon. The background noise and offset can be determined by leaving the fluidically isolated chambers empty, or containing reporterless probes, or indeed any of the 'normal' probes with both reporter and quencher as hybridization is precluded by fluidic isolation.

The calibration chambers 382 can provide a high calibration source to generate a high signal in the corresponding photodiodes. The high signal corresponds to all probes in a chamber having hybridized. Spotting probes with reporters and no quenchers, or just reporters will consistently provide a signal approximating that of a hybridization chamber in which a predominant number of the probes have hybridized.

It will also be appreciated that calibration chambers 382 can be used instead of control probes, or in addition to control probes.

The number and arrangement of the calibration chambers 382 throughout the hybridization chamber array is arbitrary. However, the calibration is more accurate if photodiodes 184 are calibrated by a calibration chamber 382 that is relatively proximate. Referring to FIG. 56, the hybridization chamber array 110 has one calibration chamber 382 for every eight hybridization chambers 180. That is, a calibration chamber 382 is positioned in the middle of every three by three square of hybridization chambers 180. In this configuration, the hybridization chambers 180 are calibrated by a calibration chamber 382 that is immediately adjacent.

Figure 98:
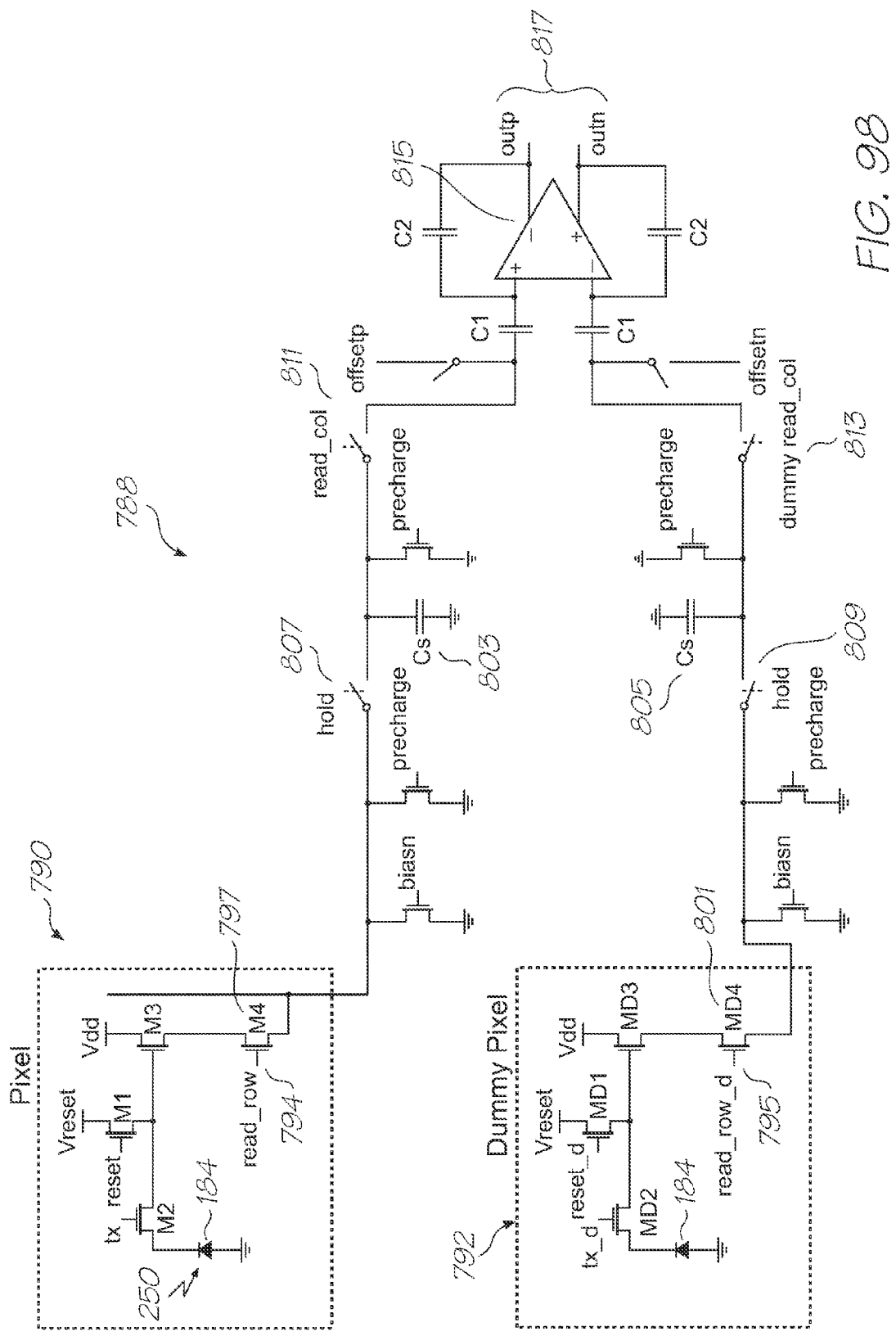
FIG. 98 is a circuit diagram of the differential imager.

FIG. 98 shows a differential imager circuit 788 used to substract the signal from the photodiode 184 corresponding to the calibration chamber 382 as a result of excitation light, from the fluorescence signal from the surrounding hybridization chambers 180. The differential imager circuit 788 samples the signal from the pixel 790 and a "dummy" pixel 792. In one embodiment, the "dummy" pixel 792 is shielded from light, so its output signal provides a dark reference. Alternatively, the "dummy" pixel 792 can be exposed to the excitation light along with the rest of the array. In the embodiment where the "dummy" pixel 792 is open to light, signals arising from ambient light in the region of the chamber array are also subtracted. The signals from the pixel 790 are small (i.e. close to dark signal), and without a reference to a dark level it is hard to differentiate between the background and a very small signal.

During use, the "read_row" 794 and "read_row_d" 795 are activated and M4 797 and MD4 801 transistors are turned on. Switches 807 and 809 are closed such that the outputs from the pixel 790 and "dummy" pixel 792 are stored on pixel capacitor 803 and dummy pixel capacitor 805 respectively. After the pixel signals have been stored, switches 807 and 809 are deactivated. Then the "read_col" switch 811 and dummy "read_col" switch 813 are closed, and the switched capacitor amplifier 815 at the output amplifies the differential signal 817.

Suppression and Enablement of the Photodiode

Figure 72:
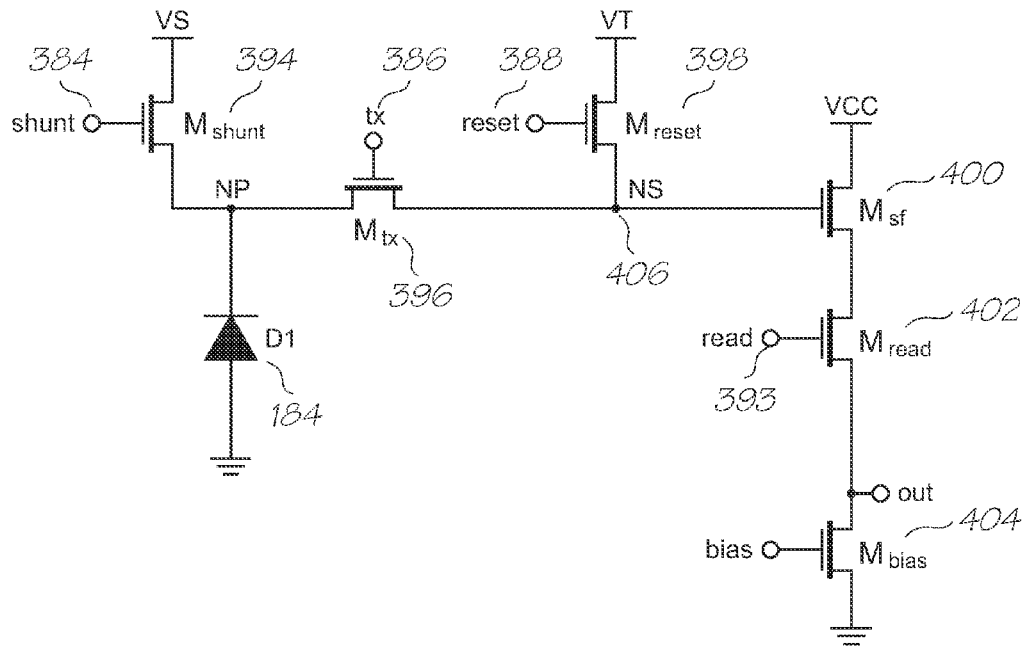
FIG. 72 is a circuit diagram for a single photodiode.
Figure 73:
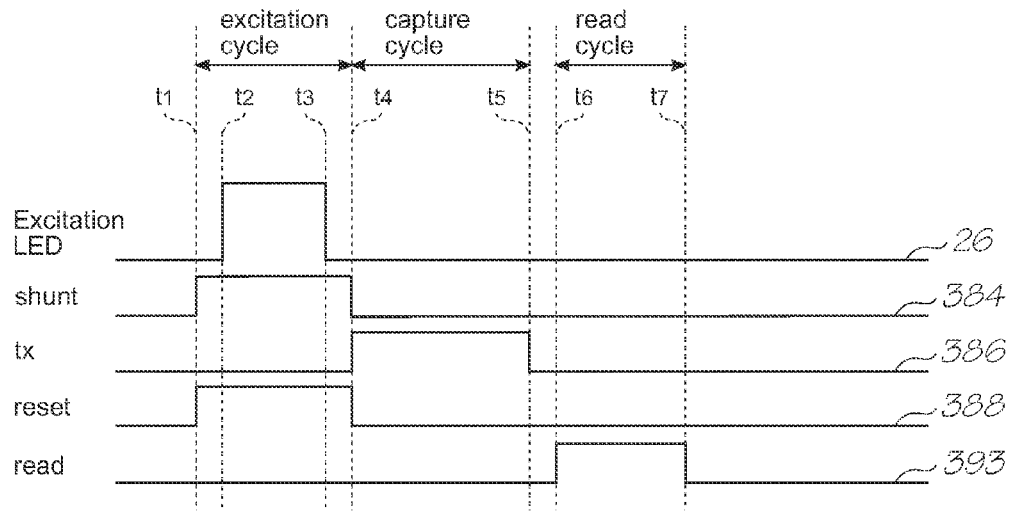
FIG. 73 is a timing diagram for the photodiode control signals.

The photodiode 184 needs to be suppressed during excitation by the LED 26 and enabled during fluorescence. FIG. 72 is a circuit diagram for a single photodiode 184 and FIG. 73 is a timing diagram for the photodiode control signals. The circuit has photodiode 184 and six MOS transistors, $M_{shunt}$ 394, $M_{tx}$ 396, $M_{reset}$ 398, $M_{sf}$ 400, $M_{read}$ 402 and $M_{bias}$ 404. At the beginning of the excitation cycle, t1, the transistors $M_{shunt}$ 394, and $M_{reset}$ 398 are turned on by pulling the $M_{shunt}$ gate 384 and the reset gate 388 high. During this period, the excitation photons generate carriers in the photodiode 184. These carriers have to be removed, as the amount of generated carriers can be sufficient to saturate the photodiode 184. During this cycle, $M_{shunt}$ 394 directly removes the carriers generated in photodiode 184, while $M_{reset}$ 398 resets any carriers that have accumulated on node 'NS' 406 due to leakage in transistors or due to diffusion of excitation-produced carriers in the substrate. After excitation, a capture cycle commences at t4. During this cycle, the emitted response from the fluorophore is captured and integrated in the circuit on node 'NS' 406. This is achieved by pulling tx gate 386 high, which turns on the transistor $M_{tx}$ 396 and transfers any accumulated carriers on the photodiode 184 to node 'NS' 406. The duration of the capture cycle can be as long as the fluorophore emits. The outputs from all photodiodes 184 in the hybridization chamber array 110 are captured simultaneously.

There is a delay between the end of the capture cycle t5 and the start of the read cycle t6. This delay is due to the requirement to read each photodiode 184 in the hybridization chamber array 110 (see FIG. 52) separately following the capture cycle. The first photodiode 184 to be read will have the shortest delay before the read cycle, while the last photodiode 184 will have the longest delay before the read cycle. During the read cycle, transistor $M_{read}$ 402 is turned on by pulling the read gate 393 high. The 'NS' node 406 voltage is buffered and read out using the source-follower transistor $M_{sf}$ 400.

There are additional, optional methods of enabling or suppressing the photodiode as discussed below:

1. Suppression Methods

Figure 95:
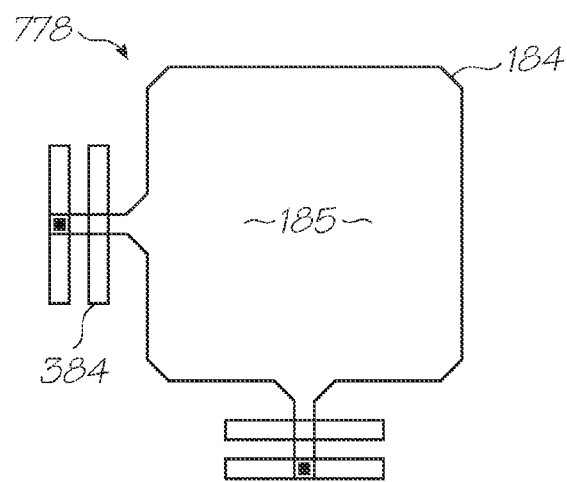
FIG. 95 shows one embodiment of the shunt transistor for the photodiodes.
Figure 96:
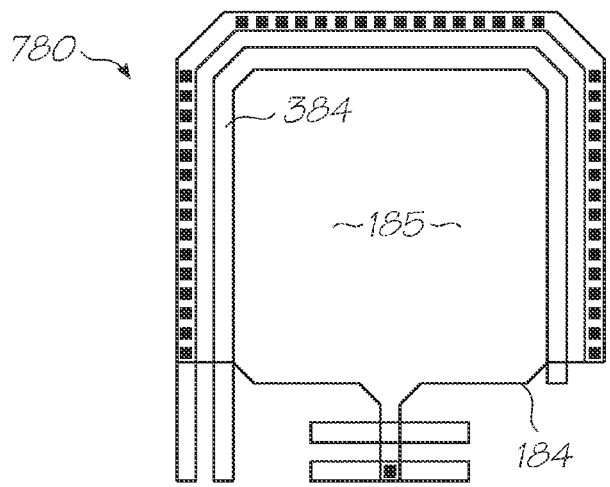
FIG. 96 shows one embodiment of the shunt transistor for the photodiodes.
Figure 97:
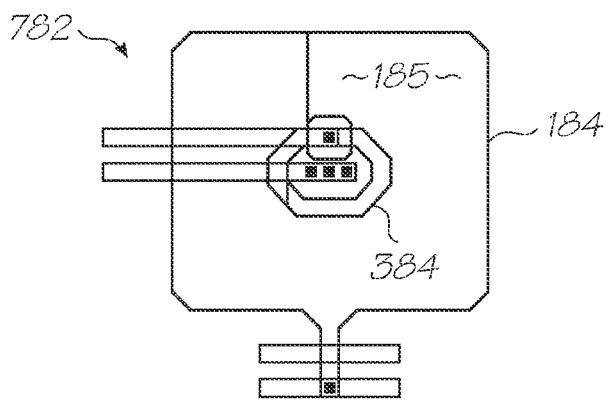
FIG. 97 shows one embodiment of the shunt transistor for the photodiodes.

FIGS. 95, 96 and 97 show three possible configurations 778, 780, 782 for the $M_{shunt}$ transistor 394. The $M_{shunt}$ transistor 394 has a very high off ratio at maximum $|V_{Gs}|=5$ V which is enabled during excitation. As shown in FIG. 95, the $M_{shunt}$ gate 384 is configured to be on the edge of the photodiode 184. Optionally, as shown in FIG. 96, the $M_{shunt}$ gate 384 may be configured to surround the photodiode 184. A third option is to configure the $M_{shunt}$ gate 384 inside the photodiode 184, as shown in FIG. 97. Under this third option there would be less photodiode active area 185.

These three configurations 778, 780 and 782 reduce the average path length from all locations in the photodiode 184 to the $M_{shunt}$ gate 384. In FIG. 95, the $M_{shunt}$ gate 384 is on one side of the photodiode 184. This configuration is simplest to fabricate and impinges the least on the photodiode active area 185. However, any carriers lingering on the remote side of the photodiode 184 would take longer to propagate through to the $M_{shunt}$ gate 384.

In FIG. 96, the $M_{shunt}$ gate 384 surrounds the photodiode 184. This further reduces the average path length for carriers in the photodiode 184 to the $M_{shunt}$ gate 384. However, extending the $M_{shunt}$ gate 384 about the periphery of the photodiode 184 imposes a greater reduction of the photodiode active area 185. The configuration 782 in FIG. 97 positions the $M_{shunt}$ gate 384 within the active area 185. This provides the shortest average path length to the $M_{shunt}$ gate 384 and hence the shortest transition time. However, the impingement on the active area 185 is greatest. It also poses a wider leakage path.

2. Enabling Methods a. A trigger photodiode drives the shunt transistor with a fixed delay.

b. A trigger photodiode drives the shunt transistor with programmable delay.

c. The shunt transistor is driven from the LED drive pulse with a fixed delay.

d. The shunt transistor is driven as in 2c but with programmable delay.

Figure 75:
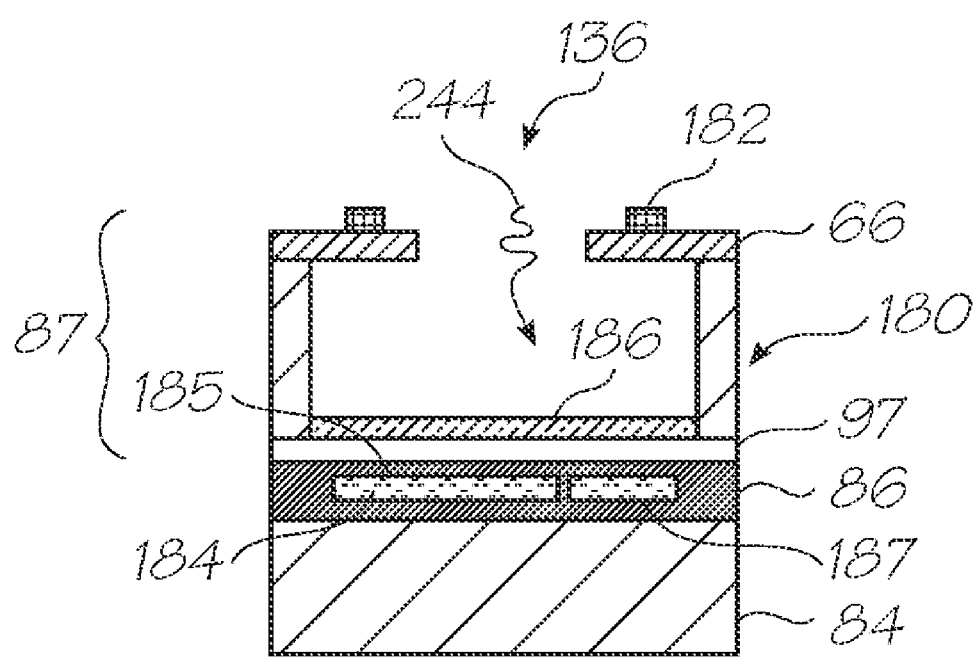
FIG. 75 is a schematic section view through a hybridization chamber with a detection photodiode and trigger photodiode.

FIG. 75 is a schematic section view through a hybridization chamber 180 showing a photodiode 184 and trigger photodiode 187 embedded in the CMOS circuitry 86. A small area in the corner of the photodiode 184 is replaced with the trigger photodiode 187. A trigger photodiode 187 with a small area is sufficient as the intensity of the excitation light will be high in comparison with the fluorescence emission. The trigger photodiode 187 is sensitive to the excitation light 244. The trigger photodiode 187 registers that the excitation light 244 has extinguished and activates the photodiode 184 after a short time delay Δt 300 (see FIG. 2). This delay allows the fluorescence photodiode 184 to detect the fluorescence emission from the FRET probes 186 in the absence of the excitation light 244. This enables detection and improves the signal to noise ratio.

Both photodiodes 184 and trigger photodiodes 187 are located in the CMOS circuitry 86 under each hybridization chamber 180. The array of photodiodes combines, along with appropriate electronics, to form the photosensor 44 (see FIG. 69). The photodiodes 184 are pn-junction fabricated during CMOS structure manufacturing without additional masks or steps. During MST fabrication, the dielectric layer (not shown) above the photodiodes 184 is optionally thinned using the standard MST photolithography techniques to allow more fluorescent light to illuminate the active area 185 of the photodiode 184. The photodiode 184 has a field of view such that the fluorescence signal from the probe-target hybrids within the hybridization chamber 180 is incident on the sensor face. The fluorescent light is converted into a photocurrent which can then be measured using CMOS circuitry 86.

Alternatively, one or more hybridization chambers 180 can be dedicated to a trigger photodiode 187 only. These options can be used in these in combination with 2a and 2b above.

Delayed Detection of Fluorescence

Figure 60:
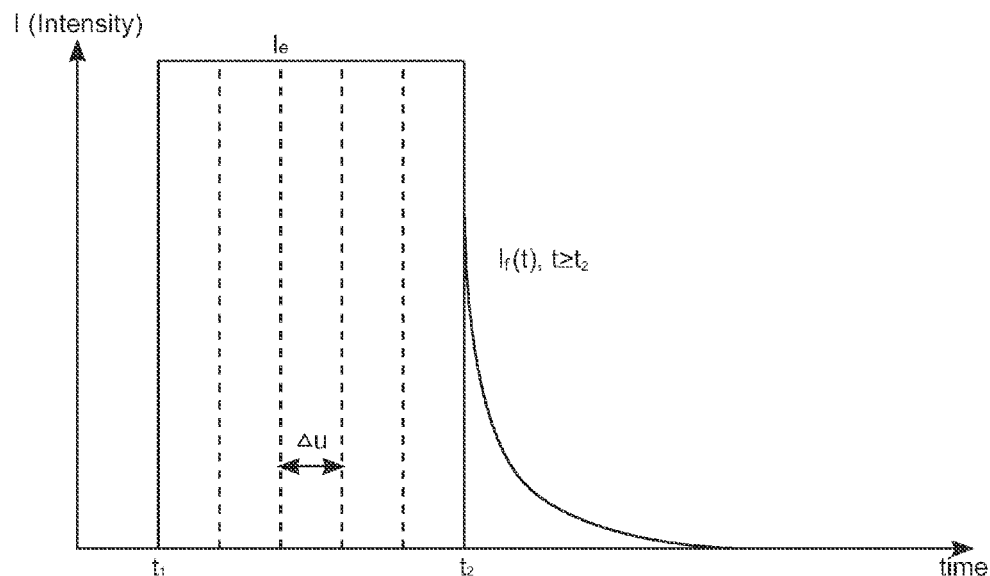
FIG. 60 is a graph of the intensity of an excitation light over time.

The following derivations elucidate the delayed detection of fluorescence using a long-lifetime fluorophore for the LED/fluorophore combinations described above. The fluorescence intensity is derived as a function of time after excitation by an ideal pulse of constant intensity $I_e$ between time $t_1$ and $t_2$ as shown in FIG. 60.

Let [S1](t) equal the density of excited states at time t, then during and after excitation, the number of excited states per unit time per unit volume is described by the following differential equation:

$$\frac{d[S1]}{dt}(t) + \frac{[S1](t)}{\tau_F} = \frac{I_e \varepsilon c}{h v_e} \quad (1)$$

where c is the molar concentration of fluorophores, $\varepsilon$ is the molar extinction coefficient, $v_e$ is the excitation frequency, and $h = 6.62606896(10)^{-34}$ Js is the Planck constant.

This differential equation has the general form:

$$\frac{dy}{dx} + p(x)y = q(x)$$

which has the solution:

$$y(x) = \frac{\int e^{\int p(x)dx} q(x) dx + k}{e^{\int p(x)dx}} \quad (2)$$

Using this now to solve equation (1), $$[S1](t) = \frac{I_e \varepsilon c \tau_f}{h v_e} + k e^{-t/\tau_f} \quad (3)$$

Now at time $t_1$, $[S1](t_1)=0$, and from (3):

$$k = -\frac{I_e \varepsilon c \tau_f}{h v_e} e^{t_1/\tau_f} \quad (4)$$

Substituting (4) into (3):

$$[S1](t) = \frac{I_e \varepsilon c \tau_f}{h v_e} - \frac{I_e \varepsilon c \tau_f}{h v_e} e^{-(t-t_1)/\tau_f}$$

At time $t_2$:

$$[S1](t_2) = \frac{I_e \varepsilon c \tau_f}{h v_e} - \frac{I_e \varepsilon c \tau_f}{h v_e} e^{-(t_2-t_1)/\tau_f} \quad (5)$$

For $t \geq t_2$, the excited states decay exponentially and this is described by:

$$[S1](t) = [S1](t_2) e^{-(t-t_2)/\tau_f} \quad (6)$$

Substituting (5) into (6):

$$[S1](t) = \frac{I_e \varepsilon c \tau_f}{h v_e} \left[1 - e^{-(t_2-t_1)/\tau_f}\right] e^{-(t-t_2)/\tau_f} \quad (7)$$

The fluorescence intensity is given by the following equation:

$$I_f(t) = -\frac{d[S1](t)}{dx} h v_f \eta l \quad (8)$$

where $v_f$ is the fluorescence frequency, $\eta$ is the quantum yield and l is the optical path length.

Now from (7):

$$\frac{d[S1](t)}{dt} = -\frac{I_e \varepsilon c}{h v_e} \left[1 - e^{-(t_2-t_1)/\tau_f}\right] e^{-(t-t_2)/\tau_f} \quad (9)$$

Substituting (9) into (8):

$$I_f(t) = I_e \varepsilon c l \eta \frac{v_f}{v_e} \left[1 - e^{-(t_2-t_1)/\tau_f}\right] e^{-(t-t_2)/\tau_f} \quad (10)$$

$$\text{For } \frac{t_2 - t_1}{\tau_f} \to \infty, \quad I_f(t) \to I_e \varepsilon c l \eta \frac{v_f}{v_e} e^{-(t-t_2)/\tau_f}$$

Therefore, we can write the following approximate equation which describes the fluorescence intensity decay after a sufficiently long excitation pulse ($t_2 - t_1 \gg \tau_f$):

$$I_f(t) = I_e \varepsilon c l \eta \frac{v_f}{v_e} e^{-(t-t_2)/\tau_f} \quad \text{for } t \geq t_2 \quad (11)$$

In the previous section, we concluded that for $t_2 - t_1 \gg \tau_f$, $$I_f(t) = I_e \varepsilon c l \eta \frac{v_f}{v_e} e^{-(t-t_2)/\tau_f} \quad \text{for } t \geq t_2.$$

From the above equation, we can derive the following:

$$\dot{n}_f(t) = \dot{n}_e \varepsilon c l \eta e^{-(t-t_2)/\tau_f} \quad (12)$$

where $$\ddot{n}_f(t) = \frac{I_f(t)}{h\nu_f}$$

is the number of fluorescent photons per unit time per unit area and $$\ddot{n}_e = \frac{I_e}{h\nu_e}$$

is the number of excitation photons per unit time per unit area. Consequently, $$\ddot{n}_f(t) = \int_{t_3}^{\infty} \ddot{n}_f(t)dt \tag{13}$$

where $\ddot{n}_f$ is the number of fluorescent photons per unit area and $t_3$ is the instant of time at which the photodiode is turned on. Substituting (12) into (13):

$$\ddot{n}_f = \int_{t_3}^{\infty} \ddot{n}_e \varepsilon cl\eta e^{-(t-t_2)/\tau_f} dt \tag{14}$$

Now, the number of fluorescent photons that reach the photodiode per unit time per unit area, $\ddot{n}_s(t)$, is given by the following:

$$\ddot{n}_s(t) = \ddot{n}_f(t)\phi_0 \tag{15}$$

where $\phi_0$ is the light gathering efficiency of the optical system.

Substituting (12) into (15) we find $$\ddot{n}_s(t) = \phi_0 \ddot{n}_e \varepsilon cl\eta e^{-(t-t_2)/\tau_f} \tag{16}$$

Similarly, the number of fluorescence photons that reach the photodiode per unit fluorescent area $\ddot{n}_s$, will be as follows:

$$\ddot{n}_s = \int_{t_3}^{\infty} \ddot{n}_s(t)dt$$

and substituting in (16) and integrating:

$$\ddot{n}_s = \phi_0 \ddot{n}_e \varepsilon cl\eta \tau_f e^{-(t_3-t_2)/\tau_f}$$

Therefore, $$n_s = \phi_0 \ddot{n}_e \varepsilon cl\eta \tau_f e^{-\Delta t/\tau_f} \tag{17}$$

The optimal value of $t_3$ is when the rate of electrons generated in the photodiode 184 due to fluorescence photons becomes equal to the rate of electrons generated in the photodiode 184 by the excitation photons, as the flux of the excitation photons decays much faster than that of the fluorescence photons.

The rate of sensor output electrons per unit fluorescent area due to fluorescence is:

$$\ddot{e}_f(t) = \phi_f \ddot{n}_s(t)$$

where $\phi_f$ is the quantum efficiency of the sensor at the fluorescence wavelength.

Substituting in (17) we have:

$$\ddot{e}_f(t) = \phi_f \phi_0 \ddot{n}_e \varepsilon cl\eta e^{-(t-t_2)/\tau_f} \tag{18}$$

Similarly, the rate of sensor output electrons per unit fluorescent area due to the excitation photons is:

$$\ddot{e}_e(t) = \phi_e \ddot{n}_e e^{-(t-t_2)/\tau_e} \tag{19}$$

where $\phi_e$ is the quantum efficiency of the sensor at the excitation wavelength, and $\tau_e$ is the time-constant corresponding to the "off" characteristics of the excitation LED. After time $t_2$, the LED's decaying photon flux would increase the intensity of the fluorescence signal and extend its decay time, but we are assuming that this has a negligible effect on $I_f(t)$, thus we are taking a conservative approach.

Now, as mentioned earlier, the optimal value of $t_3$ is when:

$$\ddot{e}_f(t_3) = \ddot{e}_e(t_3)$$

Therefore, from (18) and (19) we have:

$$\phi_f \phi_0 \ddot{n}_e \varepsilon cl\eta e^{-(t_3-t_2)/\tau_f} = \phi_e \ddot{n}_e e^{-(t_3-t_2)/\tau_e}$$

and rearranging we find:

$$t_3 - t_2 = \frac{\ln\left(\varepsilon cl\eta \frac{\phi_f \phi_0}{\phi_e}\right)}{\frac{1}{\tau_f} - \frac{1}{\tau_e}} \tag{20}$$

From the previous two sections, we have the following two working equations:

$$n_s = \phi_0 \ddot{n}_e F \tau_f e^{-\Delta t/\tau_f} \tag{21}$$

$$\Delta t = \frac{\ln\left(F \frac{\phi_f \phi_0}{\phi_e}\right)}{\frac{1}{\tau_f} - \frac{1}{\tau_e}} \tag{22}$$

where $F = \varepsilon cl\eta$ and $\Delta t = t_3 - t_2$. We also know that, in practice, $t_2 - t_1 \gg \tau_f$.

The optimal time for fluorescence detection and the number of fluorescence photons detected using the Philips LXK2-PR14-R00 LED and Pulsar 650 dye are determined as follows. The optimum detection time is determined using equation (22):

Recalling the concentration of amplicon, and assuming that all amplicons hybridize, then the concentration of fluorescent fluorophores is: $c=2.89(10)^{-6}$ mol/L The height of the chamber is the optical path length $l=8(10)^{-6}$ m.

We have taken the fluorescence area to be equal to our photodiode area, yet our actual fluorescence area is substantially larger than our photodiode area; consequently we can approximately assume $\phi_0=0.5$ for the light gathering efficiency of our optical system. From the photodiode characteristics, $$\frac{\phi_f}{\phi_e} = 10$$

is a very conservative value for the ratio of the photodiode quantum efficiency at the fluorescence wavelength to its quantum efficiency at the excitation wavelength.

With a typical LED decay lifetime of $\tau_e=0.5$ ns and using Pulsar 650 specifications, $\Delta t$ can be determined:

$$F = [1.48(10)^6][2.89(10)^{-6}][8(10)^{-6}] \quad (1)$$
$$= 3.42(10)^{-5}$$

$$\Delta t = \frac{\ln([3.42(10)^{-5}](10)(0.5))}{\frac{1}{1(10)^{-6}} - \frac{1}{0.5(10)^{-9}}}$$
$$= 4.34(10)^{-9} s$$

The number of photons detected is determined using equation (21). First, the number of excitation photons emitted per unit time $\dot{n}_e$ is determined by examining the illumination geometry.

The Philips LXK2-PR14-R00 LED has a Lambertian radiation pattern, therefore:

$$\ddot{n}_l = \ddot{n}_{l0}\cos(\theta) \quad (23)$$

where $\ddot{n}_l$ the number of photons emitted per unit time per unit solid angle at an angle of $\theta$ off the LED's forward axial direction, and $\ddot{n}_l$ is the valve of $\ddot{n}_l$ in the forward axial direction.

The total number of photons emitted by the LED per unit time is:

$$\dot{n}_l = \int_\Omega \ddot{n}_l d\Omega \quad (24)$$
$$= \int_\Omega \ddot{n}_{l0}\cos(\theta) d\Omega$$

Now, $$\Delta\Omega = 2\pi[1-\cos(\theta+\Delta\theta)] - 2\pi[1-\cos(\theta)]$$
$$\Delta\Omega = 2\pi[\cos(\theta) - \cos(\theta+\Delta\theta)]$$
$$= 4\pi\sin(\theta)\cos\left(\frac{\Delta\theta}{2}\right)\sin\left(\frac{\Delta\theta}{2}\right) + 4\pi\cos(\theta)\sin^2\left(\frac{\Delta\theta}{2}\right)$$

$$d\Omega = 2\pi\sin(\theta)d\theta$$

Substituting this into (24):

$$\dot{n}_l = \int_0^{\frac{\pi}{2}} 2\pi\ddot{n}_{l0}\cos(\theta)\sin(\theta)d\theta$$
$$= \pi\ddot{n}_{l0}$$

Rearranging, we have:

$$\ddot{n}_{l0} = \frac{\dot{n}_l}{\pi} \quad (26)$$

The LED's output power is 0.515 W and $v_e=6.52(10)^{14}$ Hz, therefore:

$$\dot{n}_l = \frac{p_l}{hv_e} \quad (27)$$
$$= \frac{0.515}{[6.63(10)^{-34}][6.52(10)^{14}]}$$
$$= 1.19(10)^{18} \text{ photons/s}$$

Substituting this value into (26) we have:

$$\ddot{n}_{l0} = \frac{1.19(10)^{18}}{\pi}$$
$$= 3.79(10)^{17} \text{ photons/s/sr}$$

Figure 61:
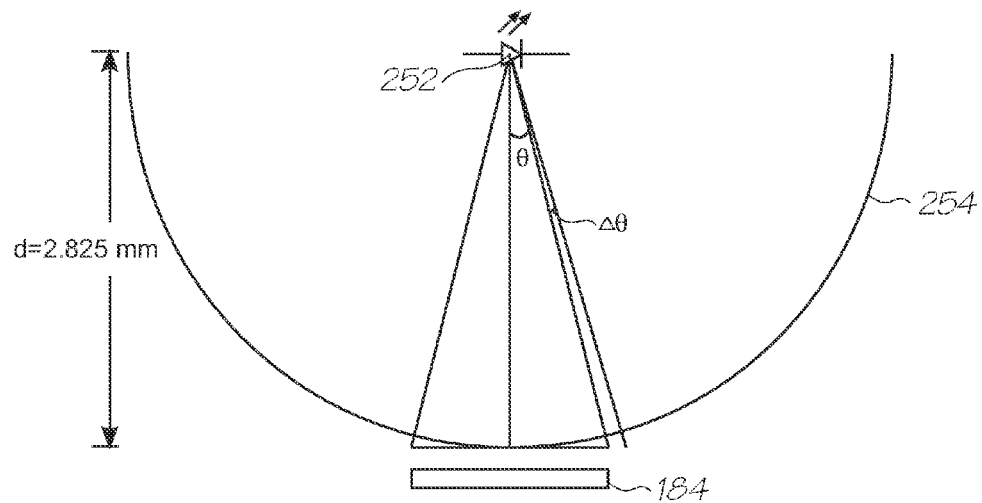
FIG. 61 is a diagram of the excitation illumination geometry of the hybridization chamber array.

Referring to FIG. 61, the optical centre 252 and the lens 254 of the LED 26 are schematically shown. The photodiodes are 16 μm×16 μm, and for the photodiode in the middle of the array, the solid angle ($\Omega$) of the cone of light emitted from the LED 26 to the photodiode 184 is approximately:

$$\Omega = \text{area of sensor}/r^2$$
$$= \frac{[16(10)^{-6}][16(10)^{-6}]}{[2.825(10)^{-3}]^2}$$
$$= 3.21(10)^{-5} sr$$

It will be appreciated that the central photodiode 184 of the photodiode array 44 is used for the purpose of these calculations. A sensor located at the edge of the array would only receive 2% less photons upon a hybridization event for a Lambertian excitation source intensity distribution.

The number of excitation photons emitted per unit time is:

$$\dot{n}_e = \ddot{n}_l\Omega \quad (28)$$
$$= [3.79(10)^{17}][3.21(10)^{-5}]$$
$$= 1.22(10)^{13} \text{ photons/s}$$

Now referring to equation (29):

$$n_s = \phi_0 \dot{n}_e F \tau_f e^{-\Delta t/\tau_f}$$

$$n_s = (0.5)[1.22(10)^{13}][3.42(10)^{-5}]$$

$$[1(10)^{-6}]e^{-4.34(10)^{-9}/1(10)^{-6}}$$

$$= 208 \text{ photons per sensor.}$$

Therefore, using the Philips LXK2-PR14-R00 LED and Pulsar 650 fluorophore, we can easily detect any hybridization events which results in this number of photons being emitted.

Figure 62:
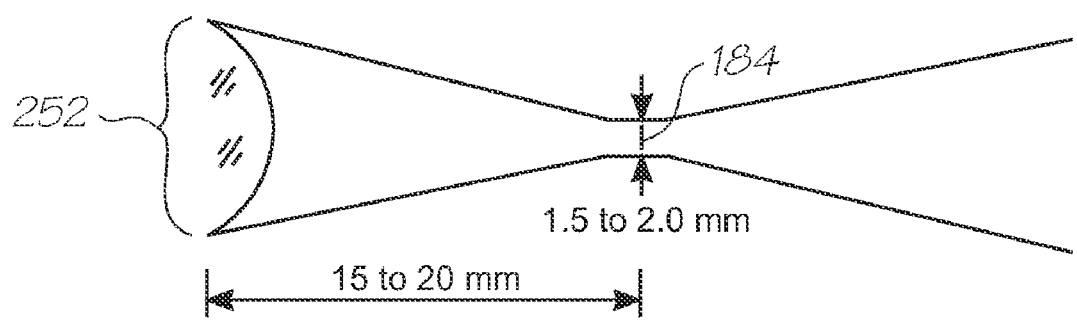
FIG. 62 is a diagram of a Sensor Electronic Technology LED illumination geometry.
Figure 63:
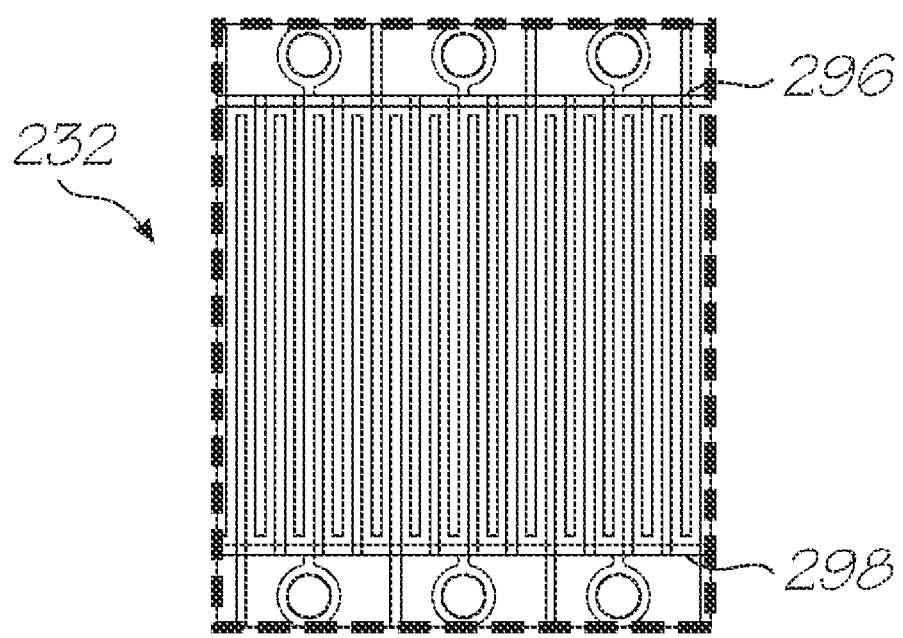
FIG. 63 is an enlarged plan view of the humidity sensor shown in Inset AH of FIG. 6.

The SET LED illumination geometry is shown in FIG. 62. At $I_D$=20 mA, the LED has a minimum optical power output of $p_1$=240 μW centred at $\lambda_e$=340 nm (the absorption wavelength of the terbium chelate). Driving the LED at $I_D$=200 mA would increase the output power linearly to $p_1$=2.4 mW. By placing the LED's optical centre 252, 17.5 mm away from the hybridization chamber array 110, we would approximately concentrate this output flux in a circular spot size which has a maximum diameter of 2 mm.

The photon flux in the 2 mm-diameter spot at the hybridization away plane is given by equation 27.

$$\dot{n}_l = \frac{p_l}{h v_e}$$

$$= \frac{2.4(10)^{-3}}{[6.63(10)^{-34}][8.82(10)^{14}]}$$

$$= 4.10(10)^{15} \text{ photons/s}$$

Using equation 28, we have:

$$\dot{n}_e = \ddot{n}_l \Omega$$

$$= 4.10(10)15 \frac{[16(10)^{-6}]^2}{\pi[1(10)^{-3}]^2}$$

$$= 3.34(10)^{11} \text{ photons/s}$$

Now, recalling equation 22 and using the Tb chelate properties listed previously, $$\Delta t = \frac{\ln[(6.94(10)^{-5})(10)(0.5)]}{\frac{1}{1(10)^{-3}} - \frac{1}{0.5(10)^{-9}}}$$

$$= 3.98(10)^{-9} s$$

Now from equation 21:

$$n_s = (0.5)[3.34(10)^{11}][6.94(10)^{-5}]$$
$$[1(10)^{-3}]e^{-3.98(10)^{-9}/1(10)^{-3}} = 11,600 \text{ photons per sensor.}$$

The theoretical number of photons emitted by hybridization events using the SET LED and terbium chelate system are easily detectable and well over the minimum of 30 photons required for reliable detection by the photosensor as indicated above.

Maximum Spacing Between Probes and Photodiode

The on-chip detection of hybridization avoids the needs for detection via confocal microscopy (see Background of the Invention). This departure from traditional detection techniques is a significant factor in the time and cost savings associated with this system. Traditional detection requires imaging optics which necessarily uses lenses or curved mirrors. By adopting non-imaging optics, the diagnostic system avoids the need for a complex and bulky optical train. Positioning the photodiode very close to the probes has the advantage of extremely high collection efficiency: when the thickness of the material between the probes and the photodiode is of the order of 1 micron, the angle of collection of emission light is up to 173°. This angle is calculated by considering light emitted from a probe at the centroid of the face of the hybridization chamber closest to the photodiode, which has a planar active surface area parallel to that chamber face. The cone of emission angles within which light is able to be absorbed by the photodiode is defined as having the emitting probe at its vertex and the corner of the sensor on the perimeter of its planar face. For a 16 micron×16 micron sensor, the vertex angle of this cone is 170°; in the limiting case where the photodiode is expanded so that its area matches that of the 29 micron×19.75 micron hybridization chamber, the vertex angle is 173°. A separation between the chamber face and the photodiode active surface of 1 micron or less is readily achievable.

Employing a non-imaging optics scheme does require the photodiode 184 to be very close to the hybridization chamber in order to collect sufficient photons of fluorescence emission. The maximum spacing between the photodiode and probes is determined as follows with reference to FIG. 54.

Utilizing a terbium chelate fluorophore and a SET UVTOP335TO39BL LED, we calculated 11600 photons reaching our 16 micron×16 micron photodiode 184 from the respective hybridization chamber 180. In performing this calculation we assumed that the light-collecting region of our hybridization chamber 180 has a base area which is the same as our photodiode active area 185, and half of the total number of the hybridization photons reaches the photodiode 184. That is, the light gathering efficiency of the optical system is $\phi_0$=0.5.

More accurately we can write $\phi_0$=[(base area of the light-collecting region of the hybridization chamber)/(photodiode area)][$\Omega/4\pi$], where $\Omega$=solid angle subtended by the photodiode at a representative point on the base of the hybridization chamber. For a right square pyramid geometry:

$\Omega$=4 arcsin($a^2/(4d_0^2+a^2)$), where $d_0$=distance between the chamber and the photodiode, and $a$ is the photodiode dimension.

Each hybridization chamber releases 23200 photons. The selected photodiode has a detection threshold of 17 photons; therefore, the minimum optical efficiency required is:

$\phi_0$=17/23200=7.33×10$^{-4}$

The base area of the light-collecting region of the hybridization chamber 180 is 29 micron×19.75 micron.

Solving for $d_0$, we will get the maximum limiting distance between the bottom of our hybridization chamber and our photodiode 184 to be $d_0$=249 microns. In this limit, the collection cone angle as defined above is only 0.8°. It should be noted this analysis ignores the negligible effect of refraction.

LOC Variant I

Figure 70:
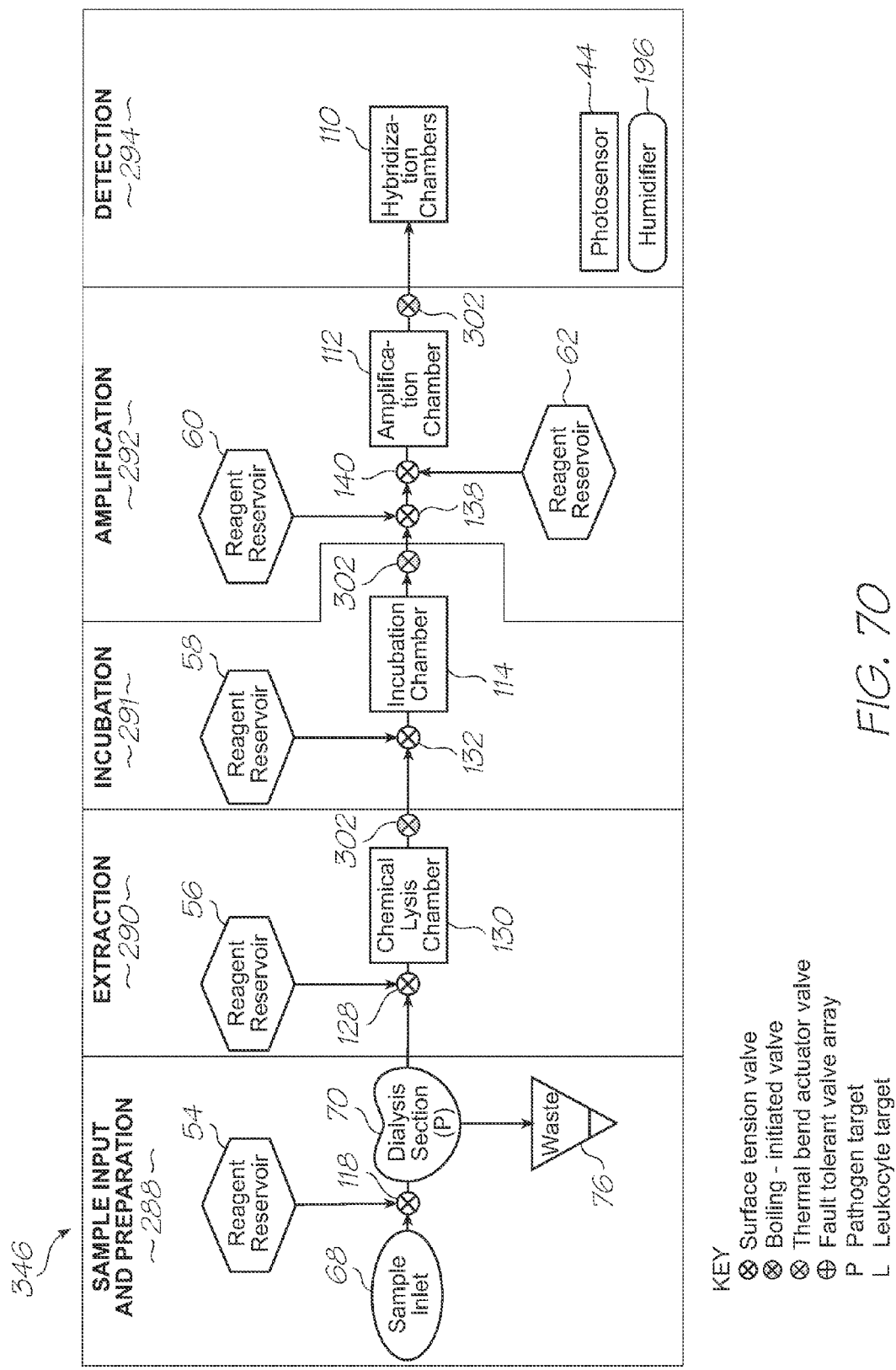
FIG. 70 is a diagrammatic representation of the architecture of a first LOC variant.

Referring to FIG. 70, LOC variant I 346 is a pathogenic DNA detection LOC device like the LOC device 301 described above with the exception that the first variant of the thermal bend actuated valves 302 are used instead of the boiling-initiated valves 126, 106 and 108. LOC variant I also omits the humidity sensor 232 but retains the humidifier 196.

LOC Variant II

Figure 68:
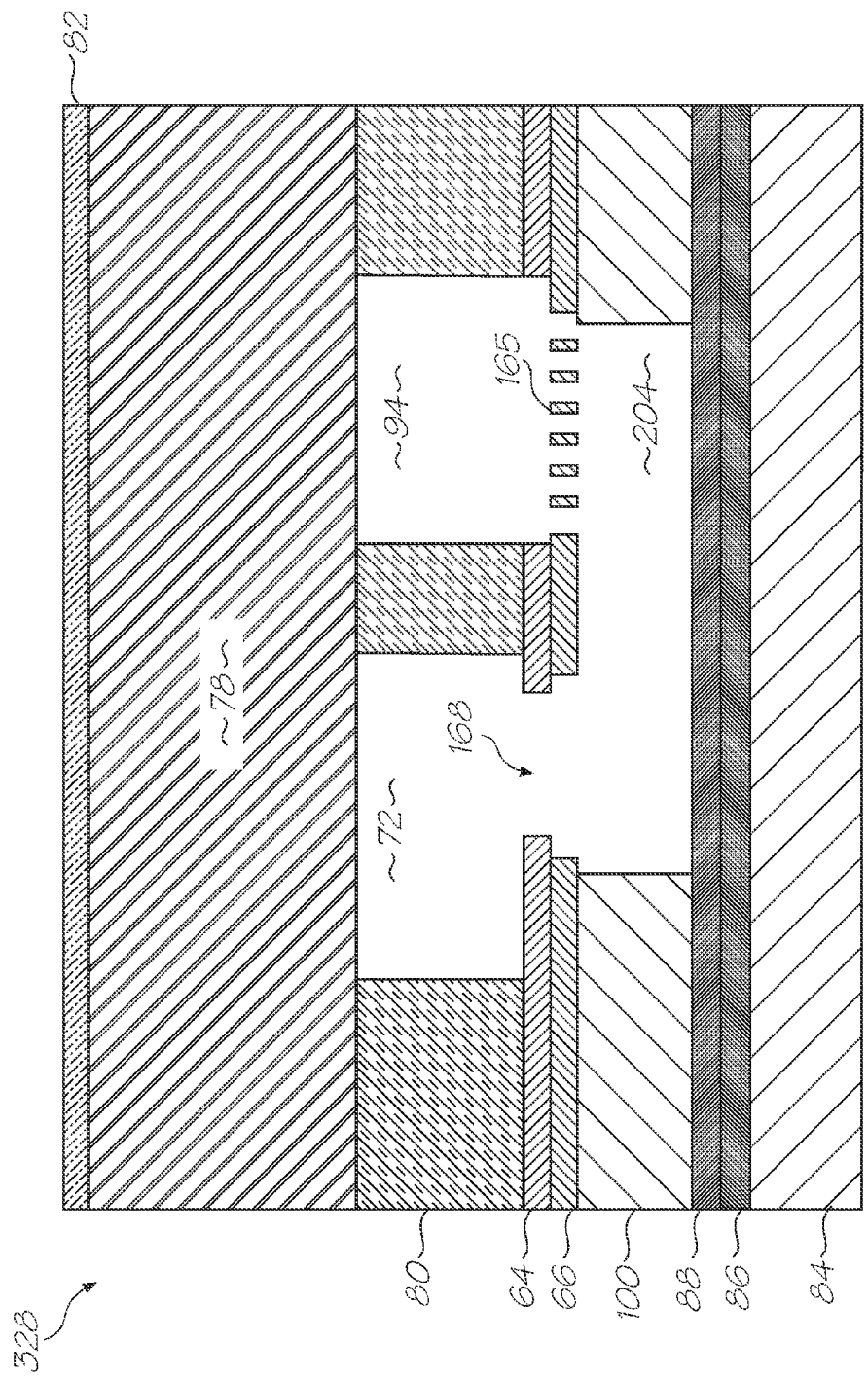
FIG. 68 is a schematic section view of a leukocyte target dialysis section.
Figure 71:
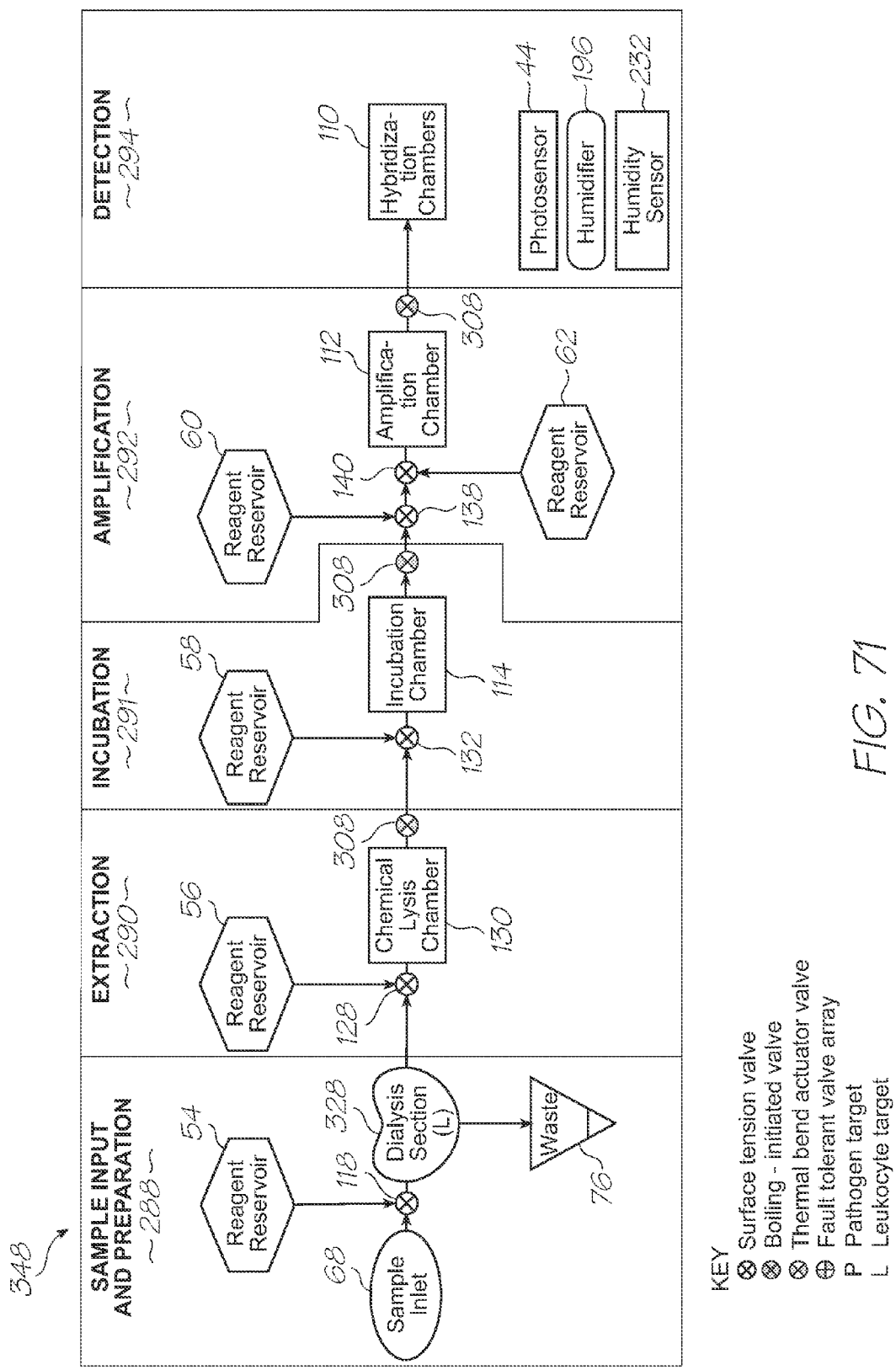
FIG. 71 is a diagrammatic representation of the architecture of a second LOC variant.

FIG. 71 shows LOC variant II 348. This LOC device extracts 290, incubates 291, amplifies 292, and detects 294 human DNA by using the leukocyte dialysis section 328 shown in FIG. 68. The second variant of thermal bend actuated valve 308 is used instead of boiling-initiated valves 126, 106 and 108 at the output to the chemical lysis 130, incubation 114 and amplification 112 sections.

CONCLUSION

The devices, systems and methods described here facilitate molecular diagnostic tests at low cost with high speed and at the point-of-care.

The system and its components described above are purely illustrative and the skilled worker in this field will readily recognize many variations and modifications which do not depart from the spirit and scope of the broad inventive concept.

The invention claimed is:

1. A microfluidic thermal bend actuated pressure pulse valve comprising:
   an inlet for receiving a flow of liquid;
   an outlet for outputting the flow of liquid, the outlet being in fluid communication with the inlet;
   a meniscus anchor between the inlet and the outlet such that the flow from the inlet towards the outlet stops at the meniscus anchor where the liquid forms a meniscus;
   a movable member for contacting the liquid; and,
   a thermal expansion actuator for displacing the movable member to generate a pulse in the liquid to dislodge the meniscus such that the liquid flow towards the outlet resumes; wherein during use,
   the liquid flow from the inlet to the meniscus anchor is via capillary action and the liquid flow immediately downstream of the meniscus anchor to the outlet is via capillary action.

2. The microfluidic valve according to claim 1 wherein the movable member is configured for movement between a quiescent position and an actuated position displaced from the quiescent position and the meniscus anchor is an aperture configured to arrest the liquid flow by pinning the meniscus at the aperture.

3. The microfluidic valve according to claim 2 wherein the movable member at least partially defines the aperture.

4. The microfluidic valve according to claim 3 wherein the thermal actuator has a resistive element for causing differential thermal expansion to move the movable member.

5. The microfluidic valve according to claim 4 further comprising a single flow-path from the inlet to the outlet wherein the actuator reciprocates the movable member between the quiescent and displaced positions until the flow-path immediately downstream of the aperture is filled enough for capillary action to re-establish the liquid flow in the flow direction.

6. The microfluidic valve according to claim 5 further comprising;
   a channel formed in a supporting substrate for at least partially defining the flow-path;
   CMOS circuitry positioned between the channel and the supporting substrate for operatively controlling the actuator valve; and,
   at least one sensor responsive to the liquid flow wherein the at least one sensor provides feedback to the CMOS circuitry for use in the operative control of the actuator valve; wherein,
   the at least one sensor is a liquid sensor for sensing the presence or absence of liquid at a position in the channel.

7. The microfluidic valve according to claim 6 wherein the aperture is a nozzle in the movable member.

8. The microfluidic valve according to claim 7 wherein the movable member is a cantilevered structure with the nozzle at the free end and the resistive element between the nozzle and the fixed end.

9. The microfluidic valve according to claim 8 wherein the movable member is formed in one wall of the channel such that in the quiescent position, an interior surface of the movable member is coplanar with an interior surface of the wall.

10. The microfluidic valve according to claim 9 wherein the channel is overlaid with a cap defining a cap channel, the cap channel defining the flow-path immediately downstream of the aperture in the movable member such that reciprocation of the movable member fills the cap channel until capillary driven flow to the outlet resumes.

11. The microfluidic valve according to claim 9 wherein the channel has a cross sectional area transverse to the flow direction less than 400 square microns.

12. The microfluidic valve according to claim 4 wherein the thermal expansion actuator comprises at least two dissimilar materials.

13. The microfluidic valve according to claim 12 wherein one of the at least two dissimilar materials is an electrical insulator.

14. The microfluidic valve according to claim 13 wherein the resistive element is a layer of titanium nitride.

15. The microfluidic valve according to claim 14 wherein the thermal actuator has a layer of silicon dioxide adjacent the titanium nitride layer.

* * * * *